US008986969B2

(12) United States Patent
Lange et al.

(10) Patent No.: US 8,986,969 B2
(45) Date of Patent: Mar. 24, 2015

(54) POLYPEPTIDES HAVING CELLOBIOHYDROLASE I ACTIVITY AND POLYNUCLEOTIDES ENCODING SAME

(71) Applicant: Novozymes A/S, Bagsvaerd (DK)

(72) Inventors: Lene Lange, Valby (DK); Wenping Wu, Beijing (CN); Dominique Aubert, Copenhagen (DK); Sara Landvik, Holte (DK); Kirk Matthew Schnorr, Holte (DK); Ib Groth Clausen, Birkeroed (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/064,457

(22) Filed: Oct. 28, 2013

(65) Prior Publication Data

US 2014/0051143 A1 Feb. 20, 2014

Related U.S. Application Data

(60) Division of application No. 13/681,490, filed on Nov. 20, 2012, now Pat. No. 8,603,794, which is a division of application No. 13/646,980, filed on Oct. 8, 2012, now Pat. No. 8,507,238, which is a division of application No. 13/483,389, filed on May 30, 2012, now Pat. No. 8,603,793, which is a division of application No. 12/818,861, filed on Jun. 18, 2010, now Pat. No. 8,338,156, which is a continuation of application No. 10/481,179, filed as application No. PCT/DK02/00429 on Jun. 26, 2002, now Pat. No. 7,785,853.

(30) Foreign Application Priority Data

Jun. 26, 2001 (DK) ................................. 2001 01000

(51) Int. Cl.
*C12N 9/14* (2006.01)
*C12P 1/00* (2006.01)
*C12P 21/04* (2006.01)
*A61K 39/00* (2006.01)
*C12N 9/42* (2006.01)
*C11D 3/386* (2006.01)
*C12P 7/14* (2006.01)

(52) U.S. Cl.
CPC .......... *C12N 9/2437* (2013.01); *C11D 3/38645* (2013.01); *C12N 9/42* (2013.01); *C12Y 302/01091* (2013.01); *C11D 3/386* (2013.01); *C12P 7/14* (2013.01); *Y02E 50/17* (2013.01)
USPC ............ 435/195; 127/36; 127/37; 424/274.1; 435/41; 435/68.1; 435/70.1; 435/71.1; 435/171; 435/183; 436/530; 514/1.1; 514/1.17; 514/54; 514/57

(58) Field of Classification Search
CPC ....... C12N 2009/00; C12P 7/06; C12P 7/065; C12P 7/10; C12P 19/14; C12P 21/021; C12P 2201/00; A61K 38/47; C12Y 101/00; C12Y 302/01004; C12Y 302/01006; Y02E 50/10; Y02E 50/16; C11D 1/008; C11D 1/72; C11D 3/38642; C11D 3/381
See application file for complete search history.

(56) References Cited

U.S. PATENT DOCUMENTS

| 5,120,463 | A | 6/1992 | Bjork et al. |
| 5,487,989 | A | 1/1996 | Fowler et al. |
| 5,955,270 | A | 9/1999 | Radford et al. |
| 6,184,019 | B1 | 2/2001 | Miettinen-Oinonen |

FOREIGN PATENT DOCUMENTS

| WO | WO 95/02675 | * | 1/1995 | ............. C11D 3/386 |
| WO | 97/14804 A1 | | 4/1997 | |
| WO | 99/06574 A1 | | 2/1999 | |
| WO | 01/04284 A1 | | 1/2001 | |
| WO | 01/25468 A1 | | 4/2001 | |
| WO | 01/79507 A2 | | 10/2001 | |

OTHER PUBLICATIONS

Azevedo et al., (J. of Gen. Micro. 1990. vol. 136:2569-2576).*
Azevedo et al., Nucleic Acids Research, vol. 18, No. 3, p. 668 (1990).
Emalfarb, Geneseq Accession No. ABA92722 (2002).
Gams et al., Transacations British Mycological Society, vol. 59, No. 3, pp. 519-522 (1972).
Ganju et al., Biochimica et Biophysica Acta, vol. 993, pp. 266-274 (1989).
Gielkens et al., Applied and Environmental Microbiology, vol. 65, No. 10, pp. 4340-4345 (1999).
Hong et al., EBI Accession No. AF421954 (2001).
Hong et al., EBI Accession No. Q96UR5 (2001).
Hong et al., EBI Accession No. AF478686 (2002).
Hong et al., Uniprot Accession No. Q8TG37 (2002).
Kvachadze et al., Biosis Accession No. PREV199800120135 (1997).
Kvachadze et al., Mikrobiologiya, vol. 66, No. 5, pp. 644-649 (1997).
Li et al., Journal of Applied Microbiology, vol. 106, pp. 1867-1875 (2009).
Radford et al., EMBL Accession No. X17258 (1990).
Riske et al., Applied and Environmental Microbiology, vol. 56, No. 11, pp. 3261-3265 (1990).
Takada et al., Journal of Fermentation and Bioengineering, vol. 85, No. 1 pp. 1-9 (1998).
Taleb et al., Gene, vol. 161, pp. 137-138 (1995).

* cited by examiner

*Primary Examiner* — Ja'Na Hines
(74) *Attorney, Agent, or Firm* — Eric J. Fechter

(57) ABSTRACT

The present invention relates to polypeptides having cellobiohydrolase I activity and polynucleotides having a nucleotide sequence which encodes for the polypeptides. The invention also relates to nucleic acid constructs, vectors, and host cells comprising the nucleic acid constructs as well as methods for producing and using the polypeptides.

17 Claims, No Drawings

US 8,986,969 B2

POLYPEPTIDES HAVING CELLOBIOHYDROLASE I ACTIVITY AND POLYNUCLEOTIDES ENCODING SAME

CROSS-REFERENCE TO RELATED APPLICATIONS

This application is a divisional of U.S. application Ser. No. 13/681,490 filed on Nov. 20, 2012, now U.S. Pat. No. 8,603,794, which is a divisional of U.S. application Ser. No. 13/646,980 filed on Oct. 8, 2012, now U.S. Pat. No. 8,507,238, which is a divisional of U.S. application Ser. No. 13/483,389 filed on May 30, 2012, now allowed, which is a divisional of U.S. application Ser. No. 12/818,861 filed on Jun. 18, 2010, now U.S. Pat. No. 8,338,156, which is a continuation of U.S. application Ser. No. 10/481,179 filed Dec. 17, 2003, now U.S. Pat. No. 7,785,853, which is a 35 U.S.C. 371 national application of international application no. PCT/DK02/000429 filed Jun. 26, 2002, which claims priority or the benefit under 35 U.S.C. 119 of Danish application no. PA 2001 01000 filed on Jun. 26, 2001, the contents of which are fully incorporated herein by reference.

FIELD OF THE INVENTION

The present invention relates to polypeptides having cellobiohydrolase I (also referred to as CBH I or CBH 1) activity and polynucleotides having a nucleotide sequence which encodes for the polypeptides. The invention also relates to nucleic acid constructs, vectors, and host cells comprising the nucleic acid constructs as well as methods for producing and using the polypeptides.

BACKGROUND OF THE INVENTION

Cellulose is an important industrial raw material and a source of renewable energy. The physical structure and morphology of native cellulose are complex and the fine details of its structure have been difficult to determine experimentally. However, the chemical composition of cellulose is simple, consisting of D-glucose residues linked by beta-1,4-glycosidic bonds to form linear polymers with chains length of over 10,000 glycosidic residues.

In order to be efficient, the digestion of cellulose requires several types of enzymes acting cooperatively. At least three categories of enzymes are necessary to convert cellulose into glucose: endo (1,4)-beta-D-glucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose.

Exo-cellobiohydrolases (Cellobiohydrolase I, or CBH I) refer to the cellobiohydrolases which degrade cellulose by hydrolyzing the cellobiose from the reducing end of the cellulose polymer chains.

It is an object of the present invention to provide improved polypeptides having cellobiohydrolase I activity and polynucleotides encoding the polypeptides. The improved polypeptides may have improved specific activity and/or improved stability—in particular improved thermostability. The polypeptides may also have an improved ability to resist inhibition by cellobiose.

SUMMARY OF THE INVENTION

In a first aspect the present invention relates to a polypeptide having cellobiohydrolase I activity, selected from the group consisting of:
(a) a polypeptide comprising an amino acid sequence selected from the group consisting of:
an amino acid sequence which has at least 80% identity with amino acids 1 to 526 of SEQ ID NO:2,
an amino acid sequence which has at least 80% identity with amino acids 1 to 529 of SEQ ID NO:4,
an amino acid sequence which has at least 80% identity with amino acids 1 to 451 of SEQ ID NO:6,
an amino acid sequence which has at least 80% identity with amino acids 1 to 457 of SEQ ID NO:8,
an amino acid sequence which has at least 80% identity with amino acids 1 to 538 of SEQ ID NO:10,
an amino acid sequence which has at least 70% identity with amino acids 1 to 415 of SEQ ID NO:12,
an amino acid sequence which has at least 70% identity with amino acids 1 to 447 of SEQ ID NO:14,
an amino acid sequence which has at least 80% identity with amino acids 1 to 452 of SEQ ID NO:16,
an amino acid sequence which has at least 80% identity with amino acids 1 to 454 of SEQ ID NO:38,
an amino acid sequence which has at least 80% identity with amino acids 1 to 458 of SEQ ID NO:40,
an amino acid sequence which has at least 80% identity with amino acids 1 to 450 of SEQ ID NO:42,
an amino acid sequence which has at least 80% identity with amino acids 1 to 446 of SEQ ID NO:44,
an amino acid sequence which has at least 80% identity with amino acids 1 to 527 of SEQ ID NO:46,
an amino acid sequence which has at least 80% identity with amino acids 1 to 455 of SEQ ID NO:48,
an amino acid sequence which has at least 80% identity with amino acids 1 to 464 of SEQ ID NO:50,
an amino acid sequence which has at least 80% identity with amino acids 1 to 460 of SEQ ID NO:52,
an amino acid sequence which has at least 80% identity with amino acids 1 to 450 of SEQ ID NO:54,
an amino acid sequence which has at least 80% identity with amino acids 1 to 532 of SEQ ID NO:56,
an amino acid sequence which has at least 80% identity with amino acids 1 to 460 of SEQ ID NO:58,
an amino acid sequence which has at least 80% identity with amino acids 1 to 525 of SEQ ID NO:60, and
an amino acid sequence which has at least 80% identity with amino acids 1 to 456 of SEQ ID NO:66;
(b) a polypeptide comprising an amino acid sequence selected from the group consisting of:
an amino acid sequence which has at least 80% identity with the polypeptide encoded by the cellobiohydrolase I encoding part of the nucleotide sequence present in *Acremonium thermophilum*,
an amino acid sequence which has at least 80% identity with the polypeptide encoded by the cellobiohydrolase I encoding part of the nucleotide sequence present in *Chaetomium thermophilum*,
an amino acid sequence which has at least 80% identity with the polypeptide encoded by the cellobiohydrolase I encoding part of the nucleotide sequence present in *Scytalidium* sp.,
an amino acid sequence which has at least 80% identity with the polypeptide encoded by the cellobiohydrolase I encoding part of the nucleotide sequence present in *Scytalidium thermophilum*, an amino acid sequence which has at least 80% identity with the polypeptide encoded by the cellobiohydrolase I encoding part of the nucleotide sequence present in *Thermoascus aurantiacus*, an amino acid sequence which has at least 80% identity with the polypeptide encoded by the cellobiohydrolase I encoding part of the nucleotide sequence present in *Thielavia australiensis*, an amino acid sequence which has at least 70% identity with the polypeptide encoded by the cellobiohydrolase I encoding part of the nucleotide sequence present in *Verticillium tenerum*, an amino acid sequence which has at least 70% identity with the polypeptide encoded by the cellobiohydrolase I encoding part of the nucleotide sequence present in *Neotermes castaneus*, an amino acid sequence which has at least 80% identity with the polypeptide encoded by the cellobiohydrolase I encoding part of the nucleotide sequence present in *Melanocarpus albomyces*, an amino acid sequence which has at least 80% identity with the polypeptide encoded by the cellobiohydrolase I encoding part of the nucleotide sequence present in *Acremonium* sp., an amino acid sequence which has at least 80% identity with the polypeptide encoded by the cellobiohydrolase I encoding part of the nucleotide sequence present in *Chaetomidium pingtungium*, an amino acid sequence which has at least 80% identity with the polypeptide encoded by the cellobiohydrolase I encoding part of the nucleotide sequence present in *Sporotrichum pruinosum*, an amino acid sequence which has at least 80% identity with the polypeptide encoded by the cellobiohydrolase I encoding part of the nucleotide sequence present in *Diplodia gossypina*, an amino acid sequence which has at least 80% identity with the polypeptide encoded by the cellobiohydrolase I encoding part of the nucleotide sequence present in *Trichophaea saccata*, an amino acid sequence which has at least 80% identity with the polypeptide encoded by the cellobiohydrolase I encoding part of the nucleotide sequence present in *Myceliophthora thermophila*, an amino acid sequence which has at least 80% identity with the polypeptide encoded by the cellobiohydrolase I encoding part of the nucleotide sequence present in *Exidia glandulosa*, an amino acid sequence which has at least 80% identity with the polypeptide encoded by the cellobiohydrolase I encoding part of the nucleotide sequence present in *Xylaria hypoxylon*, an amino acid sequence which has at least 80% identity with the polypeptide encoded by the cellobiohydrolase I encoding part of the nucleotide sequence present in *Poitrasia circinans*, an amino acid sequence which has at least 80% identity with the polypeptide encoded by the cellobiohydrolase I encoding part of the nucleotide sequence present in *Coprinus cinereus*, an amino acid sequence which has at least 80% identity with the polypeptide encoded by the cellobiohydrolase I encoding part of the nucleotide sequence present in *Pseudoplectania nigrella*, an amino acid sequence encoded by the cellobiohydrolase I encoding part of the nucleotide sequence present in *Trichothecium roseum* IFO 5372, an amino acid sequence encoded by the cellobiohydrolase I encoding part of the nucleotide sequence present in *Humicola nigrescens* CBS 819.73, an amino acid sequence encoded by the cellobiohydrolase I encoding part of the nucleotide sequence present in *Cladorrhinum foecundissimum* CBS 427.97, an amino acid sequence encoded by the cellobiohydrolase I encoding part of the nucleotide sequence present in *Diplodia gossypina* CBS 247.96, an amino acid sequence encoded by the cellobiohydrolase I encoding part of the nucleotide sequence present in *Myceliophthora thermophila* CBS 117.65, an amino acid sequence encoded by the cellobiohydrolase I encoding part of the nucleotide sequence present in *Rhizomucor pusillus* CBS 109471, an amino acid sequence encoded by the cellobiohydrolase I encoding part of the nucleotide sequence present in *Meripilus giganteus* CBS 521.95, an amino acid sequence encoded by the cellobiohydrolase I encoding part of the nucleotide sequence present in *Exidia glandulosa* CBS 2377.96, an amino acid sequence encoded by the cellobiohydrolase I encoding part of the nucleotide sequence present in *Xylaria hypoxylon* CBS 284.96, an amino acid sequence encoded by the cellobiohydrolase I encoding part of the nucleotide sequence present in *Trichophaea saccata* CBS 804.70, an amino acid sequence encoded by the cellobiohydrolase I encoding part of the nucleotide sequence present in *Chaetomium* sp., an amino acid sequence encoded by the cellobiohydrolase I encoding part of the nucleotide sequence present in *Myceliophthora hinnulea*, an amino acid sequence encoded by the cellobiohydrolase I encoding part of the nucleotide sequence present in *Thielavia* cf. microspora, an amino acid sequence encoded by the cellobiohydrolase I encoding part of the nucleotide sequence present in *Aspergillus* sp., an amino acid sequence encoded by the cellobiohydrolase I encoding part of the nucleotide sequence present in *Scopulariopsis* sp., an amino acid sequence encoded by the cellobiohydrolase I encoding part of the nucleotide sequence present in *Fusarium* sp., an amino acid sequence encoded by the cellobiohydrolase I encoding part of the nucleotide sequence present in *Verticillium* sp., and an amino acid sequence encoded by the cellobiohydrolase I encoding part of the nucleotide sequence present in *Phytophthora infestans*;

(c) a polypeptide comprising an amino acid sequence selected from the group consisting of:

an amino acid sequence which has at least 80% identity with the polypeptide encoded by nucleotides 1 to 1578 of SEQ ID NO:1, an amino acid sequence which has at least 80% identity with the polypeptide encoded by nucleotides 1 to 1587 of SEQ ID NO:3, an amino acid sequence which has at least 80% identity with the polypeptide encoded by nucleotides 1 to 1353 of SEQ ID NO:5, an amino acid sequence which has at least 80% identity with the polypeptide encoded by nucleotides 1 to 1371 of SEQ ID NO:7, an amino acid sequence which has at least 80% identity with the polypeptide encoded by nucleotides 1 to 1614 of SEQ ID NO:9,
an amino acid sequence which has at least 70% identity with the polypeptide encoded by nucleotides 1 to 1245 of SEQ ID NO:11,
an amino acid sequence which has at least 70% identity with the polypeptide encoded by nucleotides 1 to 1341 of SEQ ID NO:13,
an amino acid sequence which has at least 80% identity with the polypeptide encoded by nucleotides 1 to 1356 of SEQ ID NO:15,
an amino acid sequence which has at least 80% identity with the polypeptide encoded by nucleotides 1 to 1365 of SEQ ID NO:37,
an amino acid sequence which has at least 80% identity with the polypeptide encoded by nucleotides 1 to 1377 of SEQ ID NO:39,
an amino acid sequence which has at least 80% identity with the polypeptide encoded by nucleotides 1 to 1353 of SEQ ID NO:41,
an amino acid sequence which has at least 80% identity with the polypeptide encoded by nucleotides 1 to 1341 of SEQ ID NO:43,
an amino acid sequence which has at least 80% identity with the polypeptide encoded by nucleotides 1 to 1584 of SEQ ID NO:45,
an amino acid sequence which has at least 80% identity with the polypeptide encoded by nucleotides 1 to 1368 of SEQ ID NO:47,
an amino acid sequence which has at least 80% identity with the polypeptide encoded by nucleotides 1 to 1395 of SEQ ID NO:49,
an amino acid sequence which has at least 80% identity with the polypeptide encoded by nucleotides 1 to 1383 of SEQ ID NO:51,
an amino acid sequence which has at least 80% identity with the polypeptide encoded by nucleotides 1 to 1353 of SEQ ID NO:53,
an amino acid sequence which has at least 80% identity with the polypeptide encoded by nucleotides 1 to 1599 of SEQ ID NO:55,
an amino acid sequence which has at least 80% identity with the polypeptide encoded by nucleotides 1 to 1383 of SEQ ID NO:57,
an amino acid sequence which has at least 80% identity with the polypeptide encoded by nucleotides 1 to 1578 of SEQ ID NO:59, and
an amino acid sequence which has at least 80% identity with the polypeptide encoded by nucleotides 1 to 1371 of SEQ ID NO:65;
(d) a polypeptide which is encoded by a nucleotide sequence which hybridizes under high stringency conditions with a polynucleotide probe selected from the group consisting of:
(i) the complementary strand of the nucleotides selected from the group consisting of:
nucleotides 1 to 1578 of SEQ ID NO:1,
nucleotides 1 to 1587 of SEQ ID NO:3,
nucleotides 1 to 1353 of SEQ ID NO:5,
nucleotides 1 to 1371 of SEQ ID NO:7,
nucleotides 1 to 1614 of SEQ ID NO:9,
nucleotides 1 to 1245 of SEQ ID NO:11,
nucleotides 1 to 1341 of SEQ ID NO:13,
nucleotides 1 to 1356 of SEQ ID NO:15,
nucleotides 1 to 1365 of SEQ ID NO:37,
nucleotides 1 to 1377 of SEQ ID NO:39,
nucleotides 1 to 1353 of SEQ ID NO:41,
nucleotides 1 to 1341 of SEQ ID NO:43,
nucleotides 1 to 1584 of SEQ ID NO:45,
nucleotides 1 to 1368 of SEQ ID NO:47,
nucleotides 1 to 1395 of SEQ ID NO:49,
nucleotides 1 to 1383 of SEQ ID NO:51,
nucleotides 1 to 1353 of SEQ ID NO:53,
nucleotides 1 to 1599 of SEQ ID NO:55,
nucleotides 1 to 1383 of SEQ ID NO:57,
nucleotides 1 to 1578 of SEQ ID NO:59, and
nucleotides 1 to 1371 of SEQ ID NO:65;
(ii) the complementary strand of the nucleotides selected from the group consisting of:
nucleotides 1 to 500 of SEQ ID NO:1,
nucleotides 1 to 500 of SEQ ID NO:3,
nucleotides 1 to 500 of SEQ ID NO:5,
nucleotides 1 to 500 of SEQ ID NO:7,
nucleotides 1 to 500 of SEQ ID NO:9,
nucleotides 1 to 500 of SEQ ID NO:11,
nucleotides 1 to 500 of SEQ ID NO:13,
nucleotides 1 to 500 of SEQ ID NO:15,
nucleotides 1 to 500 of SEQ ID NO:37,
nucleotides 1 to 500 of SEQ ID NO:39,
nucleotides 1 to 500 of SEQ ID NO:41,
nucleotides 1 to 500 of SEQ ID NO:43,
nucleotides 1 to 500 of SEQ ID NO:45,
nucleotides 1 to 500 of SEQ ID NO:47,
nucleotides 1 to 500 of SEQ ID NO:49,
nucleotides 1 to 500 of SEQ ID NO:51,
nucleotides 1 to 500 of SEQ ID NO:53,
nucleotides 1 to 500 of SEQ ID NO:55,
nucleotides 1 to 500 of SEQ ID NO:57,
nucleotides 1 to 500 of SEQ ID NO:59,
nucleotides 1 to 500 of SEQ ID NO:65,
nucleotides 1 to 221 of SEQ ID NO:17,
nucleotides 1 to 239 of SEQ ID NO:18,
nucleotides 1 to 199 of SEQ ID NO:19,
nucleotides 1 to 191 of SEQ ID NO:20,
nucleotides 1 to 232 of SEQ ID NO:21,
nucleotides 1 to 467 of SEQ ID NO:22,
nucleotides 1 to 534 of SEQ ID NO:23,
nucleotides 1 to 563 of SEQ ID NO:24,
nucleotides 1 to 218 of SEQ ID NO:25,
nucleotides 1 to 492 of SEQ ID NO:26,
nucleotides 1 to 481 of SEQ ID NO:27,
nucleotides 1 to 463 of SEQ ID NO:28,
nucleotides 1 to 513 of SEQ ID NO:29,
nucleotides 1 to 579 of SEQ ID NO:30,
nucleotides 1 to 514 of SEQ ID NO:31,
nucleotides 1 to 477 of SEQ ID NO:32,
nucleotides 1 to 500 of SEQ ID NO:33,
nucleotides 1 to 470 of SEQ ID NO:34,
nucleotides 1 to 491 of SEQ ID NO:35,
nucleotides 1 to 221 of SEQ ID NO:36,
nucleotides 1 to 519 of SEQ ID NO:61,
nucleotides 1 to 497 of SEQ ID NO:62,
nucleotides 1 to 498 of SEQ ID NO:63,
nucleotides 1 to 525 of SEQ ID NO:64, and
nucleotides 1 to 951 of SEQ ID NO:67; and
(iii) the complementary strand of the nucleotides selected from the group consisting of:
nucleotides 1 to 200 of SEQ ID NO:1,
nucleotides 1 to 200 of SEQ ID NO:3,
nucleotides 1 to 200 of SEQ ID NO:5,
nucleotides 1 to 200 of SEQ ID NO:7,
nucleotides 1 to 200 of SEQ ID NO:9,
nucleotides 1 to 200 of SEQ ID NO:11, nucleotides 1 to 200 of SEQ ID NO:13,
nucleotides 1 to 200 of SEQ ID NO:15,
nucleotides 1 to 200 of SEQ ID NO:37,
nucleotides 1 to 200 of SEQ ID NO:39,
nucleotides 1 to 200 of SEQ ID NO:41,
nucleotides 1 to 200 of SEQ ID NO:43,
nucleotides 1 to 200 of SEQ ID NO:45,
nucleotides 1 to 200 of SEQ ID NO:47,
nucleotides 1 to 200 of SEQ ID NO:49,
nucleotides 1 to 200 of SEQ ID NO:51,
nucleotides 1 to 200 of SEQ ID NO:53,
nucleotides 1 to 200 of SEQ ID NO:55,
nucleotides 1 to 200 of SEQ ID NO:57,
nucleotides 1 to 200 of SEQ ID NO:59, and
nucleotides 1 to 200 of SEQ ID NO:65; and
(e) a fragment of (a), (b) or (c) that has cellobiohydrolase I activity.

In a second aspect the present invention relates to a polynucleotide having a nucleotide sequence which encodes for the polypeptide of the invention.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a polypeptide of the invention, the method comprising:
(a) cultivating a strain, which in its wild-type form is capable of producing the polypeptide, to produce the polypeptide; and
(b) recovering the polypeptide.

In a seventh aspect the present invention relates to a method for producing a polypeptide of the invention, the method comprising:
(a) cultivating a recombinant host cell of the invention under conditions conducive for production of the polypeptide; and
(b) recovering the polypeptide.

In an eight aspect the present invention relates to a method for in-situ production of a polypeptide of the invention, the method comprising:
(a) cultivating a recombinant host cell of the invention under conditions conducive for production of the polypeptide; and
(b) contacting the polypeptide with a desired substrate without prior recovery of the polypeptide.

Other aspects of the present invention will be apparent from the below description and from the appended claims.

DEFINITIONS

Prior to discussing the present invention in further details, the following terms and conventions will first be defined:

Substantially Pure Polypeptide: In the present context, the term "substantially pure polypeptide" means a polypeptide preparation which contains at the most 10% by weight of other polypeptide material with which it is natively associated (lower percentages of other polypeptide material are preferred, e.g., at the most 8% by weight, at the most 6% by weight, at the most 5% by weight, at the most 4% at the most 3% by weight, at the most 2% by weight, at the most 1% by weight, and at the most %% by weight). Thus, it is preferred that the substantially pure polypeptide is at least 92% pure, i.e., that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e., that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

Cellobiohydrolase I Activity: The term "cellobiohydrolase I activity" is defined herein as a cellulose 1,4-beta-cellobiosidase (also referred to as Exo-glucanase, Exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, releasing cellobiose from the reducing ends of the chains.

For purposes of the present invention, cellobiohydrolase I activity may be determined according to the procedure described in Example 2.

In an embodiment, cellobiohydrolase I activity may be determined according to the procedure described in Deshpande et al., Methods in Enzymology, pp. 126-130 (1988): "Selective Assay for Exo-1,4-Beta-Glucanases". According to this procedure, one unit of cellobiohydrolase I activity (agluconic bond cleavage activity) is defined as 1.0 micromole of p-nitrophenol produced per minute at 50° C., pH 5.0.

The polypeptides of the present invention should preferably have at least 20% of the cellobiohydrolase I activity of a polypeptide consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66. In a particular preferred embodiment, the polypeptides should have at least 40%, such as at least 50%, preferably at least 60%, such as at least 70%, more preferably at least 80%, such as at least 90%, most preferably at least 95%, such as about or at least 100% of the cellobiohydrolase I activity of the polypeptide consisting of the amino acid sequence selected from the group consisting of amino acids 1 to 526 of SEQ ID NO:2, amino acids 1 to 529 of SEQ ID NO:4, amino acids 1 to 451 of SEQ ID NO:6, amino acids 1 to 457 of SEQ ID NO:8, amino acids 1 to 538 of SEQ ID NO:10, amino acids 1 to 415 of SEQ ID NO:12, amino acids 1 to 447 of SEQ ID NO:14, amino acids 1 to 452 of SEQ ID NO:16, amino acids 1 to 454 of SEQ ID NO:38, amino acids 1 to 458 of SEQ ID NO:40, amino acids 1 to 450 of SEQ ID NO:42, amino acids 1 to 446 of SEQ ID NO:44, amino acids 1 to 527 of SEQ ID NO:46, amino acids 1 to 455 of SEQ ID NO:48, amino acids 1 to 464 of SEQ ID NO:50, amino acids 1 to 460 of SEQ ID NO:52, amino acids 1 to 450 of SEQ ID NO:54, amino acids 1 to 532 of SEQ ID NO:56, amino acids 1 to 460 of SEQ ID NO:58, amino acids 1 to 525 of SEQ ID NO:60, and amino acids 1 to 456 of SEQ ID NO:66.

Identity: In the present context, the homology between two amino acid sequences or between two nucleotide sequences is described by the parameter "identity".

For purposes of the present invention, the degree of identity between two amino acid sequences is determined by using the program FASTA included in version 2.0x of the FASTA program package (see Pearson and Lipman, 1988, "Improved Tools for Biological Sequence Analysis", PNAS 85:2444-2448; and Pearson, 1990, "Rapid and Sensitive Sequence Comparison with FASTP and FASTA", *Methods in Enzymology* 183:63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

Fragment: When used herein, a "fragment" of a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66 is a polypeptide having one or more amino acids deleted from the amino and/or carboxyl terminus of this amino acid sequence. Preferably, a fragment is a polypeptide having the amino acid sequence deleted corresponding to the "cellulose-binding domain" and/or the "linker domain" of *Trichoderma reesei* cellobiohydrolase I as described in SWISS-PROT accession number P00725. More preferably, a fragment comprises the amino acid sequence corresponding to the "catalytic domain" of *Trichoderma reesei* cellobiohydrolase I as described in SWISS-PROT accession number P00725. Most preferably, a fragment contains at least 434 amino acid residues, e.g., the amino acid residues selected from the group consisting of amino acids 1 to 434 of SEQ ID NO:2, amino acids 1 to 434 of SEQ ID NO:4, amino acids 1 to 434 of SEQ ID NO:6, amino acids 1 to 434 of SEQ ID NO:8, amino acids 1 to 434 of SEQ ID NO:10, amino acids 1 to 434 of SEQ ID NO:14, amino acids 1 to 434 of SEQ ID NO:16, amino acids 1 to 434 of SEQ ID NO:38, amino acids 1 to 434 of SEQ ID NO:40, amino acids 1 to 434 of SEQ ID NO:42, amino acids 1 to 434 of SEQ ID NO:44, amino acids 1 to 434 of SEQ ID NO:46, amino acids 1 to 434 of SEQ ID NO:48, amino acids 1 to 434 of SEQ ID NO:50, amino acids 1 to 434 of SEQ ID NO:52, amino acids 1 to 434 of SEQ ID NO:54, amino acids 1 to 434 of SEQ ID NO:56, amino acids 1 to 434 of SEQ ID NO:58, amino acids 1 to 434 of SEQ ID NO:60, and amino acids 1 to 434 of SEQ ID NO:66. In particular, a fragment contains at least 215 amino acid residues, e.g., the amino acid residues selected from the group consisting of amino acids 200 to 434 of SEQ ID NO:2, amino acids 200 to 434 of SEQ ID NO:4, amino acids 200 to 434 of SEQ ID NO:6, amino acids 200 to 434 of SEQ ID NO:8, amino acids 200 to 434 of SEQ ID NO:10, amino acids 200 to 415 of SEQ ID NO:12, amino acids 200 to 434 of SEQ ID NO:14, amino acids 200 to 434 of SEQ ID NO:16, amino acids 200 to 434 of SEQ ID NO:38, amino acids 200 to 434 of SEQ ID NO:40, amino acids 200 to 434 of SEQ ID NO:42, amino acids 200 to 434 of SEQ ID NO:44, amino acids 200 to 434 of SEQ ID NO:46, amino acids 200 to 434 of SEQ ID NO:48, amino acids 200 to 434 of SEQ ID NO:50, amino acids 200 to 434 of SEQ ID NO:52, amino acids 200 to 434 of SEQ ID NO:54, amino acids 200 to 434 of SEQ ID NO:56, amino acids 200 to 434 of SEQ ID NO:58, amino acids 200 to 434 of SEQ ID NO:60, and amino acids 200 to 434 of SEQ ID NO:66.

Allelic Variant: In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially Pure Polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g., at the most 8% by weight, at the most 6% by weight, at the most 5% by weight, at the most 4% at the most 3% by weight, at the most 2% by weight, at the most 1% by weight, and at the most ½% by weight). A substantially pure polynucleotide may, however, include naturally occurring 5' and 3' untranslated regions, such as promoters and terminators. It is preferred that the substantially pure polynucleotide is at least 92% pure, i.e., that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure. The polynucleotides disclosed herein are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form".

Modification(s): In the context of the present invention the term "modification(s)" is intended to mean any chemical modification of a polypeptide consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66, as well as genetic manipulation of the DNA encoding that polypeptide. The modification(s) can be replacement(s) of the amino acid side chain(s), substitution(s), deletion(s) and/or insertions(s) in or at the amino acid(s) of interest.

Artificial Variant: When used herein, the term "artificial variant" means a polypeptide having cellobiohydrolase I activity, which has been produced by an organism which is expressing a modified gene as compared to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:65. The modified gene, from which said variant is produced when expressed in a suitable host, is obtained through human intervention by modification of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic Acid Construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control Sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably Linked: The term "operably linked" is defined herein as a configuration in which a control sequence is appropriately placed at a position relative to the coding sequence of the DNA sequence such that the control sequence directs the expression of a polypeptide.

Coding Sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically include DNA, cDNA, and recombinant nucleotide sequences.

Expression: In the present context, the term "expression" includes any step involved in the production of the polypeptide including, but not limited to, transcription, post-transcriptional modification, translation, post-translational modification, and secretion.

Expression Vector: In the present context, the term "expression vector" covers a DNA molecule, linear or circular, that comprises a segment encoding a polypeptide of the invention, and which is operably linked to additional segments that provide for its transcription.

Host Cell: The term "host cell", as used herein, includes any cell type which is susceptible to transformation with a nucleic acid construct.

The terms "polynucleotide probe", "hybridization" as well as the various stringency conditions are defined in the section entitled "Polypeptides Having Cellobiohydrolase I Activity".

Thermostability: The term "thermostability", as used herein, is measured as described in Example 2.

DETAILED DESCRIPTION OF THE INVENTION

Polypeptides Having Cellobiohydrolase I Activity

In a first embodiment, the present invention relates to polypeptides having cellobiohydrolase I activity and where the polypeptides comprises, preferably consists of, an amino acid sequence which has a degree of identity to an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66 (i.e., the mature polypeptide) of at least 65%, preferably at least 70%, e.g., at least 75%, more preferably at least 80%, such as at least 85%, even more preferably at least 90%, most preferably at least 95%, e.g., at least 96%, such as at least 97%, and even most preferably at least 98%, such as at least 99% (hereinafter "homologous polypeptides"). In an interesting embodiment, the amino acid sequence differs by at the most ten amino acids (e.g., by ten amino acids), in particular by at the most five amino acids (e.g., by five amino acids), such as by at the most four amino acids (e.g., by four amino acids), e.g., by at the most three amino acids (e.g., by three amino acids) from an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66. In a particular interesting embodiment, the amino acid sequence differs by at the most two amino acids (e.g., by two amino acids), such as by one amino acid from an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66.

Preferably, the polypeptides of the present invention comprise an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66; an allelic variant thereof; or a fragment thereof that has cellobiohydrolase I activity. In another preferred embodiment, the polypeptide of the present invention consists of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66.

The polypeptide of the invention may be a wild-type cellobiohydrolase I identified and isolated from a natural source. Such wild-type polypeptides may be specifically screened for by standard techniques known in the art, such as molecular screening as described in Example 1. Furthermore, the polypeptide of the invention may be prepared by the DNA shuffling technique, such as described in Ness et al., *Nature Biotechnology* 17: 893-896 (1999). Moreover, the polypeptide of the invention may be an artificial variant which comprises, preferably consists of, an amino acid sequence that has at least one substitution, deletion and/or insertion of an amino acid as compared to an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66. Such artificial variants may be constructed by standard techniques known in the art, such as by site-directed/random mutagenesis of the polypeptide comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66. In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

Preferably, the number of such substitutions, deletions and/or insertions as compared to an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66 is at the most 10, such as at the most 9, e.g., at the most 8, more preferably at the most 7, e.g., at the most 6, such as at the most 5, most preferably at the most 4, e.g., at the most 3, such as at the most 2, in particular at the most 1.

The present inventors have isolated nucleotide sequences encoding polypeptides having cellobiohydrolase I activity from the microorganisms selected from the group consisting of *Acremonium thermophilum, Chaetomium thermophilum, Scytalidium* sp., *Scytalidium thermophilum, Thermoascus aurantiacus, Thielavia australiensis, Verticillium tenerum, Melanocarpus albomyces, Poitrasia circinans, Coprinus cinereus, Trichothecium roseum, Humicola nigrescens, Cladorrhinum foecundissimum, Diplodia gossypina, Myceliophthora thermophila, Rhizomucor pusillus, Meripilus giganteus, Exidia glandulosa, Xylaria hypoxylon, Trichophaea saccata, Acremonium* sp., *Chaetomium* sp., *Chaetomidium pingtungium, Myceliophthora thermophila, Myceliophthora hinnulea, Sporotrichum pruinosum, Thielavia* cf. *microspora, Aspergillus* sp., *Scopulariopsis* sp., *Fusarium* sp., *Verticillium* sp., *Pseudoplectania nigrella,* and *Phytophthora infestans*; and from the gut of the termite larvae *Neotermes castaneus*. Thus, in a second embodiment, the present invention relates to polypeptides comprising an amino acid sequence which has at least 65% identity with the polypeptide encoded by the cellobiohydrolase I encoding part of the nucleotide sequence present in an organism selected from the group consisting of *Acremonium thermophilum, Chaetomium thermophilum, Scytalidium* sp., *Scytalidium thermophilum, Thermoascus aurantiacus, Thielavia australiensis, Verticillium tenerum, Neotermes castaneus, Melanocarpus albomyces, Poitrasia circinans, Coprinus cinereus, Trichothecium roseum* IFO 5372, *Humicola nigrescens* CBS 819.73, *Cladorrhinum foecundissimum* CBS 427.97, *Diplodia gossypina* CBS 247.96, *Myceliophthora thermophila* CBS 117.65, *Rhizomucor pusillus* CBS 109471, *Meripilus giganteus* CBS 521.95, *Exidia glandulosa* CBS 2377.96, *Xylaria hypoxylon* CBS 284.96, *Trichophaea saccata* CBS 804.70, *Acremonium* sp., *Chaetomium* sp., *Chaetomidium pingtungium, Myceliophthora thermophila, Myceliophthora hinnulea, Sporotrichum pruinosum, Thielavia* cf. microspora, *Aspergillus* sp., *Scopulariopsis* sp., *Fusarium* sp., *Verticillium* sp., *Pseudoplectania nigrella,* and *Phytophthora infestans*. In an interesting embodiment of the invention, the polypeptide comprises an amino acid sequence which has at least 70%, e.g., at least 75%, preferably at least 80%, such as at least 85%, more preferably at least 90%, most preferably at least 95%, e.g., at least 96%, such as at least 97%, and even most preferably at least 98%, such as at least 99% identity with the polypeptide encoded by the cellobiohydrolase I encoding part of the nucleotide sequence present in an organism selected from the group consisting of *Acremonium thermophilum, Chaetomium thermophilum, Scytalidium* sp., *Scytalidium thermophilum, Thermoascus aurantiacus, Thielavia australiensis, Verticillium tenerum, Neotermes castaneus, Melanocarpus albomyces, Poitrasia circinans, Coprinus cinereus, Trichothecium roseum* IFO 5372, *Humicola nigrescens* CBS 819.73, *Cladorrhinum foecundissimum* CBS 427.97, *Diplodia gossypina* CBS 247.96, *Myceliophthora thermophila* CBS 117.65, *Rhizomucor pusillus* CBS 109471, *Meripilus giganteus* CBS 521.95, *Exidia glandulosa* CBS 2377.96, *Xylaria hypoxylon* CBS 284.96, *Trichophaea saccata* CBS 804.70, *Acremonium* sp., *Chaetomium* sp., *Chaetomidium pingtungium, Myceliophthora thermophila, Myceliophthora hinnulea, Sporotrichum pruinosum, Thielavia* cf. microspora, *Aspergillus* sp., *Scopulariopsis* sp., Fusarium sp., Verticillium sp., Pseudoplectania nigrella, and Phytophthora infestans (hereinafter "homologous polypeptides"). In an interesting embodiment, the amino acid sequence differs by at the most ten amino acids (e.g., by ten amino acids), in particular by at the most five amino acids (e.g., by five amino acids), such as by at the most four amino acids (e.g., by four amino acids), e.g., by at the most three amino acids (e.g., by three amino acids) from the polypeptide encoded by the cellobiohydrolase I encoding part of the nucleotide sequence present in an organism selected from the group consisting of Acremonium thermophilum, Chaetomium thermophilum, Scytalidium sp., Scytalidium thermophilum, Thermoascus aurantiacus, Thielavia australiensis, Verticillium tenerum, Neotermes castaneus, Melanocarpus albomyces, Poitrasia circinans, Coprinus cinereus, Trichothecium roseum IFO 5372, Humicola nigrescens CBS 819.73, Cladorrhinum foecundissimum CBS 427.97, Diplodia gossypina CBS 247.96, Myceliophthora thermophila CBS 117.65, Rhizomucor pusillus CBS 109471, Meripilus giganteus CBS 521.95, Exidia glandulosa CBS 2377.96, Xylaria hypoxylon CBS 284.96, Trichophaea saccata CBS 804.70, Acremonium sp., Chaetomium sp., Chaetomidium pingtungium, Myceliophthora thermophila, Myceliophthora hinnulea, Sporotrichum pruinosum, Thielavia cf. microspora, Aspergillus sp., Scopulariopsis sp., Fusarium sp., Verticillium sp., Pseudoplectania nigrella, and Phytophthora infestans. In a particular interesting embodiment, the amino acid sequence differs by at the most two amino acids (e.g., by two amino acids), such as by one amino acid from the polypeptide encoded by the cellobiohydrolase I encoding part of the nucleotide sequence present in an organism selected from the group consisting of Acremonium thermophilum, Chaetomium thermophilum, Scytalidium sp., Scytalidium thermophilum, Thermoascus aurantiacus, Thielavia australiensis, Verticillium tenerum, Neotermes castaneus, Melanocarpus albomyces, Poitrasia circinans, Coprinus cinereus, Trichothecium roseum IFO 5372, Humicola nigrescens CBS 819.73, Cladorrhinum foecundissimum CBS 427.97, Diplodia gossypina CBS 247.96, Myceliophthora thermophila CBS 117.65, Rhizomucor pusillus CBS 109471, Meripilus giganteus CBS 521.95, Exidia glandulosa CBS 2377.96, Xylaria hypoxylon CBS 284.96, Trichophaea saccata CBS 804.70, Acremonium sp., Chaetomium sp., Chaetomidium pingtungium, Myceliophthora thermophila, Myceliophthora hinnulea, Sporotrichum pruinosum, Thielavia cf. microspora, Aspergillus sp., Scopulariopsis sp., Fusarium sp., Verticillium sp., Pseudoplectania nigrella, and Phytophthora infestans.

Preferably, the polypeptides of the present invention comprise the amino acid sequence of the polypeptide encoded by the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CBS 109513, DSM 14348, CGMCC No. 0580, DSM 15064, DSM 15065, DSM 15066, DSM 15067, CGMCC No. 0747, CGMCC No. 0748, CGMCC No. 0749, and CGMCC No. 0750. In another preferred embodiment, the polypeptide of the present invention consists of the amino acid sequence of the polypeptide encoded by the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CBS 109513, DSM 14348, and CGMCC No. 0580, DSM 15064, DSM 15065, DSM 15066, DSM 15067, CGMCC No. 0747, CGMCC No. 0748, CGMCC No. 0749, and CGMCC No. 0750.

In a similar way as described above, the polypeptide of the invention may be an artificial variant which comprises, preferably consists of, an amino acid sequence that has at least one substitution, deletion and/or insertion of an amino acid as compared to the amino acid sequence encoded by the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CBS 109513, DSM 14348, and CGMCC No. 0580, DSM 15064, DSM 15065, DSM 15066, DSM 15067, CGMCC No. 0747, CGMCC No. 0748, CGMCC No. 0749, and CGMCC No. 0750.

In a third embodiment, the present invention relates to polypeptides having cellobiohydrolase I activity which are encoded by nucleotide sequences which hybridize under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of (i) the complementary strand of the nucleotides selected from the group consisting of:
nucleotides 1 to 1578 of SEQ ID NO:1,
nucleotides 1 to 1587 of SEQ ID NO:3,
nucleotides 1 to 1353 of SEQ ID NO:5,
nucleotides 1 to 1371 of SEQ ID NO:7,
nucleotides 1 to 1614 of SEQ ID NO:9,
nucleotides 1 to 1245 of SEQ ID NO:11,
nucleotides 1 to 1341 of SEQ ID NO:13,
nucleotides 1 to 1356 of SEQ ID NO:15,
nucleotides 1 to 1365 of SEQ ID NO:37,
nucleotides 1 to 1377 of SEQ ID NO:39,
nucleotides 1 to 1353 of SEQ ID NO:41,
nucleotides 1 to 1341 of SEQ ID NO:43,
nucleotides 1 to 1584 of SEQ ID NO:45,
nucleotides 1 to 1368 of SEQ ID NO:47,
nucleotides 1 to 1395 of SEQ ID NO:49,
nucleotides 1 to 1383 of SEQ ID NO:51,
nucleotides 1 to 1353 of SEQ ID NO:53,
nucleotides 1 to 1599 of SEQ ID NO:55,
nucleotides 1 to 1383 of SEQ ID NO:57,
nucleotides 1 to 1578 of SEQ ID NO:59, and
nucleotides 1 to 1371 of SEQ ID NO:65;

(ii) the complementary strand of the nucleotides selected from the group consisting of
nucleotides 1 to 500 of SEQ ID NO:1,
nucleotides 1 to 500 of SEQ ID NO:3,
nucleotides 1 to 500 of SEQ ID NO:5,
nucleotides 1 to 500 of SEQ ID NO:7,
nucleotides 1 to 500 of SEQ ID NO:9,
nucleotides 1 to 500 of SEQ ID NO:11,
nucleotides 1 to 500 of SEQ ID NO:13,
nucleotides 1 to 500 of SEQ ID NO:15,
nucleotides 1 to 500 of SEQ ID NO:37,
nucleotides 1 to 500 of SEQ ID NO:39,
nucleotides 1 to 500 of SEQ ID NO:41,
nucleotides 1 to 500 of SEQ ID NO:43,
nucleotides 1 to 500 of SEQ ID NO:45,
nucleotides 1 to 500 of SEQ ID NO:47,
nucleotides 1 to 500 of SEQ ID NO:49,
nucleotides 1 to 500 of SEQ ID NO:51, nucleotides 1 to 500 of SEQ ID NO:53,
nucleotides 1 to 500 of SEQ ID NO:55,
nucleotides 1 to 500 of SEQ ID NO:57,
nucleotides 1 to 500 of SEQ ID NO:59,
nucleotides 1 to 500 of SEQ ID NO:65,
nucleotides 1 to 221 of SEQ ID NO:17,
nucleotides 1 to 239 of SEQ ID NO:18,
nucleotides 1 to 199 of SEQ ID NO:19,
nucleotides 1 to 191 of SEQ ID NO:20,
nucleotides 1 to 232 of SEQ ID NO:21,
nucleotides 1 to 467 of SEQ ID NO:22,
nucleotides 1 to 534 of SEQ ID NO:23,
nucleotides 1 to 563 of SEQ ID NO:24,
nucleotides 1 to 218 of SEQ ID NO:25,
nucleotides 1 to 492 of SEQ ID NO:26,
nucleotides 1 to 481 of SEQ ID NO:27,
nucleotides 1 to 463 of SEQ ID NO:28,
nucleotides 1 to 513 of SEQ ID NO:29,
nucleotides 1 to 579 of SEQ ID NO:30,
nucleotides 1 to 514 of SEQ ID NO:31,
nucleotides 1 to 477 of SEQ ID NO:32,
nucleotides 1 to 500 of SEQ ID NO:33,
nucleotides 1 to 470 of SEQ ID NO:34,
nucleotides 1 to 491 of SEQ ID NO:35,
nucleotides 1 to 221 of SEQ ID NO:36,
nucleotides 1 to 519 of SEQ ID NO:61,
nucleotides 1 to 497 of SEQ ID NO:62,
nucleotides 1 to 498 of SEQ ID NO:63,
nucleotides 1 to 525 of SEQ ID NO:64, and
nucleotides 1 to 951 of SEQ ID NO:67; and
(iii) the complementary strand of the nucleotides selected from the group consisting of
nucleotides 1 to 200 of SEQ ID NO:1,
nucleotides 1 to 200 of SEQ ID NO:3,
nucleotides 1 to 200 of SEQ ID NO:5,
nucleotides 1 to 200 of SEQ ID NO:7,
nucleotides 1 to 200 of SEQ ID NO:9,
nucleotides 1 to 200 of SEQ ID NO:11,
nucleotides 1 to 200 of SEQ ID NO:13,
nucleotides 1 to 200 of SEQ ID NO:15,
nucleotides 1 to 200 of SEQ ID NO:37,
nucleotides 1 to 200 of SEQ ID NO:39,
nucleotides 1 to 200 of SEQ ID NO:41,
nucleotides 1 to 200 of SEQ ID NO:43,
nucleotides 1 to 200 of SEQ ID NO:45,
nucleotides 1 to 200 of SEQ ID NO:47,
nucleotides 1 to 200 of SEQ ID NO:49,
nucleotides 1 to 200 of SEQ ID NO:51,
nucleotides 1 to 200 of SEQ ID NO:53,
nucleotides 1 to 200 of SEQ ID NO:55,
nucleotides 1 to 200 of SEQ ID NO:57,
nucleotides 1 to 200 of SEQ ID NO:59, and
nucleotides 1 to 200 of SEQ ID NO:65
(Sambrook et al., 1989, *Molecular Cloning, A Laboratory Manual,* 2d edition, Cold Spring Harbor, N.Y.).

In another embodiment, the present invention relates to polypeptides having cellobiohydrolase I activity which are encoded by the cellobiohydrolase I encoding part of the nucleotide sequence present in a microorganism selected from the group consisting of:

a microorganism belonging to Zygomycota, preferably belonging to the Mucorales, more preferably belonging to the family Mucoraceae, most preferably belonging to the genus *Rhizomucor* (e.g., *Rhizomucor pusillus*), or the family Choanephoraceae, most preferably belonging to the genus *Poitrasia* (e.g., *Poitrasia circinans*), a microorganism belonging to the Oomycetes, preferably to the order Pythiales, more preferably to the family Pythiaceae, most preferably to the genus *Phytophthora* (e.g., *Phytophthora infestans*), a microorganism belonging to Auriculariales (an order of the Basidiomycota, Hymenomycetes), preferably belonging to the family Exidiaceae, more preferably belonging to the genus *Exidia* (e.g., *Exidia glandulosa*), a microorganism belonging to Xylariales (an order of the Ascomycota, Sordariomycetes), preferably belonging to the family Xylariaceae, more preferably belonging to the genus *Xylaria* (e.g., *Xylaria hypoxylon*), a microorganism belonging to Dothideales (an order of the Ascomycota, Dothideomycetes), preferably belonging to the family Dothideaceae, more preferably belonging to the genus *Diplodia* (e.g., *Diplodia gossypina*), a microorganism belonging to Pezizales (an order of the Ascomycota), preferably belonging to the family Pyronemataceae, more preferably belonging to the genus *Trichophaea* (e.g., *Trichophaea saccata*), or the family Sarcosomataceae, more preferably belonging to the genus *Pseudoplectania* (e.g., *Pseudoplectania nigrella*), a microorganism belonging to the family Rigidiporaceae (under Basidiomycota, Hymenomycetes, Hymenomycetales), more preferably belonging to the genus *Meripilus* (e.g., *Meripilus giganteus*), a microorganism belonging to the family Meruliaceae (under Basidiomycota, Hymenomycetes, Sterealesales), more preferably belonging to the genus *Sporothrichum* (*Sporothrichum* sp.), a microorganism belonging to the family Agaricaceae (under Basidiomycota, Hymenomycetes, Agaricales), more preferably belonging to the genus *Coprinus* (e.g., *Coprinus cinereus*), a microorganism belonging to the family Hypocreaceae (under Ascomycota, Sordariomycetes, Hypocreales), more preferably belonging to the genus *Acremonium* (e.g., *Acremonium thermophilum; Acremonium* sp.) or the (mitosporic) genus *Verticillium* (e.g., *Verticillium tenerum*), a microorganism belonging to the genus *Cladorrhinum* (under Ascomycota, Sordariomycetes, Sordariales, Sordariaceae) e.g., *Cladorrhinum foecundissimum,* a microorganism belonging to the genus *Myceliophthora* (under Ascomycota, Sordariomycetes, Sordariales, Sordariaceae) e.g., *Myceliophthora thermophila* or *Myceliophthora hinnulae,* a microorganism belonging to the genus *Chaetomium* (under Ascomycota, Sordariomycetes, Sordariales, Chaetomiaceae) e.g., *Chaetomium thermophilum,* a microorganism belonging to the genus *Chaetomidium* (under Ascomycota, Sordariomycetes, Sordariales, Chaetomiaceae) e.g., *Chaetomidium pingtungium,* a microorganism belonging to the genus *Thielavia* (under Ascomycota, Sordariomycetes, Sordariales, Chaetomiaceae) e.g., *Thielavia australiensis* or *Thielavia microspora,* a microorganism belonging to the genus *Thermoascus* (under Ascomycota, Eurotiomycetes, Eurotiales, Trichocomoaceae) e.g., *Thermoascus aurantiacus,* a microorganism belonging to the genus *Trichothecium* (mitosporic Ascomycota) e.g., *Trichothecium roseum,* and a microorganism belonging to the species *Humicola nigrescens.*

A nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:65, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:61, SEQ ID NO:62, SEQ ID NO:63, SEQ ID NO:64, and SEQ ID NO:67, or a subsequence thereof, as well as an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66, or a fragment thereof, may be used to design a polynucleotide probe to identify and clone DNA encoding polypeptides having cellobiohydrolase I activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is, however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labeled for detecting the corresponding gene (for example, with $^{32}P$, $^{3}H$, $^{35}S$, biotin, or avidin).

Thus, a genomic DNA or cDNA library prepared from such other organisms may be screened for DNA which hybridizes with the probes described above and which encodes a polypeptide having cellobiohydrolase I activity. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA which is homologous with SEQ ID NO:1 the carrier material with the immobilized DNA is used in a Southern blot.

For purposes of the present invention, hybridization indicates that the nucleotide sequence hybridizes to a labeled polynucleotide probe which hybridizes to the nucleotide sequence shown in SEQ ID NO:1 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of the nucleotides selected from the group consisting of:
nucleotides 1 to 1578 of SEQ ID NO:1,
nucleotides 1 to 1302 of SEQ ID NO:1,
nucleotides 1 to 1587 of SEQ ID NO:3,
nucleotides 1 to 1302 of SEQ ID NO:3,
nucleotides 1 to 1353 of SEQ ID NO:5,
nucleotides 1 to 1302 of SEQ ID NO:5,
nucleotides 1 to 1371 of SEQ ID NO:7,
nucleotides 1 to 1302 of SEQ ID NO:7,
nucleotides 1 to 1614 of SEQ ID NO:9,
nucleotides 1 to 1302 of SEQ ID NO:9,
nucleotides 1 to 1245 of SEQ ID NO:11,
nucleotides 1 to 1341 of SEQ ID NO:13,
nucleotides 1 to 1302 of SEQ ID NO:13,
nucleotides 1 to 1356 of SEQ ID NO:15,
nucleotides 1 to 1302 of SEQ ID NO:15,
nucleotides 1 to 1365 of SEQ ID NO:37,
nucleotides 1 to 1302 of SEQ ID NO:37,
nucleotides 1 to 1377 of SEQ ID NO:39,
nucleotides 1 to 1302 of SEQ ID NO:39,
nucleotides 1 to 1353 of SEQ ID NO:41,
nucleotides 1 to 1302 of SEQ ID NO:41,
nucleotides 1 to 1341 of SEQ ID NO:43,
nucleotides 1 to 1302 of SEQ ID NO:43,
nucleotides 1 to 1584 of SEQ ID NO:45,
nucleotides 1 to 1302 of SEQ ID NO:45,
nucleotides 1 to 1368 of SEQ ID NO:47,
nucleotides 1 to 1302 of SEQ ID NO:47,
nucleotides 1 to 1395 of SEQ ID NO:49,
nucleotides 1 to 1302 of SEQ ID NO:49,
nucleotides 1 to 1383 of SEQ ID NO:51,
nucleotides 1 to 1302 of SEQ ID NO:51,
nucleotides 1 to 1353 of SEQ ID NO:53,
nucleotides 1 to 1302 of SEQ ID NO:53,
nucleotides 1 to 1599 of SEQ ID NO:55,
nucleotides 1 to 1302 of SEQ ID NO:55,
nucleotides 1 to 1383 of SEQ ID NO:57,
nucleotides 1 to 1302 of SEQ ID NO:57,
nucleotides 1 to 1578 of SEQ ID NO:59,
nucleotides 1 to 1302 of SEQ ID NO:59,
nucleotides 1 to 1371 of SEQ ID NO:65, and
nucleotides 1 to 1302 of SEQ ID NO:65;
or the complementary strand of the nucleotides selected from the group consisting of:
nucleotides 1 to 500 of SEQ ID NO:1,
nucleotides 1 to 500 of SEQ ID NO:3,
nucleotides 1 to 500 of SEQ ID NO:5,
nucleotides 1 to 500 of SEQ ID NO:7,
nucleotides 1 to 500 of SEQ ID NO:9,
nucleotides 1 to 500 of SEQ ID NO:11,
nucleotides 1 to 500 of SEQ ID NO:13,
nucleotides 1 to 500 of SEQ ID NO:15,
nucleotides 1 to 500 of SEQ ID NO:37,
nucleotides 1 to 500 of SEQ ID NO:39,
nucleotides 1 to 500 of SEQ ID NO:41,
nucleotides 1 to 500 of SEQ ID NO:43,
nucleotides 1 to 500 of SEQ ID NO:45,
nucleotides 1 to 500 of SEQ ID NO:47,
nucleotides 1 to 500 of SEQ ID NO:49,
nucleotides 1 to 500 of SEQ ID NO:51,
nucleotides 1 to 500 of SEQ ID NO:53,
nucleotides 1 to 500 of SEQ ID NO:55,
nucleotides 1 to 500 of SEQ ID NO:57,
nucleotides 1 to 500 of SEQ ID NO:59,
nucleotides 1 to 500 of SEQ ID NO:65,
nucleotides 1 to 221 of SEQ ID NO:17,
nucleotides 1 to 239 of SEQ ID NO:18,
nucleotides 1 to 199 of SEQ ID NO:19,
nucleotides 1 to 191 of SEQ ID NO:20,
nucleotides 1 to 232 of SEQ ID NO:21,
nucleotides 1 to 467 of SEQ ID NO:22, nucleotides 1 to 534 of SEQ ID NO:23,
nucleotides 1 to 563 of SEQ ID NO:24,
nucleotides 1 to 218 of SEQ ID NO:25,
nucleotides 1 to 492 of SEQ ID NO:26,
nucleotides 1 to 481 of SEQ ID NO:27,
nucleotides 1 to 463 of SEQ ID NO:28,
nucleotides 1 to 513 of SEQ ID NO:29,
nucleotides 1 to 579 of SEQ ID NO:30,
nucleotides 1 to 514 of SEQ ID NO:31,
nucleotides 1 to 477 of SEQ ID NO:32,
nucleotides 1 to 500 of SEQ ID NO:33,
nucleotides 1 to 470 of SEQ ID NO:34,
nucleotides 1 to 491 of SEQ ID NO:35,
nucleotides 1 to 221 of SEQ ID NO:36,
nucleotides 1 to 519 of SEQ ID NO:61,
nucleotides 1 to 497 of SEQ ID NO:62,
nucleotides 1 to 498 of SEQ ID NO:63,
nucleotides 1 to 525 of SEQ ID NO:64, and
nucleotides 1 to 951 of SEQ ID NO:67;
or the complementary strand of the nucleotides selected from the group consisting of:
nucleotides 1 to 200 of SEQ ID NO:1,
nucleotides 1 to 200 of SEQ ID NO:3,
nucleotides 1 to 200 of SEQ ID NO:5,
nucleotides 1 to 200 of SEQ ID NO:7,
nucleotides 1 to 200 of SEQ ID NO:9,
nucleotides 1 to 200 of SEQ ID NO:11,
nucleotides 1 to 200 of SEQ ID NO:13,
nucleotides 1 to 200 of SEQ ID NO:15,
nucleotides 1 to 200 of SEQ ID NO:37,
nucleotides 1 to 200 of SEQ ID NO:39,
nucleotides 1 to 200 of SEQ ID NO:41,
nucleotides 1 to 200 of SEQ ID NO:43,
nucleotides 1 to 200 of SEQ ID NO:45,
nucleotides 1 to 200 of SEQ ID NO:47,
nucleotides 1 to 200 of SEQ ID NO:49,
nucleotides 1 to 200 of SEQ ID NO:51,
nucleotides 1 to 200 of SEQ ID NO:53,
nucleotides 1 to 200 of SEQ ID NO:55,
nucleotides 1 to 200 of SEQ ID NO:57,
nucleotides 1 to 200 of SEQ ID NO:59,
nucleotides 1 to 200 of SEQ ID NO:65,
nucleotides 1 to 200 of SEQ ID NO:22,
nucleotides 1 to 200 of SEQ ID NO:23,
nucleotides 1 to 200 of SEQ ID NO:24,
nucleotides 1 to 200 of SEQ ID NO:26,
nucleotides 1 to 200 of SEQ ID NO:27,
nucleotides 1 to 200 of SEQ ID NO:28,
nucleotides 1 to 200 of SEQ ID NO:29,
nucleotides 1 to 200 of SEQ ID NO:30,
nucleotides 1 to 200 of SEQ ID NO:31,
nucleotides 1 to 200 of SEQ ID NO:32,
nucleotides 1 to 200 of SEQ ID NO:33,
nucleotides 1 to 200 of SEQ ID NO:34,
nucleotides 1 to 200 of SEQ ID NO:35,
nucleotides 1 to 200 of SEQ ID NO:61,
nucleotides 1 to 200 of SEQ ID NO:62,
nucleotides 1 to 200 of SEQ ID NO:63,
nucleotides 1 to 200 of SEQ ID NO:64, and
nucleotides 1 to 200 of SEQ ID NO:67.

In another interesting embodiment, the polynucleotide probe is the complementary strand of the nucleotide sequence which encodes a polypeptide selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66. In a further interesting embodiment, the polynucleotide probe is the complementary strand of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65. In another interesting embodiment, the polynucleotide probe is the complementary strand of the nucleotide sequence contained in a plasmid which is contained in a deposited microorganism selected from the group consisting of CGMCC No. 0584, CGMCC No. 0581, CGMCC No. 0585, CGMCC No. 0582, CGMCC No. 0583, CGMCC No. 0580, CBS 109513, DSM 14348, DSM 15064, DSM 15065, DSM 15066, DSM 15067, CGMCC No. 0747, CGMCC No. 0748, CGMCC No. 0749, and CGMCC No. 0750.

For long probes of at least 100 nucleotides in length, very low to very high stringency conditions are defined as prehybridization and hybridization at 42° C. in 5×SSPE, 1.0% SDS, 5×Denhardt's solution, 100 micrograms/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g., probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated $T_m$.

Sources for Polypeptides Having Cellobiohydrolase I Activity

A polypeptide of the present invention may be obtained from microorganisms of any genus. For purposes of the present invention, the term "obtained from" as used herein shall mean that the polypeptide encoded by the nucleotide sequence is produced by a cell in which the nucleotide sequence is naturally present or into which the nucleotide sequence has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a *Candida, Kluyveromyces, Neocallimastix, Pichia, Piromyces, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neurospora, Paecilomyces, Penicillium, Schizophyllum, Talaromyces, Thermoascus, Thielavia, Tolypocladium*, or *Trichoderma* polypeptide.

In an interesting embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another interesting embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

In a preferred embodiment, the polypeptide is a *Acremonium thermophilum, Chaetomium thermophilum, Scytalidium* sp., *Scytalidium thermophilum, Thermoascus aurantiacus, Thielavia australiensis, Verticillium tenerum, Neotermes castaneus, Melanocarpus albomyces, Poitrasia circinans, Coprinus cinereus, Trichothecium roseum, Humicola nigrescens, Cladorrhinum foecundissimum, Diplodia gossypina, Myceliophthora thermophila, Rhizomucor pusillus, Meripilus giganteus, Exidia glandulosa, Xylaria hypoxylon, Trichophaea saccata, Acremonium* sp., *Chaetomium* sp., *Chaetomidium pingtungium, Myceliophthora thermophila, Myceliophthora hinnulea, Sporotrichum pruinosum, Thielavia* cf. *microspora, Aspergillus* sp., *Scopulariopsis* sp., *Fusarium* sp., *Verticillium* sp., *Pseudoplectania nigrella*, or *Phytophthora infestans* polypeptide.

In a more preferred embodiment, the polypeptide is a *Acremonium thermophilum, Chaetomium thermophilum, Scytalidium* sp., *Scytalidium thermophilum, Thermoascus aurantiacus, Thielavia australiensis, Verticillium tenerum, Neotermes castaneus, Melanocarpus albomyces, Poitrasia circinans*, or *Coprinus cinereus* polypeptide, e.g., the polypeptide consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), China General Microbiological Culture Collection Center (CGMCC), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, water, plants, animals, etc.) using the above-mentioned probes. Techniques for isolating microorganisms from natural habitats are well known in the art. The nucleotide sequence may then be derived by similarly screening a genomic or cDNA library of another microorganism. Once a nucleotide sequence encoding a polypeptide has been detected with the probe(s), the sequence may be isolated or cloned by utilizing techniques which are known to those of ordinary skill in the art (see, e.g., Sambrook et al., 1989, supra).

Polypeptides encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. In a preferred embodiment, the nucleotide sequence is selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65. In a more preferred embodiment, the nucleotide sequence is the mature polypeptide coding region contained in a plasmid which is contained in a deposited microorganism selected from the group consisting of CGMCC No. 0584, CGMCC No. 0581, CGMCC No. 0585, CGMCC No. 0582, CGMCC No. 0583, CGMCC No. 0580, CBS 109513, DSM 14348, DSM 15064, DSM 15065, DSM 15066, DSM 15067, CGMCC No. 0747, CGMCC No. 0748, CGMCC No. 0749, and CGMCC No. 0750. The present invention also encompasses polynucleotides comprising, preferably consisting of, nucleotide sequences which encode a polypeptide consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66, which differ from a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65 by virtue of the degeneracy of the genetic code.

The present invention also relates to polynucleotides comprising, preferably consisting of, a subsequence of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65 which encode fragments of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66 that have cellobiohydrolase I activity. A subsequence of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65 is a nucleotide sequence encompassed by a sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65 except that one or more nucleotides from the 5' and/or 3' end have been deleted.

The present invention also relates to polynucleotides having, preferably consisting of, a modified nucleotide sequence which comprises at least one modification in the mature polypeptide coding sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, and SEQ ID NO:65, and where the modified nucleotide sequence encodes a polypeptide which consists of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66.

The techniques used to isolate or clone a nucleotide sequence encoding a polypeptide are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a strain selected from the group consisting of *Acremonium, Scytalidium, Thermoascus, Thielavia, Verticillium, Neotermes, Melanocarpus, Poitrasia, Coprinus, Trichothecium, Humicola, Cladorrhinum, Diplodia, Myceliophthora, Rhizomucor, Meripilus, Exidia, Xylaria, Trichophaea, Chaetomium, Chaetomidium, Sporotrichum, Thielavia, Aspergillus, Scopulariopsis, Fusarium, Pseudoplectania,* and *Phytophthora,* or another or related organism and thus, for example, may be an allelic or species variant of the polypeptide encoding region of the nucleotide sequence.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

The present invention also relates to a polynucleotide comprising, preferably consisting of, a nucleotide sequence which has a degree of identity with a nucleotide sequence selected from the group consisting of
nucleotides 1 to 1578 of SEQ ID NO:1,
nucleotides 1 to 1587 of SEQ ID NO:3,
nucleotides 1 to 1353 of SEQ ID NO:5,
nucleotides 1 to 1371 of SEQ ID NO:7,
nucleotides 1 to 1614 of SEQ ID NO:9,
nucleotides 1 to 1245 of SEQ ID NO:11,
nucleotides 1 to 1341 of SEQ ID NO:13,
nucleotides 1 to 1356 of SEQ ID NO:15,
nucleotides 1 to 1365 of SEQ ID NO:37,
nucleotides 1 to 1377 of SEQ ID NO:39,
nucleotides 1 to 1353 of SEQ ID NO:41,
nucleotides 1 to 1341 of SEQ ID NO:43,
nucleotides 1 to 1584 of SEQ ID NO:45,
nucleotides 1 to 1368 of SEQ ID NO:47,
nucleotides 1 to 1395 of SEQ ID NO:49,
nucleotides 1 to 1383 of SEQ ID NO:51,
nucleotides 1 to 1353 of SEQ ID NO:53,
nucleotides 1 to 1599 of SEQ ID NO:55,
nucleotides 1 to 1383 of SEQ ID NO:57,
nucleotides 1 to 1578 of SEQ ID NO:59,
nucleotides 1 to 1371 of SEQ ID NO:65,
nucleotides 1 to 500 of SEQ ID NO:1,
nucleotides 1 to 500 of SEQ ID NO:3,
nucleotides 1 to 500 of SEQ ID NO:5,
nucleotides 1 to 500 of SEQ ID NO:7, nucleotides 1 to 500 of SEQ ID NO:9,
nucleotides 1 to 500 of SEQ ID NO:11,
nucleotides 1 to 500 of SEQ ID NO:13,
nucleotides 1 to 500 of SEQ ID NO:15,
nucleotides 1 to 500 of SEQ ID NO:37,
nucleotides 1 to 500 of SEQ ID NO:39,
nucleotides 1 to 500 of SEQ ID NO:41,
nucleotides 1 to 500 of SEQ ID NO:43,
nucleotides 1 to 500 of SEQ ID NO:45,
nucleotides 1 to 500 of SEQ ID NO:47,
nucleotides 1 to 500 of SEQ ID NO:49,
nucleotides 1 to 500 of SEQ ID NO:51,
nucleotides 1 to 500 of SEQ ID NO:53,
nucleotides 1 to 500 of SEQ ID NO:55,
nucleotides 1 to 500 of SEQ ID NO:57,
nucleotides 1 to 500 of SEQ ID NO:59,
nucleotides 1 to 500 of SEQ ID NO:65,
nucleotides 1 to 221 of SEQ ID NO:17,
nucleotides 1 to 239 of SEQ ID NO:18,
nucleotides 1 to 199 of SEQ ID NO:19,
nucleotides 1 to 191 of SEQ ID NO:20,
nucleotides 1 to 232 of SEQ ID NO:21,
nucleotides 1 to 467 of SEQ ID NO:22,
nucleotides 1 to 534 of SEQ ID NO:23,
nucleotides 1 to 563 of SEQ ID NO:24,
nucleotides 1 to 218 of SEQ ID NO:25,
nucleotides 1 to 492 of SEQ ID NO:26,
nucleotides 1 to 481 of SEQ ID NO:27,
nucleotides 1 to 463 of SEQ ID NO:28,
nucleotides 1 to 513 of SEQ ID NO:29,
nucleotides 1 to 579 of SEQ ID NO:30,
nucleotides 1 to 514 of SEQ ID NO:31,
nucleotides 1 to 477 of SEQ ID NO:32,
nucleotides 1 to 500 of SEQ ID NO:33,
nucleotides 1 to 470 of SEQ ID NO:34,
nucleotides 1 to 491 of SEQ ID NO:35,
nucleotides 1 to 221 of SEQ ID NO:36,
nucleotides 1 to 519 of SEQ ID NO:61,
nucleotides 1 to 497 of SEQ ID NO:62,
nucleotides 1 to 498 of SEQ ID NO:63,
nucleotides 1 to 525 of SEQ ID NO:64, and
nucleotides 1 to 951 of SEQ ID NO:67
of at least 70% identity, such as at least 75% identity; preferably, the nucleotide sequence has at least 80% identity, e.g., at least 85% identity, such as at least 90% identity, more preferably at least 95% identity, such as at least 96% identity, e.g., at least 97% identity, even more preferably at least 98% identity, such as at least 99%. Preferably, the nucleotide sequence encodes a polypeptide having cellobiohydrolase I activity. The degree of identity between two nucleotide sequences is determined as described previously (see the section entitled "Definitions").

In another interesting aspect, the present invention relates to a polynucleotide having, preferably consisting of, a nucleotide sequence which has at least 65% identity with the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CGMCC No. 0580, CBS 109513, DSM 14348, DSM 15064, DSM 15065, DSM 15066, DSM 15067, CGMCC No. 0747, CGMCC No. 0748, CGMCC No. 0749, and CGMCC No. 0750. In a preferred embodiment, the degree of identity with the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CGMCC No. 0580, CBS 109513, DSM 14348, DSM 15064, DSM 15065, DSM 15066, DSM 15067, CGMCC No. 0747, CGMCC No. 0748, CGMCC No. 0749, and CGMCC No. 0750 is at least 70%, e.g., at least 80%, such as at least 90%, more preferably at least 95%, such as at least 96%, e.g., at least 97%, even more preferably at least 98%, such as at least 99%. Preferably, the nucleotide sequence comprises the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CGMCC No. 0580, CBS 109513, DSM 14348, DSM 15064, DSM 15065, DSM 15066, DSM 15067, CGMCC No. 0747, CGMCC No. 0748, CGMCC No. 0749, and CGMCC No. 0750. In an even more preferred embodiment, the nucleotide sequence consists of the cellobiohydrolase I encoding part of the nucleotide sequence inserted into a plasmid present in a deposited microorganism selected from the group consisting of CGMCC No. 0584, CGMCC No. 0581, CGMCC No. 0585, CGMCC No. 0582, CGMCC No. 0583, CGMCC No. 0580, CBS 109513, DSM 14348, DSM 15064, DSM 15065, DSM 15066, DSM 15067, CGMCC No. 0747, CGMCC No. 0748, CGMCC No. 0749, and CGMCC No. 0750.

Modification of a nucleotide sequence encoding a polypeptide of the present invention may be necessary for the synthesis of a polypeptide, which comprises an amino acid sequence that has at least one substitution, deletion and/or insertion as compared to an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:66. These artificial variants may differ in some engineered way from the polypeptide isolated from its native source, e.g., variants that differ in specific activity, thermostability, pH optimum, or the like.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for cellobiohydrolase I activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, *Protein Expression and Purification* 2: 95-107.

The present invention also relates to a polynucleotide comprising, preferably consisting of, a nucleotide sequence which encodes a polypeptide having cellobiohydrolase I activity, and which hybridizes under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of (i) the complementary strand of the nucleotides selected from the group consisting of:
nucleotides 1 to 1578 of SEQ ID NO:1,
nucleotides 1 to 1302 of SEQ ID NO:1,
nucleotides 1 to 1587 of SEQ ID NO:3,
nucleotides 1 to 1302 of SEQ ID NO:3,
nucleotides 1 to 1353 of SEQ ID NO:5,
nucleotides 1 to 1302 of SEQ ID NO:5,
nucleotides 1 to 1371 of SEQ ID NO:7,
nucleotides 1 to 1302 of SEQ ID NO:7,
nucleotides 1 to 1614 of SEQ ID NO:9,
nucleotides 1 to 1302 of SEQ ID NO:9,
nucleotides 1 to 1245 of SEQ ID NO:11,
nucleotides 1 to 1341 of SEQ ID NO:13,
nucleotides 1 to 1302 of SEQ ID NO:13,
nucleotides 1 to 1356 of SEQ ID NO:15,
nucleotides 1 to 1302 of SEQ ID NO:15,
nucleotides 1 to 1365 of SEQ ID NO:37,
nucleotides 1 to 1302 of SEQ ID NO:37,
nucleotides 1 to 1377 of SEQ ID NO:39,
nucleotides 1 to 1302 of SEQ ID NO:39,
nucleotides 1 to 1353 of SEQ ID NO:41,
nucleotides 1 to 1302 of SEQ ID NO:41,
nucleotides 1 to 1341 of SEQ ID NO:43,
nucleotides 1 to 1302 of SEQ ID NO:43,
nucleotides 1 to 1584 of SEQ ID NO:45,
nucleotides 1 to 1302 of SEQ ID NO:45,
nucleotides 1 to 1368 of SEQ ID NO:47,
nucleotides 1 to 1302 of SEQ ID NO:47,
nucleotides 1 to 1395 of SEQ ID NO:49,
nucleotides 1 to 1302 of SEQ ID NO:49,
nucleotides 1 to 1383 of SEQ ID NO:51,
nucleotides 1 to 1302 of SEQ ID NO:51,
nucleotides 1 to 1353 of SEQ ID NO:53,
nucleotides 1 to 1302 of SEQ ID NO:53,
nucleotides 1 to 1599 of SEQ ID NO:55,
nucleotides 1 to 1302 of SEQ ID NO:55,
nucleotides 1 to 1383 of SEQ ID NO:57,
nucleotides 1 to 1302 of SEQ ID NO:57,
nucleotides 1 to 1578 of SEQ ID NO:59,
nucleotides 1 to 1302 of SEQ ID NO:59,
nucleotides 1 to 1371 of SEQ ID NO:65, and
nucleotides 1 to 1302 of SEQ ID NO:65;

(ii) the complementary strand of the nucleotides selected from the group consisting of:
nucleotides 1 to 500 of SEQ ID NO:1,
nucleotides 1 to 500 of SEQ ID NO:3,
nucleotides 1 to 500 of SEQ ID NO:5,
nucleotides 1 to 500 of SEQ ID NO:7,
nucleotides 1 to 500 of SEQ ID NO:9,
nucleotides 1 to 500 of SEQ ID NO:11,
nucleotides 1 to 500 of SEQ ID NO:13,
nucleotides 1 to 500 of SEQ ID NO:15,
nucleotides 1 to 500 of SEQ ID NO:37,
nucleotides 1 to 500 of SEQ ID NO:39,
nucleotides 1 to 500 of SEQ ID NO:41,
nucleotides 1 to 500 of SEQ ID NO:43,
nucleotides 1 to 500 of SEQ ID NO:45,
nucleotides 1 to 500 of SEQ ID NO:47,
nucleotides 1 to 500 of SEQ ID NO:49,
nucleotides 1 to 500 of SEQ ID NO:51,
nucleotides 1 to 500 of SEQ ID NO:53,
nucleotides 1 to 500 of SEQ ID NO:55,
nucleotides 1 to 500 of SEQ ID NO:57,
nucleotides 1 to 500 of SEQ ID NO:59,
nucleotides 1 to 500 of SEQ ID NO:65,
nucleotides 1 to 221 of SEQ ID NO:17,
nucleotides 1 to 239 of SEQ ID NO:18,
nucleotides 1 to 199 of SEQ ID NO:19,
nucleotides 1 to 191 of SEQ ID NO:20,
nucleotides 1 to 232 of SEQ ID NO:21,
nucleotides 1 to 467 of SEQ ID NO:22,
nucleotides 1 to 534 of SEQ ID NO:23,
nucleotides 1 to 563 of SEQ ID NO:24,
nucleotides 1 to 218 of SEQ ID NO:25,
nucleotides 1 to 492 of SEQ ID NO:26,
nucleotides 1 to 481 of SEQ ID NO:27,
nucleotides 1 to 463 of SEQ ID NO:28,
nucleotides 1 to 513 of SEQ ID NO:29,
nucleotides 1 to 579 of SEQ ID NO:30,
nucleotides 1 to 514 of SEQ ID NO:31,
nucleotides 1 to 477 of SEQ ID NO:32,
nucleotides 1 to 500 of SEQ ID NO:33,
nucleotides 1 to 470 of SEQ ID NO:34,
nucleotides 1 to 491 of SEQ ID NO:35,
nucleotides 1 to 221 of SEQ ID NO:36,
nucleotides 1 to 519 of SEQ ID NO:61,
nucleotides 1 to 497 of SEQ ID NO:62,
nucleotides 1 to 498 of SEQ ID NO:63,
nucleotides 1 to 525 of SEQ ID NO:64, and
nucleotides 1 to 951 of SEQ ID NO:67; and (iii) the complementary strand of the nucleotides selected from the group consisting of:
nucleotides 1 to 200 of SEQ ID NO:1,
nucleotides 1 to 200 of SEQ ID NO:3,
nucleotides 1 to 200 of SEQ ID NO:5,
nucleotides 1 to 200 of SEQ ID NO:7,
nucleotides 1 to 200 of SEQ ID NO:9,
nucleotides 1 to 200 of SEQ ID NO:11,
nucleotides 1 to 200 of SEQ ID NO:13,
nucleotides 1 to 200 of SEQ ID NO:15,
nucleotides 1 to 200 of SEQ ID NO:37,
nucleotides 1 to 200 of SEQ ID NO:39,
nucleotides 1 to 200 of SEQ ID NO:41,
nucleotides 1 to 200 of SEQ ID NO:43,
nucleotides 1 to 200 of SEQ ID NO:45, nucleotides 1 to 200 of SEQ ID NO:47,
nucleotides 1 to 200 of SEQ ID NO:49,
nucleotides 1 to 200 of SEQ ID NO:51,
nucleotides 1 to 200 of SEQ ID NO:53,
nucleotides 1 to 200 of SEQ ID NO:55,
nucleotides 1 to 200 of SEQ ID NO:57,
nucleotides 1 to 200 of SEQ ID NO:59,
nucleotides 1 to 200 of SEQ ID NO:65,
nucleotides 1 to 200 of SEQ ID NO:22,
nucleotides 1 to 200 of SEQ ID NO:23,
nucleotides 1 to 200 of SEQ ID NO:24,
nucleotides 1 to 200 of SEQ ID NO:26,
nucleotides 1 to 200 of SEQ ID NO:27,
nucleotides 1 to 200 of SEQ ID NO:28,
nucleotides 1 to 200 of SEQ ID NO:29,
nucleotides 1 to 200 of SEQ ID NO:30,
nucleotides 1 to 200 of SEQ ID NO:31,
nucleotides 1 to 200 of SEQ ID NO:32,
nucleotides 1 to 200 of SEQ ID NO:33,
nucleotides 1 to 200 of SEQ ID NO:34,
nucleotides 1 to 200 of SEQ ID NO:35,
nucleotides 1 to 200 of SEQ ID NO:61,
nucleotides 1 to 200 of SEQ ID NO:62,
nucleotides 1 to 200 of SEQ ID NO:63,
nucleotides 1 to 200 of SEQ ID NO:64, and
nucleotides 1 to 200 of SEQ ID NO:67.

As will be understood, details and particulars concerning hybridization of the nucleotide sequences will be the same or analogous to the hybridization aspects discussed in the section entitled "Polypeptides Having Cellobiohydrolase I Activity" herein.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

In an even more preferred embodiment, the yeast host cell is a *Candida*, *Aschbyii*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, 194: 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is selected from the group consisting of *Acremonium, Scytalidium, Thermoascus, Thielavia, Verticillium, Neotermes, Melanocarpus, Poitrasia, Coprinus, Trichothecium, Humicola, Cladorrhinum, Diplodia, Myceliophthora, Rhizomucor, Meripilus, Exidia, Xylaria, Trichophaea, Chaetomium, Chaetomidium, Sporotrichum, Thielavia, Aspergillus, Scopulariopsis, Fusarium, Pseudoplectania*, and *Phytophthora*; more preferably the strain is selected from the group consisting of *Acremonium thermophilum, Chaetomium thermophilum, Scytalidium thermophilum, Thermoascus aurantiacus, Thielavia australiensis, Verticillium tenerum, Neotermes castaneus, Melanocarpus albomyces, Poitrasia circinans, Coprinus cinereus, Trichothecium roseum, Humicola nigrescens, Cladorrhinum foecundissimum, Diplodia gossypina, Myceliophthora thermophila, Rhizomucor pusillus, Meripilus giganteus, Exidia glandulosa, Xylaria hypoxylon, Trichophaea saccata, Chaetomidium pingtungium, Myceliophthora thermophila, Myceliophthora hinnulea, Sporotrichum pruinosum, Thielavia* cf. microspora, *Pseudoplectania nigrella*, and *Phytophthora infestans*.

The present invention also relates to methods for producing a polypeptide of the present invention comprising (a) cultivating a host cell under conditions conducive for production of the polypeptide; and (b) recovering the polypeptide.

The present invention also relates to methods for in-situ production of a polypeptide of the present invention comprising (a) cultivating a host cell under conditions conducive for production of the polypeptide; and (b) contacting the polypeptide with a desired substrate, such as a cellulosic substrate, without prior recovery of the polypeptide. The term "in-situ production" is intended to mean that the polypeptide is produced directly in the locus in which it is intended to be used, such as in a fermentation process for production of ethanol.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having cellobiohydrolase I activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, millets, and maize (corn).

Examples of dicot plants are tobacco, lupins, potato, sugar beet, legumes, such as pea, bean and soybean, and cruciferous plants (family Brassicaceae), such as cauliflower, rape, canola, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny (clonal or seed) of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleotide sequence encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleotide sequence encoding a polypeptide having cellobiohydrolase I activity of the present invention under conditions conducive for production of the polypeptide; and (b) recovering the polypeptide.

The present invention also relates to methods for in-situ production of a polypeptide of the present invention comprising (a) cultivating a transgenic plant or a plant cell comprising a nucleotide sequence encoding a polypeptide having cellobiohydrolase I activity of the present invention under conditions conducive for production of the polypeptide; and (b) contacting the polypeptide with a desired substrate, such as a cellulosic substrate, without prior recovery of the polypeptide.

Compositions

In a still further aspect, the present invention relates to compositions comprising a polypeptide of the present invention.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Compositions

The polypeptide of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptide of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the polypeptide of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptide of the invention may additionally be incorporated in the detergent formulations disclosed in WO 97/07202 which is hereby incorporated as reference.

DNA Recombination (Shuffling)

The nucleotide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:62, SEQ ID NO:63, SEQ ID NO:64, SEQ ID NO:65, SEQ ID NO:67 may be used in a DNA recombination (or shuffling) process. The new polynucleotide sequences obtained in such a process may encode new polypeptides having cellobiase activity with improved properties, such as improved stability (storage stability, thermostability), improved specific activity, improved pH-optimum, and/or improved tolerance towards specific compounds.

Shuffling between two or more homologous input polynucleotides (starting-point polynucleotides) involves fragmenting the polynucleotides and recombining the fragments, to obtain output polynucleotides (i.e., polynucleotides that have been subjected to a shuffling cycle) wherein a number of nucleotide fragments are exchanged in comparison to the input polynucleotides.

DNA recombination or shuffling may be a (partially) random process in which a library of chimeric genes is generated from two or more starting genes. A number of known formats can be used to carry out this shuffling or recombination process.

The process may involve random fragmentation of parental DNA followed by reassembly by PCR to new full-length genes, e.g., as presented in U.S. Pat. Nos. 5,605,793, 5,811, 238, 5,830,721, 6,117,679. In-vitro recombination of genes may be carried out, e.g., as described in U.S. Pat. Nos. 6,159, 687, 6,159,688, 5,965,408, 6,153,510, and WO 98/41623. The recombination process may take place in vivo in a living cell, e.g., as described in WO 97/07205 and WO 98/28416.

The parental DNA may be fragmented by DNA'se I treatment or by restriction endonuclease digests as described by Kikuchi et al (2000a, Gene 236:159-167). Shuffling of two parents may be done by shuffling single stranded parental DNA of the two parents as described in Kikuchi et al (2000b, *Gene* 243:133-137).

A particular method of shuffling is to follow the methods described in Crameri et al, 1998, *Nature* 391: 288-291 and Ness et al., *Nature Biotechnology* 17: 893-896. Another format would be the methods described in U.S. Pat. No. 6,159, 687: Examples 1 and 2.

Production of Ethanol from Biomass

The present invention also relates to methods for producing ethanol from biomass, such as cellulosic materials, comprising contacting the biomass with the polypeptides of the invention. Ethanol may subsequently be recovered. The polypeptides of the invention may be produced "in-situ", i.e., as part of, or directly in an ethanol production process, by cultivating a host cell or a strain, which in its wild-type form is capable of producing the polypeptides, under conditions conducive for production of the polypeptides.

Ethanol can be produced by enzymatic degradation of biomass and conversion of the released polysaccharides to ethanol. This kind of ethanol is often referred to as bioethanol or biofuel. It can be used as a fuel additive or extender in blends of from less than 1% and up to 100% (a fuel substitute). In some countries, such as Brazil, ethanol is substituting gasoline to a very large extent.

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of cellulase enzymes are used to breakdown biomass:
- The "endo-1,4-beta-glucanases" or 1,4-beta-D-glucan-4-glucanohydrolases (EC 3.2.1.4), which act randomly on soluble and insoluble 1,4-beta-glucan substrates.
- The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and 1,4-beta-D-glucan cellobiohydrolase (EC 3.2.1.91), also referred to as cellobiohydrolase I, which liberates D-cellobiose from 1,4-beta-glucans.
- The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically in a complex interplay that results in efficient decrystallization and hydrolysis of native cellulose from biomass to yield the reducing sugars which are converted to ethanol by fermentation.

The present invention is further described by the following examples which should not be construed as limiting the scope of the invention.

EXAMPLES

Chemicals used as buffers and substrates were commercial products of at least reagent grade.

Example 1

Cloning of a Partial and a Full-Length Cellobiohydrolase I (CBH1) DNA Sequence

A cDNA library of *Diplodia* gossypina was PCR screened for presence of the CBH1 gene. For this purpose sets of primers were constructed, based on sequence alignment and identification of conserved regions among CBH1 proteins. The PCR band from a gel electrophoresis was used to obtain a partial sequence of the CBH1 gene from *Diplodia gossypina*. Homology search confirmed that the partial sequence was a partial sequence of the CBH1 gene (EC 3.2.1.91).

The full-length CBH1 gene of *Diplodia gossypina* is obtained by accessing the patent deposit CBS 247.96, make a DNA or cDNA preparation, use the partial sequence as basis for construction of specific primers, and use standard PCR cloning techniques to step by step getting the entire gene.

Several other approaches can be taken:

- PCR screening of the cDNA library or the cDNAs that were used for the construction of the library, could be performed. To do so, Gene Specific Primers (GSP) and vector/adaptor primers are constructed from the partial cDNA sequence of the CBH1 gene and from vector/adaptor sequence respectively; both sets of primers designed to go outward into the missing 5' and 3' regions of the CBH1 cDNA. The longest PCR products obtained using combinations of GSP and vector/adaptor primer represent the full-length 5' and 3' end regions of the CBH1 cDNA from *Diplodia gossypina*. Homology search and comparison with the partial cDNA sequence confirm that the 5' and 3' PCR products belong to the same CBH1 cDNA from *Diplodia gossypina*. The full-length cDNA can then be obtained by PCR using a set of primers constructed from both the 5' and 3' ends.
- Alternatively, the cDNA library could be screened for the full-length cDNA using standard hybridization techniques and the partial cDNA sequence as a probe. The clones giving a positive hybridization signal with the probe are then purified and sequenced to determine the longest cDNA sequence. Homology search and comparison confirms that the full-length cDNA correspond to the partial CBH1 cDNA sequence that was originally used as a probe.

The two approaches described above rely on the presence of the full-length CBH1 cDNA in the cDNA library or in the cDNAs used for its construction. Alternatively, the 5' and 3' RACE (Rapid Amplification of cDNA Ends) techniques or derived techniques could be used to identify the missing 5' and 3' regions. For this purpose, preferably mRNAs from *Diplodia gossipina* are isolated and utilized to synthesize first strand cDNAs using oligo(dT)-containing Adapter Primer or a 5'-Gene Specific Primer (GSP).

The full-length cDNA of the CBH1 gene from *Diplodia gossypina* can also be obtained by using genomic DNA from *Diplodia gossypina*. The CBH1 gene can be identified by PCR techniques such as the one describe above or by standard genomic library screening using hybridization techniques and the partial CBH1 cDNA as a probe. Homology search and comparison with the partial CBH1 cDNA confirms that the genomic sequence correspond to the CBH1 gene from *Diplodia gossypina*. Identification of consensus sequences such as initiation site of transcription, start and stop codons or polyA sites could be used to define the region comprising the full-length cDNA. Primers constructed from both the 5' and 3' ends of this region could then be used to amplify the full-length cDNA from mRNA or cDNA library from *Diplodia gossypina* (see above).

By expression of the full-length gene in a suitable expression host construct the CBH1 enzyme is harvested as an intra cellular or extra cellular enzyme from the culture broth.

The methods described above apply to the cloning of cellobiohydrolase I DNA sequences from all organisms and not only *Diplodia gossypina.*

Example 2

Cellobiohydrolase I (CBH I) Activity

A cellobiohydrolase I is characterized by the ability to hydrolyze highly crystalline cellulose very efficiently compared to other cellulases. Cellobiohydrolase I may have a higher catalytic activity using PASO (phosphoric acid swollen cellulose) as substrate than using CMC as substrate. For the purposes of the present invention, any of the following assays can be used to identify a cellobiohydrolase I:

Activity on Azo-Avicel

Azo-Avicel (Megazyme, Bray Business Park, Bray, Wicklow, Ireland) was used according to the manufacturer's instructions.

Activity on PNP-beta-cellobiose

Substrate solution: 5 mM PNP beta-D-Cellobiose (p-Nitrophenyl β-d-Cellobioside Sigma N-5759) in 0.1 M Na-acetate buffer, pH 5.0;

Stop reagent: 0.1 M Na-carbonate, pH 11.5.

50 microliters CBH I solution was mixed with 1 mL substrate solution and incubated 20 minutes at 40° C. The reaction was stopped by addition of 5 mL stop reagent. Absorbance was measured at 404 nm.

Activity on PASC and CMC

The substrate is degraded with cellobiohydrolase I (CBH I) to form reducing sugars. A *Microdochium nivale* carbohydrate oxidase (rMnO) or another equivalent oxidase acts on the reducing sugars to form $H_2O_2$ in the presence of $O_2$. The formed $H_2O_2$ activates in the presence of excess peroxidase the oxidative condensation of 4-aminoantipyrine (AA) and N-ethyl-N-sulfopropyl-m-toluidine (TOPS) to form a purple product which can be quantified by its absorbance at 550 nm.

When all components except CBH I are in surplus, the rate of increase in absorbance is proportional to the CBH I activity. The reaction is a one-kinetic-step reaction and may be carried out automatically in a Cobas Fara centrifugal analyzer (Hoffmann La Roche) or another equivalent spectrophotometer which can measure steady state kinetics.

Buffer: 50 mM Na-acetate buffer (pH 5.0);

Reagents: rMnO oxidase, purified *Microdochium nivale* carbohydrate oxidase, 2 mg/L (final concentration);
Peroxidase, SIGMA P-8125 (96 U/mg), 25 mg/L (final concentration);
4-aminoantipyrine, SIGMA A-4382, 200 mg/L (final concentration);
TOPS, SIGMA E-8506, 600 mg/L (final concentration);
PASC or CMC (see below), 5 g/L (final concentration).

All reagents were added to the buffer in the concentrations indicated above and this reagent solution was mixed thoroughly.

50 microliters cellobiohydrolase I sample (in a suitable dilution) was mixed with 300 μL reagent solution and incubated 20 minutes at 40° C. Purple color formation was detected and measured as absorbance at 550 nm.

The AA/TOPS-condensate absorption coefficient is 0.01935 $A_{550}$/(microM cm). The rate is calculated as micromoles reducing sugar produced per minute from $OD_{550}$/minute and the absorption coefficient.

PASC:

Materials: 5 g Avicel® (Art. 2331 Merck);
150 mL 85% Ortho-phosphoric-acid (Art. 573 Merck);
800 mL Acetone (Art. 14 Merck);
Approx. 2 liter deionized water (Milli-Q);
1 L glass beaker;
1 L glass filter funnel;
2 L suction flask;
Ultra Turrax Homogenizer.

Acetone and ortho-phosphoric-acid is cooled on ice. Avicel® is moisted with water, and then the 150 mL icecold 85% Ortho-phosphoric-acid is added. The mixture is placed on an icebath with weak stirring for one hour.

Add 500 mL ice-cold acetone with stirring, and transfer the mixture to a glass filter funnel and wash with 3×100 mL ice-cold acetone, suck as dry as possible in each wash. Wash with 2×500 mL water (or until there is no odor of acetone), suck as dry as possible in each wash.

Re-suspend the solids in water to a total volume of 500 mL, and blend to homogeneity using an Ultra Turrax Homogenizer. Store wet in refrigerator and equilibrate with buffer by centrifugation and re-suspension before use.

CMC:

Bacterial cellulose microfibrils in an impure form were obtained from the Japanese foodstuff "nata de coco" (Fujico Company, Japan). The cellulose in 350 g of this product was purified by suspension of the product in about 4 L of tap water. This water was replaced by fresh water twice a day for 4 days.

Then 1% (w/v) NaOH was used instead of water and the product was re-suspended in the alkali solution twice a day for 4 days. Neutralisation was done by rinsing the purified cellulose with distilled water until the pH at the surface of the product was neutral (pH 7).

The cellulose was microfibrillated and a suspension of individual bacterial cellulose microfibrils was obtained by homogenisation of the purified cellulose microfibrils in a Waring blender for 30 min. The cellulose microfibrils were further purified by dialysing this suspension through a pore membrane against distilled water and the isolated and purified cellulose microfibrils were stored in a water suspension at 4° C.

Deposit of Biological Material

China General Microbiological Culture Collection Center (CGMCC)

The following biological material has been deposited under the terms of the Budapest Treaty with the China General Microbiological Culture Collection Center (CGMCC), Institute of Microbiology, Chinese Academy of Sciences, Haidian, Beijing 100080, China:

Accession Number: CGMCC No. 0584
Applicants reference: ND000575
Date of Deposit: May 29, 2001
Description: *Acremonium thermophilum* CBH I gene on plasmid
Classification: Ascomycota; Sordariomycetes; Hypocrales; Hypocreaceae
Origin: China, 1999
Related sequence(s): SEQ ID NO:1 and SEQ ID NO:2 (DNA sequence encoding a cellobiohydrolase I from *Acremonium thermophilum* and the corresponding protein sequence)

Accession Number: CGMCC No. 0581
Applicants reference: ND000548
Date of Deposit: May 29, 2001
Description: *Chaetomium thermophilum* CBH I gene on plasmid
Classification: Ascomycota; Sordariomycetes; Sordariales; Chaetomiaceae
Origin: China, 1999
Related sequence(s): SEQ ID NO:3 and SEQ ID NO:4 (DNA sequence encoding a cellobiohydrolase I from *Chaetomium thermophilum* and the corresponding protein sequence)

Accession Number: CGMCC No. 0585
Applicants reference: ND001223
Date of Deposit: May 29, 2001
Description: *Scytalidium* sp. CBH I gene on plasmid
Classification: Ascomycota; Mitosporic
Origin: China, 1999
Related sequence(s): SEQ ID NO:5 and SEQ ID NO:6 (DNA sequence encoding a cellobiohydrolase I from *Scytalidium* sp. and the corresponding protein sequence)

Accession Number: CGMCC No. 0582

Applicants reference: ND000549
Date of Deposit: May 29, 2001
Description: *Thermoascus aurantiacus* CBH I gene on plasmid
Classification: Eurotiomycetes; Eurotiales; Trichocomaceae
Origin: China
Related sequence(s): SEQ ID NO:7 and SEQ ID NO:8 (DNA sequence encoding a cellobiohydrolase I from *Thermoascus aurantiacus* and the corresponding protein sequence)
Accession Number: CGMCC No. 0583
Applicants reference: ND001182
Date of Deposit: May 29, 2001
Description: *Thielavia australiensis* CBH I gene on plasmid
Classification: Ascomycota; Sordariomycetes; Sordariales; Chaetomiaceae
Origin: China, 1998
Related sequence(s): SEQ ID NO:9 and SEQ ID NO:10 (DNA sequence encoding a cellobiohydrolase I from *Thielavia* australiensis and the corresponding protein sequence)
Accession Number: CGMCC No. 0580
Applicants reference: ND000562
Date of Deposit: May 29, 2001
Description: *Melanocarpus albomyces* CBH I gene on plasmid
Classification: Ascomycota; Sordariomycetes; Sordariales
Origin: China, 1999
Related sequence(s): SEQ ID NO:15 and SEQ ID NO:16 (DNA sequence encoding a cellobiohydrolase I from *Melanocarpus albomyces* and the corresponding protein sequence)
Accession Number: CGMCC No. 0748
Applicants reference: ND001181
Date of Deposit: Jun. 7, 2002
Description: *Acremonium* sp. CBH I gene on plasmid
Classification: mitosporic Ascomycetes
Origin: China, 2000
Related sequence(s): SEQ ID NO:53 and SEQ ID NO:54
Accession Number: CGMCC No. 0749
Applicants reference: ND000577
Date of Deposit: Jun. 7, 2002
Description: *Aspergillus fumigatus* CBH I gene on plasmid
Classification: Trichocomaceae, Eurotiales, Ascomycota (Teleomorph: Neosartorya fumigata)
Origin: China, 2000
Related sequence(s): SEQ ID NO:55 and SEQ ID NO:56
Accession Number: CGMCC No. 0747
Applicants reference: ND001175
Date of Deposit: Jun. 7, 2002
Description: *Sporotrichum pruinosum* CBH I gene on plasmid
Classification: Meruliaceae, Stereales, Basidiomycota
Origin: China, 2000
Related sequence(s): SEQ ID NO:57 and SEQ ID NO:58
Accession Number: CGMCC No. 0750
Applicants reference: ND000571
Date of Deposit: Jun. 7, 2002
Description: *Scytalidium thermophilum* CBH I gene on plasmid
Classification: Ascomycota; Mitosporic
Origin: China, 2000
Related sequence(s): SEQ ID NO:59 and SEQ ID NO:60
Centraalbureau Voor Schimmelcultures (CBS)

The following biological material has been deposited under the terms of the Budapest Treaty with the Centraalbureau Voor Schimmelcultures (CBS), Uppsalalaan 8, 3584 CT Utrecht, The Netherlands (alternatively P.O. Box 85167, 3508 AD Utrecht, The Netherlands):
Accession Number: CBS 109513
Applicants reference: ND000538
Date of Deposit: Jun. 1, 2001
Description: *Verticillium tenerum*
Classification: Ascomycota, Hypocreales, Pyrenomycetes (mitosporic)
Origin: -
Related sequence(s): SEQ ID NO:11 and SEQ ID NO:12 (DNA sequence encoding a cellobiohydrolase I from *Verticillium tenerum* and the corresponding protein sequence)
Accession Number: CBS 819.73
Applicants reference: ND000533
Date of Deposit: Publicly available (not deposited by applicant)
Description: *Humicola* nigrescens
Classification: Sordariaceae, Sordariales, Sordariomycetes; Ascomycota
Origin: -
Related sequence(s): SEQ ID NO:18 (partial DNA sequence encoding a cellobiohydrolase I from *Humicola nigrescens*)
Accession Number: CBS 427.97
Applicants reference: ND000530
Date of Deposit: Jan. 23, 1997
Description: *Cladorrhinum foecundissimum*
Classification: Sordariaceae, Sordariales, Sordariomycetes; Ascomycota
Origin: Jamaica
Related sequence(s): SEQ ID NO:19 (partial DNA sequence encoding a cellobiohydrolase I from *Cladorrhinum foecundissimum*)
Accession Number: CBS 247.96
Applicants reference: ND000534 and ND001231
Date of Deposit: Mar. 12, 1996
Description: *Diplodia gossypina*
Classification: Dothideaceae, Dothideales, Dothidemycetes; Ascomycota
Origin: Indonesia, 1992
Related sequence(s): SEQ ID NO:20 (partial DNA sequence encoding a cellobiohydrolase I from *Diplodia* gossypina), SEQ ID NO:37 (full DNA sequence encoding a cellobiohydrolase I from *Diplodia* gossypina) and SEQ ID NO:38 (full cellobiohydrolase I protein sequence from *Diplodia* gossypina)
Accession Number: CBS 117.65
Applicants reference: ND000536
Date of Deposit: Publicly available
Description: *Myceliophthora thermophila*
Classification: Sordariaceae, Sordariales, Sordariomycetes; Ascomycota
Origin:
Related sequence(s): SEQ ID NO:21 (partial DNA sequence encoding a cellobiohydrolase I from *Myceliophthora thermophila*)
Accession Number: CBS 109471
Applicants reference: ND000537
Date of Deposit: May 29, 2001
Description: *Rhizomucor pusillus*
Classification: Mucoraceae, Mucorales, Zygomycota
Origin: Denmark
Related sequence(s): SEQ ID NO:22 (partial DNA sequence encoding a cellobiohydrolase I from *Rhizomucor pusillus*)
Accession Number: CBS 521.95
Applicants reference: ND000542
Date of Deposit: Jul. 4, 1995
Description: *Meripilus giganteus*

Classification: Rigidiporaceae, Hymenomycetales, Basidiomycota
Origin: Denmark, 1993
Related sequence(s): SEQ ID NO:23 (partial DNA sequence encoding a cellobiohydrolase I from *Meripilus giganteus*)
Accession Number: CBS 277.96
Applicants reference: ND000543, ND001346 and ND001243
Date of Deposit: Mar. 12, 1996
Description: *Exidia glandulosa*
Classification: Exidiaceae, Auriculariales, Hymenomycetes, Basidiomycota
Origin: Denmark, 1993
Related sequence(s): SEQ ID NO:24 (partial DNA sequence encoding a cellobiohydrolase I from *Exidia glandulosa*), SEQ ID NO:45 (full DNA sequence encoding a cellobiohydrolase I with CBD from *Exidia glandulosa*), SEQ ID NO:46 (full cellobiohydrolase I protein sequence with CBD from *Exidia glandulosa*), SEQ ID NO:47 (full DNA sequence encoding a cellobiohydrolase I from *Exidia glandulosa*) and SEQ ID NO:48 (full cellobiohydrolase I protein sequence from *Exidia glandulosa*)
Accession Number: CBS 284.96
Applicants reference: ND000544 and ND001235
Date of Deposit: Mar. 12, 1996
Description: *Xylaria hypoxylon*
Classification: Sordariaceae, Sordariales, Sordariomycetes, Ascomycota
Origin: Denmark, 1993
Related sequence(s): SEQ ID NO:25 (partial DNA sequence encoding a cellobiohydrolase I from *Xylaria hypoxylon*), SEQ ID NO:43 (full DNA sequence encoding a cellobiohydrolase I from *Xylaria hypoxylon*) and SEQ ID NO:44 (full cellobiohydrolase I protein sequence from *Xylaria hypoxylon*)
Accession Number: CBS 804.70
Applicants reference: ND001227
Date of Deposit: Publicly available
Description: *Trichophaea saccata*
Classification: Ascomycota; Pezizomycetes; Pezizales; Pyronemataceae
Related sequence(s): SEQ ID NO:36 (partial DNA sequence encoding a cellobiohydrolase I from *Trichophaea saccata*)
Deutsche Sammlunq von Mikroorganismen und Zellkulturen GmbH (DSMZ)

The following biological material has been deposited under the terms of the Budapest Treaty with the Deutsche Sammlung von Mikroorganismen und Zellkulturen GmbH (DSMZ), Mascheroder Weg 1b, 38124 Braunschweig, Germany:
Accession Number: DSM 14348
Applicants reference: ND000551
Date of Deposit: Jun. 13, 2001
Description: *Neotermes castaneus*, termite CBH I gene on plasmid
Classification: -
Origin: Cultures of termite larvae bought from BAM, Germany, 1999
Related sequence(s): SEQ ID NO:13 and SEQ ID NO:14 (DNA sequence encoding a cellobiohydrolase I from gut cells or microbes from the gut of *Neotermes castaneus* and the corresponding protein sequence)
Accession Number: DSM 15066
Applicants reference: ND001349
Date of Deposit: Jun. 21, 2002
Description: *Poitrasia circinans* CBH I gene on plasmid
Classification: Choanephoraceae, Zygomycota, Mucorales
Origin: -
Related sequence(s): SEQ ID NO:49 (DNA sequence encoding a cellobiohydrolase I from *Poitrasia circinans*) and SEQ ID NO:50 (cellobiohydrolase I protein sequence from *Poitrasia circinans*)
Accession Number: DSM 15065
Applicants reference: ND001339
Date of Deposit: Jun. 21, 2002
Description: *Coprinus cinereus* CBH I gene on plasmid
Classification: Basidiomycota, Hymenomycetes; Agaricales, Agaricaceae
Origin: Denmark
Related sequence(s): SEQ ID NO:51 (DNA sequence encoding a cellobiohydrolase I from *Coprinus cinereus*) and SEQ ID NO:52 (cellobiohydrolase I protein sequence from *Coprinus cinereus*)
Accession Number: DSM 15064
Applicants reference: ND001264
Date of Deposit: Jun. 21, 2002
Description: *Trichophaea saccata* CBH I gene on plasmid
Classification: Ascomycota; Pezizomycetes; Pezizales; Pyronemataceae
Origin: -
Related sequence(s): SEQ ID NO:39 (DNA sequence encoding a cellobiohydrolase I from *Trichophaea saccata*) and SEQ ID NO:40 (cellobiohydrolase I protein sequence from *Trichophaea saccata*)
Accession Number: DSM 15067
Applicants reference: ND001232
Date of Deposit: Jun. 21, 2002
Description: *Myceliophthora thermophila* CBH I gene on plasmid
Classification: Sordariaceae, Sordariales, Sordariomycetes; Ascomycota
Origin: -
Related sequence(s): SEQ ID NO:41 (DNA sequence encoding a cellobiohydrolase I from *Myceliophthora thermophila*) and SEQ ID NO:42 (cellobiohydrolase I protein sequence from *Myceliophthora thermophila*)
Institute for Fermentation, Osaka (IFO)

The following biological material has been deposited under the terms of the Budapest Treaty with the Institute for Fermentation, Osaka (IFO), 17-85, Juso-honmachi 2-chome, Yodogawa-ku, Osaka 532-8686, Japan:
Accession Number: IFO 5372
Applicants reference: ND000531
Date of Deposit: Publicly available (not deposited by applicant)
Description: *Trichothecium roseum*
Classification: mitosporic Ascomycetes
Origin:
Related sequence(s): SEQ ID NO:17 (partial DNA sequence encoding a cellobiohydrolase I from *Trichothecium roseum*)

The deposit of CBS 427.97, CBS 247.96, CBS 521.95, CBS 284.96, CBS 274.96 were made by Novo Nordisk NS and were later assigned to Novozymes NS.

The invention claimed is:

1. A nucleic acid construct comprising a polynucleotide encoding a polypeptide having cellobiohydrolase I activity, wherein the polynucleotide is operably linked to one or more heterologous control sequences that direct the production of the polypeptide in an expression host, and wherein the polypeptide comprises the sequence of amino acids 1 to 525 of SEQ ID NO: 60, or differs by at most three amino acids from the sequence of amino acids 1 to 525 of SEQ ID NO: 60.

2. The nucleic acid construct of claim 1, wherein the polypeptide having cellobiohydrolase I activity differs by at most three amino acids from the sequence of amino acids 1 to 525 of SEQ ID NO: 60.

3. The nucleic acid construct of claim 1, wherein the polypeptide having cellobiohydrolase I activity differs by three amino acids from the sequence of amino acids 1 to 525 of SEQ ID NO: 60.

4. The nucleic acid construct of claim 1, wherein the polypeptide having cellobiohydrolase I activity differs by at most two amino acids from the sequence of amino acids 1 to 525 of SEQ ID NO: 60.

5. The nucleic acid construct of claim 1, wherein the polypeptide having cellobiohydrolase I activity differs by two amino acids from the sequence of amino acids 1 to 525 of SEQ ID NO: 60.

6. The nucleic acid construct of claim 1, wherein the polypeptide having cellobiohydrolase I activity differs by one amino acid from the sequence of amino acids 1 to 525 of SEQ ID NO: 60.

7. The nucleic acid construct of claim 1, wherein the polypeptide having cellobiohydrolase I activity comprises the sequence of amino acids 1 to 525 of SEQ ID NO: 60.

8. The nucleic acid construct of claim 1, wherein the polypeptide having cellobiohydrolase I activity is a variant comprising a substitution, deletion, and/or insertion of one or more amino acids of amino acids 1 to 525 of SEQ ID NO: 60.

9. A recombinant expression vector comprising the nucleic acid construct of claim 1.

10. A recombinant host cell comprising the nucleic acid construct of claim claim 1.

11. A transgenic plant, plant part or plant cell transformed with the nucleic acid construct of claim 1.

12. A method of producing a polypeptide having cellobiohydrolase I activity, comprising: (a) cultivating the recombinant host cell of claim 10 under conditions conducive for production of the polypeptide; and (b) recovering the polypeptide.

13. The method of claim 12, wherein the polypeptide having cellobiohydrolase I activity comprises the sequence of amino acids 1 to 525 of SEQ ID NO: 60.

14. The method of claim 12, wherein the polypeptide having cellobiohydrolase I activity is a variant comprising a substitution, deletion, and/or insertion of one or more amino acids of amino acids 1 to 525 of SEQ ID NO: 60.

15. A method of producing a polypeptide having cellobiohydrolase I activity, comprising: (a) cultivating the transgenic plant or the plant cell of claim 11 under conditions conducive for production of the polypeptide; and (b) recovering the polypeptide.

16. The method of claim 15, wherein the polypeptide having cellobiohydrolase I activity comprises the sequence of amino acids 1 to 525 of SEQ ID NO: 60.

17. The method of claim 15, wherein the polypeptide having cellobiohydrolase I activity is a variant comprising a substitution, deletion, and/or insertion of one or more amino acids of amino acids 1 to 525 of SEQ ID NO: 60.

* * * * *

SEQUENCE LISTING

<160> NUMBER OF SEQ ID NOS: 67

<210> SEQ ID NO 1
<211> LENGTH: 1581
<212> TYPE: DNA
<213> ORGANISM: Thielavia terrestris
<220> FEATURE:
<221> NAME/KEY: CDS
<222> LOCATION: (1)..(1581)

<400> SEQUENCE: 1

| | | | | | | | | | | | | | | | | |
|---|---|---|---|---|---|---|---|---|---|---|---|---|---|---|---|---|
| atg | cac | gcc | aag | ttc | gcg | acc | ctc | gcc | gcc | ctt | gtg | gcg | tcc | gcc | gcg | 48 |
| Met | His | Ala | Lys | Phe | Ala | Thr | Leu | Ala | Ala | Leu | Val | Ala | Ser | Ala | Ala | |
| 1 | | | | 5 | | | | | 10 | | | | | 15 | | |

| gcc | cag | cag | gcc | tgc | aca | ctc | acg | gct | gag | aac | cac | ccc | acc | ctg | tcg | 96 |
|---|---|---|---|---|---|---|---|---|---|---|---|---|---|---|---|---|
| Ala | Gln | Gln | Ala | Cys | Thr | Leu | Thr | Ala | Glu | Asn | His | Pro | Thr | Leu | Ser | |
| | | 20 | | | | | 25 | | | | | 30 | | | | |

| tgg | tcc | aag | tgc | acg | tcc | ggc | ggc | agc | tgc | acc | agc | gtc | tcg | ggc | tcc | 144 |
|---|---|---|---|---|---|---|---|---|---|---|---|---|---|---|---|---|
| Trp | Ser | Lys | Cys | Thr | Ser | Gly | Gly | Ser | Cys | Thr | Ser | Val | Ser | Gly | Ser | |
| | 35 | | | | | 40 | | | | | 45 | | | | | |

| gtc | acc | atc | gat | gcc | aac | tgg | cgg | tgg | act | cac | cag | gtc | tcg | agc | tcg | 192 |
|---|---|---|---|---|---|---|---|---|---|---|---|---|---|---|---|---|
| Val | Thr | Ile | Asp | Ala | Asn | Trp | Arg | Trp | Thr | His | Gln | Val | Ser | Ser | Ser | |
| 50 | | | | | 55 | | | | | 60 | | | | | | |

| acc | aac | tgc | tac | acg | ggc | aat | gag | tgg | gac | acg | tcc | atc | tgc | acc | gac | 240 |
|---|---|---|---|---|---|---|---|---|---|---|---|---|---|---|---|---|
| Thr | Asn | Cys | Tyr | Thr | Gly | Asn | Glu | Trp | Asp | Thr | Ser | Ile | Cys | Thr | Asp | |
| 65 | | | | | 70 | | | | | 75 | | | | | 80 | |

| ggt | gct | tcg | tgc | gcc | gcc | gcc | tgc | tgc | ctc | gat | ggc | gcc | gac | tac | tcg | 288 |
|---|---|---|---|---|---|---|---|---|---|---|---|---|---|---|---|---|
| Gly | Ala | Ser | Cys | Ala | Ala | Ala | Cys | Cys | Leu | Asp | Gly | Ala | Asp | Tyr | Ser | |
| | | | | 85 | | | | | 90 | | | | | 95 | | |

| ggc | acc | tat | ggc | atc | acc | acc | agc | ggc | aac | gcc | ctc | agc | ctc | cag | ttc | 336 |
|---|---|---|---|---|---|---|---|---|---|---|---|---|---|---|---|---|
| Gly | Thr | Tyr | Gly | Ile | Thr | Thr | Ser | Gly | Asn | Ala | Leu | Ser | Leu | Gln | Phe | |
| | | | 100 | | | | | 105 | | | | | 110 | | | |

| gtc | act | cag | ggc | ccc | tac | tcg | acc | aac | att | ggc | tcg | cgt | acc | tac | ctg | 384 |
|---|---|---|---|---|---|---|---|---|---|---|---|---|---|---|---|---|
| Val | Thr | Gln | Gly | Pro | Tyr | Ser | Thr | Asn | Ile | Gly | Ser | Arg | Thr | Tyr | Leu | |
| | | 115 | | | | | 120 | | | | | 125 | | | | |

| atg | gcc | tcg | gac | acc | aag | tac | cag | atg | ttc | act | ctg | ctc | ggc | aac | gag | 432 |
|---|---|---|---|---|---|---|---|---|---|---|---|---|---|---|---|---|
| Met | Ala | Ser | Asp | Thr | Lys | Tyr | Gln | Met | Phe | Thr | Leu | Leu | Gly | Asn | Glu | |
| | 130 | | | | | 135 | | | | | 140 | | | | | |

| ttc | acc | ttc | gac | gtg | gac | gtc | aca | ggc | ctc | ggc | tgc | ggt | ctg | aac | ggc | 480 |
|---|---|---|---|---|---|---|---|---|---|---|---|---|---|---|---|---|
| Phe | Thr | Phe | Asp | Val | Asp | Val | Thr | Gly | Leu | Gly | Cys | Gly | Leu | Asn | Gly | |
| 145 | | | | | 150 | | | | | 155 | | | | | 160 | |

| gcc | ctc | tac | ttc | gtc | tcc | atg | gac | gag | gac | ggt | ggt | ctt | tcc | aag | tac | 528 |
|---|---|---|---|---|---|---|---|---|---|---|---|---|---|---|---|---|
| Ala | Leu | Tyr | Phe | Val | Ser | Met | Asp | Glu | Asp | Gly | Gly | Leu | Ser | Lys | Tyr | |
| | | | | 165 | | | | | 170 | | | | | 175 | | |

| tcg | ggc | aac | aag | gct | ggc | gcc | aag | tac | ggc | acc | ggc | tac | tgc | gac | tcg | 576 |
|---|---|---|---|---|---|---|---|---|---|---|---|---|---|---|---|---|
| Ser | Gly | Asn | Lys | Ala | Gly | Ala | Lys | Tyr | Gly | Thr | Gly | Tyr | Cys | Asp | Ser | |
| | | | 180 | | | | | 185 | | | | | 190 | | | |

| cag | tgc | ccc | cgc | gac | ctc | aag | ttc | atc | aac | ggc | gag | gct | aac | aac | gtt | 624 |
|---|---|---|---|---|---|---|---|---|---|---|---|---|---|---|---|---|
| Gln | Cys | Pro | Arg | Asp | Leu | Lys | Phe | Ile | Asn | Gly | Glu | Ala | Asn | Asn | Val | |
| | | 195 | | | | | 200 | | | | | 205 | | | | |

| ggc | tgg | acc | ccg | tcg | tcc | aac | gac | aag | aac | gcc | ggc | ttg | ggc | aac | tac | 672 |
|---|---|---|---|---|---|---|---|---|---|---|---|---|---|---|---|---|
| Gly | Trp | Thr | Pro | Ser | Ser | Asn | Asp | Lys | Asn | Ala | Gly | Leu | Gly | Asn | Tyr | |
| | 210 | | | | | 215 | | | | | 220 | | | | | |

| ggc | agc | tgc | tgc | tcc | gag | atg | gat | gtc | tgg | gag | gcc | aac | agc | atc | tcg | 720 |
|---|---|---|---|---|---|---|---|---|---|---|---|---|---|---|---|---|
| Gly | Ser | Cys | Cys | Ser | Glu | Met | Asp | Val | Trp | Glu | Ala | Asn | Ser | Ile | Ser | |
| 225 | | | | | 230 | | | | | 235 | | | | | 240 | |

| gcg | gcc | tac | acg | ccc | cat | cct | tgc | act | acc | atc | ggc | cag | acg | cgc | tgc | 768 |
|---|---|---|---|---|---|---|---|---|---|---|---|---|---|---|---|---|
| Ala | Ala | Tyr | Thr | Pro | His | Pro | Cys | Thr | Thr | Ile | Gly | Gln | Thr | Arg | Cys | |
| | | | | 245 | | | | | 250 | | | | | 255 | | |

| gag | ggc | gac | gac | tgc | ggt | ggt | acc | tac | agc | act | gac | cgc | tac | gcc | ggc | 816 |
|---|---|---|---|---|---|---|---|---|---|---|---|---|---|---|---|---|
| Glu | Gly | Asp | Asp | Cys | Gly | Gly | Thr | Tyr | Ser | Thr | Asp | Arg | Tyr | Ala | Gly | |

-continued

```
                260                 265                 270
gag tgc gac cct gac gga tgc gac ttc aac tcg tac cgc atg ggc aac       864
Glu Cys Asp Pro Asp Gly Cys Asp Phe Asn Ser Tyr Arg Met Gly Asn
        275                 280                 285 acg acc ttc tac ggc aag ggc atg acc gtc gac acc agc aag aag ttc       912
Thr Thr Phe Tyr Gly Lys Gly Met Thr Val Asp Thr Ser Lys Lys Phe
290                 295                 300 acg gtg gtg acc cag ttc ctg acg gac tcg tct ggc aac ctg tcc gag       960
Thr Val Val Thr Gln Phe Leu Thr Asp Ser Ser Gly Asn Leu Ser Glu
305                 310                 315                 320 atc aag cgc ttc tac gtc cag aac ggc gtc gtc att ccc aac tcg aac      1008
Ile Lys Arg Phe Tyr Val Gln Asn Gly Val Val Ile Pro Asn Ser Asn
                325                 330                 335 tcc aac atc gcg ggc gtc tcg ggc aac tcc atc acc cag gcc ttc tgc      1056
Ser Asn Ile Ala Gly Val Ser Gly Asn Ser Ile Thr Gln Ala Phe Cys
            340                 345                 350 gat gct cag aag acc gct ttc ggc gac acc aac gtc ttc gac caa aag      1104
Asp Ala Gln Lys Thr Ala Phe Gly Asp Thr Asn Val Phe Asp Gln Lys
        355                 360                 365 ggc ggc ctg gcc cag atg ggc aag gct ctt gcc cag ccc atg gtc ctc      1152
Gly Gly Leu Ala Gln Met Gly Lys Ala Leu Ala Gln Pro Met Val Leu
370                 375                 380 gtc atg tcc ctc tgg gac gac cac gcc gtc aac atg ctc tgg ctc gac      1200
Val Met Ser Leu Trp Asp Asp His Ala Val Asn Met Leu Trp Leu Asp
385                 390                 395                 400 tcg acc tac ccg acc aac gcg gcc ggc aag ccg ggc gcc gcc cgc ggt      1248
Ser Thr Tyr Pro Thr Asn Ala Ala Gly Lys Pro Gly Ala Ala Arg Gly
                405                 410                 415 acc tgc ccc acc acc tcg ggc gtc ccc gcc gac gtc gag tcc cag gcg      1296
Thr Cys Pro Thr Thr Ser Gly Val Pro Ala Asp Val Glu Ser Gln Ala
            420                 425                 430 ccc aac tcc aag gtc atc tac tcc aac atc cgc ttc ggc ccc atc ggc      1344
Pro Asn Ser Lys Val Ile Tyr Ser Asn Ile Arg Phe Gly Pro Ile Gly
        435                 440                 445 tcc acc gtc tcc ggc ctg ccc ggc ggc ggc agc aac ccc ggc ggc ggc      1392
Ser Thr Val Ser Gly Leu Pro Gly Gly Gly Ser Asn Pro Gly Gly Gly
450                 455                 460 tcc agc tcc acc acc acc acc aga ccc gcc acc tcc acc acc tcc          1440
Ser Ser Ser Thr Thr Thr Thr Arg Pro Ala Thr Ser Thr Thr Ser
465                 470                 475                 480 tcg gcc agc tcc ggc ccg acc ggc ggt ggc acg gct gcc cac tgg ggc      1488
Ser Ala Ser Ser Gly Pro Thr Gly Gly Gly Thr Ala Ala His Trp Gly
                485                 490                 495 cag tgc ggc ggc atc ggc tgg acc ggc ccg acc gtc tgc gcc tcg ccc      1536
Gln Cys Gly Gly Ile Gly Trp Thr Gly Pro Thr Val Cys Ala Ser Pro
            500                 505                 510 tac acc tgc cag aag ctg aac gac tgg tac tac cag tgc ctc taa          1581
Tyr Thr Cys Gln Lys Leu Asn Asp Trp Tyr Tyr Gln Cys Leu
        515                 520                 525
```

<210> SEQ ID NO 2
<211> LENGTH: 526
<212> TYPE: PRT
<213> ORGANISM: Thielavia terrestris

<400> SEQUENCE: 2

```
Met His Ala Lys Phe Ala Thr Leu Ala Ala Leu Val Ala Ser Ala Ala
1               5                   10                  15

Ala Gln Gln Ala Cys Thr Leu Thr Ala Glu Asn His Pro Thr Leu Ser
            20                  25                  30
```

```
Trp Ser Lys Cys Thr Ser Gly Gly Ser Cys Thr Ser Val Ser Gly Ser
             35                  40                  45

Val Thr Ile Asp Ala Asn Trp Arg Trp Thr His Gln Val Ser Ser Ser
 50                  55                  60

Thr Asn Cys Tyr Thr Gly Asn Glu Trp Asp Thr Ser Ile Cys Thr Asp
 65                  70                  75                  80

Gly Ala Ser Cys Ala Ala Cys Cys Leu Asp Gly Ala Asp Tyr Ser
                 85                  90                  95

Gly Thr Tyr Gly Ile Thr Thr Ser Gly Asn Ala Leu Ser Leu Gln Phe
                100                 105                 110

Val Thr Gln Gly Pro Tyr Ser Thr Asn Ile Gly Ser Arg Thr Tyr Leu
            115                 120                 125

Met Ala Ser Asp Thr Lys Tyr Gln Met Phe Thr Leu Leu Gly Asn Glu
130                 135                 140

Phe Thr Phe Asp Val Asp Val Thr Gly Leu Gly Cys Gly Leu Asn Gly
145                 150                 155                 160

Ala Leu Tyr Phe Val Ser Met Asp Glu Asp Gly Gly Leu Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Asn Val
            195                 200                 205

Gly Trp Thr Pro Ser Ser Asn Asp Lys Asn Ala Gly Leu Gly Asn Tyr
            210                 215                 220

Gly Ser Cys Cys Ser Glu Met Asp Val Trp Glu Ala Asn Ser Ile Ser
225                 230                 235                 240

Ala Ala Tyr Thr Pro His Pro Cys Thr Thr Ile Gly Gln Thr Arg Cys
                245                 250                 255

Glu Gly Asp Asp Cys Gly Gly Thr Tyr Ser Thr Asp Arg Tyr Ala Gly
            260                 265                 270

Glu Cys Asp Pro Asp Gly Cys Asp Phe Asn Ser Tyr Arg Met Gly Asn
            275                 280                 285

Thr Thr Phe Tyr Gly Lys Gly Met Thr Val Asp Thr Ser Lys Lys Phe
290                 295                 300

Thr Val Val Thr Gln Phe Leu Thr Asp Ser Ser Gly Asn Leu Ser Glu
305                 310                 315                 320

Ile Lys Arg Phe Tyr Val Gln Asn Gly Val Val Ile Pro Asn Ser Asn
                325                 330                 335

Ser Asn Ile Ala Gly Val Ser Gly Asn Ser Ile Thr Gln Ala Phe Cys
            340                 345                 350

Asp Ala Gln Lys Thr Ala Phe Gly Asp Thr Asn Val Phe Asp Gln Lys
            355                 360                 365

Gly Gly Leu Ala Gln Met Gly Lys Ala Leu Ala Gln Pro Met Val Leu
370                 375                 380

Val Met Ser Leu Trp Asp Asp His Ala Val Asn Met Leu Trp Leu Asp
385                 390                 395                 400

Ser Thr Tyr Pro Thr Asn Ala Ala Gly Lys Pro Gly Ala Ala Arg Gly
                405                 410                 415

Thr Cys Pro Thr Thr Ser Gly Val Pro Ala Asp Val Glu Ser Gln Ala
            420                 425                 430

Pro Asn Ser Lys Val Ile Tyr Ser Asn Ile Arg Phe Gly Pro Ile Gly
            435                 440                 445
```

```
Ser Thr Val Ser Gly Leu Pro Gly Gly Gly Ser Asn Pro Gly Gly Gly
    450                 455                 460

Ser Ser Ser Thr Thr Thr Thr Thr Arg Pro Ala Thr Ser Thr Thr Ser
465                 470                 475                 480

Ser Ala Ser Ser Gly Pro Thr Gly Gly Gly Thr Ala Ala His Trp Gly
                485                 490                 495

Gln Cys Gly Gly Ile Gly Trp Thr Gly Pro Thr Val Cys Ala Ser Pro
                500                 505                 510

Tyr Thr Cys Gln Lys Leu Asn Asp Trp Tyr Tyr Gln Cys Leu
                515                 520                 525

<210> SEQ ID NO 3
<211> LENGTH: 1590
<212> TYPE: DNA
<213> ORGANISM: Chaetomium thermophilum
<220> FEATURE:
<221> NAME/KEY: CDS
<222> LOCATION: (1)..(1590)

<400> SEQUENCE: 3
```

| | | | | | | | | | | | | | | | | |
|---|---|---|---|---|---|---|---|---|---|---|---|---|---|---|---|---|
| atg | atg | tac | aag | aag | ttc | gcc | gct | ctc | gcc | gcc | ctc | gtg | gct | ggc | gcc | 48 |
| Met | Met | Tyr | Lys | Lys | Phe | Ala | Ala | Leu | Ala | Ala | Leu | Val | Ala | Gly | Ala | |
| 1 | | | | 5 | | | | | 10 | | | | | 15 | | |
| gcc | gcc | cag | cag | gct | tgc | tcc | ctc | acc | act | gag | acc | cac | ccc | aga | ctc | 96 |
| Ala | Ala | Gln | Gln | Ala | Cys | Ser | Leu | Thr | Thr | Glu | Thr | His | Pro | Arg | Leu | |
| | | 20 | | | | 25 | | | | 30 | | | | | | |
| act | tgg | aag | cgc | tgc | acc | tct | ggc | ggc | aac | tgc | tcg | acc | gtg | aac | ggc | 144 |
| Thr | Trp | Lys | Arg | Cys | Thr | Ser | Gly | Gly | Asn | Cys | Ser | Thr | Val | Asn | Gly | |
| | | 35 | | | | | 40 | | | | | 45 | | | | |
| gcc | gtc | acc | atc | gat | gcc | aac | tgg | cgc | tgg | act | cac | acc | gtt | tcc | ggc | 192 |
| Ala | Val | Thr | Ile | Asp | Ala | Asn | Trp | Arg | Trp | Thr | His | Thr | Val | Ser | Gly | |
| 50 | | | | | 55 | | | | | 60 | | | | | | |
| tcg | acc | aac | tgc | tac | acc | ggc | aac | gag | tgg | gat | acc | tcc | atc | tgc | tct | 240 |
| Ser | Thr | Asn | Cys | Tyr | Thr | Gly | Asn | Glu | Trp | Asp | Thr | Ser | Ile | Cys | Ser | |
| 65 | | | | 70 | | | | | 75 | | | | | 80 | | |
| gat | ggc | aag | agc | tgc | gcc | cag | acc | tgc | tgc | gtc | gac | ggc | gct | gac | tac | 288 |
| Asp | Gly | Lys | Ser | Cys | Ala | Gln | Thr | Cys | Cys | Val | Asp | Gly | Ala | Asp | Tyr | |
| | | | | 85 | | | | | 90 | | | | | 95 | | |
| tct | tcg | acc | tat | ggt | atc | acc | acc | agc | ggt | gac | tcc | ctg | aac | ctc | aag | 336 |
| Ser | Ser | Thr | Tyr | Gly | Ile | Thr | Thr | Ser | Gly | Asp | Ser | Leu | Asn | Leu | Lys | |
| | | | 100 | | | | | 105 | | | | | 110 | | | |
| ttc | gtc | acc | aag | cac | cag | tac | ggc | acc | aat | gtc | ggc | tct | cgt | gtc | tac | 384 |
| Phe | Val | Thr | Lys | His | Gln | Tyr | Gly | Thr | Asn | Val | Gly | Ser | Arg | Val | Tyr | |
| | | 115 | | | | | 120 | | | | | 125 | | | | |
| ctg | atg | gag | aac | gac | acc | aag | tac | cag | atg | ttc | gag | ctc | ctc | ggc | aac | 432 |
| Leu | Met | Glu | Asn | Asp | Thr | Lys | Tyr | Gln | Met | Phe | Glu | Leu | Leu | Gly | Asn | |
| 130 | | | | | 135 | | | | | 140 | | | | | | |
| gag | ttc | acc | ttc | gat | gtc | gat | gtc | tct | aac | ctg | ggc | tgc | ggt | ctc | aac | 480 |
| Glu | Phe | Thr | Phe | Asp | Val | Asp | Val | Ser | Asn | Leu | Gly | Cys | Gly | Leu | Asn | |
| 145 | | | | | 150 | | | | | 155 | | | | | 160 | |
| ggt | gcc | ctc | tac | ttc | gtc | tcc | atg | gac | gct | gat | ggt | ggt | atg | agc | aag | 528 |
| Gly | Ala | Leu | Tyr | Phe | Val | Ser | Met | Asp | Ala | Asp | Gly | Gly | Met | Ser | Lys | |
| | | | | 165 | | | | | 170 | | | | | 175 | | |
| tac | tct | ggc | aac | aag | gct | ggc | gcc | aag | tac | ggg | acg | ggg | tac | tgt | gat | 576 |
| Tyr | Ser | Gly | Asn | Lys | Ala | Gly | Ala | Lys | Tyr | Gly | Thr | Gly | Tyr | Cys | Asp | |
| | | | 180 | | | | | 185 | | | | | 190 | | | |
| gct | cag | tgc | ccg | cgc | gac | ctt | aag | ttc | atc | aac | ggc | gag | gcc | aac | att | 624 |
| Ala | Gln | Cys | Pro | Arg | Asp | Leu | Lys | Phe | Ile | Asn | Gly | Glu | Ala | Asn | Ile | |
| | | 195 | | | | | 200 | | | | | 205 | | | | |
| gag | aac | tgg | acc | cct | tcg | acc | aat | gat | gcc | aac | gcc | ggt | ttc | ggc | cgc | 672 |

```
Glu Asn Trp Thr Pro Ser Thr Asn Asp Ala Asn Ala Gly Phe Gly Arg
    210             215             220 tat ggc agc tgc tgc tct gag atg gat atc tgg gag gcc aac aac atg     720
Tyr Gly Ser Cys Cys Ser Glu Met Asp Ile Trp Glu Ala Asn Asn Met
225             230             235             240 gct act gcc ttc act cct cac cct tgc acc att atc ggc cag agc cgc     768
Ala Thr Ala Phe Thr Pro His Pro Cys Thr Ile Ile Gly Gln Ser Arg
                245             250             255 tgc gag ggc aac agc tgc ggt ggc acc tac agc tct gag cgc tat gct     816
Cys Glu Gly Asn Ser Cys Gly Gly Thr Tyr Ser Ser Glu Arg Tyr Ala
            260             265             270 ggt gtt tgc gat cct gat ggc tgc gac ttc aac gcc tac cgc cag ggc     864
Gly Val Cys Asp Pro Asp Gly Cys Asp Phe Asn Ala Tyr Arg Gln Gly
        275             280             285 gac aag acc ttc tac ggc aag ggc atg acc gtc gac acc acc aag aag     912
Asp Lys Thr Phe Tyr Gly Lys Gly Met Thr Val Asp Thr Thr Lys Lys
    290             295             300 atg acc gtc gtc acc cag ttc cac aag aac tcg gct ggc gtc ctc agc     960
Met Thr Val Val Thr Gln Phe His Lys Asn Ser Ala Gly Val Leu Ser
305             310             315             320 gag atc aag cgc ttc tac gtt cag gac ggc aag gtc att gcc aac gcc    1008
Glu Ile Lys Arg Phe Tyr Val Gln Asp Gly Lys Val Ile Ala Asn Ala
                325             330             335 gag tcc aag atc ccc ggc aac ccc ggc aac tcc atc acc cag gag tgg    1056
Glu Ser Lys Ile Pro Gly Asn Pro Gly Asn Ser Ile Thr Gln Glu Trp
            340             345             350 tgc gat gcc cag aag gtc gcc ttc ggt gac atc gat gac ttc aac cgc    1104
Cys Asp Ala Gln Lys Val Ala Phe Gly Asp Ile Asp Asp Phe Asn Arg
        355             360             365 aag ggc ggt atg gct cag atg agc aag gcc ctc gaa ggc cct atg gtc    1152
Lys Gly Gly Met Ala Gln Met Ser Lys Ala Leu Glu Gly Pro Met Val
    370             375             380 ctg gtc atg tcc gtc tgg gat gac cac tac gcc aac atg ctc tgg ctc    1200
Leu Val Met Ser Val Trp Asp Asp His Tyr Ala Asn Met Leu Trp Leu
385             390             395             400 gac tcg acc tac ccc atc gac aag gcc ggc acc ccc ggc gcc gag cgc    1248
Asp Ser Thr Tyr Pro Ile Asp Lys Ala Gly Thr Pro Gly Ala Glu Arg
                405             410             415 ggt gct tgc ccg acc acc tcc ggt gtc cct gcc gag att gag gcc cag    1296
Gly Ala Cys Pro Thr Thr Ser Gly Val Pro Ala Glu Ile Glu Ala Gln
            420             425             430 gtc ccc aac agc aac gtc atc ttc tcc aac atc cgc ttc ggc ccc atc    1344
Val Pro Asn Ser Asn Val Ile Phe Ser Asn Ile Arg Phe Gly Pro Ile
        435             440             445 ggc tcg acc gtc cct ggc ctc gac ggc agc act ccc agc aac ccg acc    1392
Gly Ser Thr Val Pro Gly Leu Asp Gly Ser Thr Pro Ser Asn Pro Thr
    450             455             460 gcc acc gtt gct cct ccc act tct acc acc agc gtg aga agc agc act    1440
Ala Thr Val Ala Pro Pro Thr Ser Thr Thr Ser Val Arg Ser Ser Thr
465             470             475             480 act cag att tcc acc ccg act agc cag ccc ggc ggt tgc acc acc cag    1488
Thr Gln Ile Ser Thr Pro Thr Ser Gln Pro Gly Gly Cys Thr Thr Gln
                485             490             495 aag tgg ggc cag tgc ggt ggt atc ggc tac acc ggc tgc act aac tgc    1536
Lys Trp Gly Gln Cys Gly Gly Ile Gly Tyr Thr Gly Cys Thr Asn Cys
            500             505             510 gtt gct ggc act acc tgc act gag ctc aac ccc tgg tac agc cag tgc    1584
Val Ala Gly Thr Thr Cys Thr Glu Leu Asn Pro Trp Tyr Ser Gln Cys
        515             520             525
```

```
ctg taa                                                                    1590
Leu
```

<210> SEQ ID NO 4
<211> LENGTH: 529
<212> TYPE: PRT
<213> ORGANISM: Chaetomium thermophilum

<400> SEQUENCE: 4

Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln Tyr Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Val Ile Ala Asn Ala
                325                 330                 335

Glu Ser Lys Ile Pro Gly Asn Pro Gly Asn Ser Ile Thr Gln Glu Trp
            340                 345                 350

Cys Asp Ala Gln Lys Val Ala Phe Gly Asp Ile Asp Asp Phe Asn Arg
        355                 360                 365

```
Lys Gly Gly Met Ala Gln Met Ser Lys Ala Leu Glu Gly Pro Met Val
        370                 375                 380

Leu Val Met Ser Val Trp Asp Asp His Tyr Ala Asn Met Leu Trp Leu
385                 390                 395                 400

Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Thr Pro Ser Asn Pro Thr
    450                 455                 460

Ala Thr Val Ala Pro Pro Thr Ser Thr Thr Ser Val Arg Ser Ser Thr
465                 470                 475                 480

Thr Gln Ile Ser Thr Pro Thr Ser Gln Pro Gly Gly Cys Thr Thr Gln
                485                 490                 495

Lys Trp Gly Gln Cys Gly Gly Ile Gly Tyr Thr Gly Cys Thr Asn Cys
            500                 505                 510

Val Ala Gly Thr Thr Cys Thr Glu Leu Asn Pro Trp Tyr Ser Gln Cys
        515                 520                 525

Leu

<210> SEQ ID NO 5
<211> LENGTH: 1356
<212> TYPE: DNA
<213> ORGANISM: Scytalidium sp.
<220> FEATURE:
<221> NAME/KEY: CDS
<222> LOCATION: (1)..(1356)

<400> SEQUENCE: 5 atg cag atc aag agc tac atc cag tac ctg gcc gcg gct ctg ccg ctc     48
Met Gln Ile Lys Ser Tyr Ile Gln Tyr Leu Ala Ala Ala Leu Pro Leu
1               5                   10                  15 ctg agc agc gtc gct gcc cag cag gcc ggc acc atc acc gcc gag aac     96
Leu Ser Ser Val Ala Ala Gln Gln Ala Gly Thr Ile Thr Ala Glu Asn
            20                  25                  30 cac ccc agg atg acc tgg aag agg tgc tcg ggc ccc ggc aac tgc cag    144
His Pro Arg Met Thr Trp Lys Arg Cys Ser Gly Pro Gly Asn Cys Gln
        35                  40                  45 acc gtg cag ggc gag gtc gtc atc gac gcc aac tgg cgc tgg ctg cac    192
Thr Val Gln Gly Glu Val Val Ile Asp Ala Asn Trp Arg Trp Leu His
    50                  55                  60 aac aac ggc cag aac tgc tat gag ggc aac aag tgg acc agc cag tgc    240
Asn Asn Gly Gln Asn Cys Tyr Glu Gly Asn Lys Trp Thr Ser Gln Cys
65                  70                  75                  80 agc tcg gcc acc gac tgc gcg cag agg tgc gcc ctc gac ggt gcc aac    288
Ser Ser Ala Thr Asp Cys Ala Gln Arg Cys Ala Leu Asp Gly Ala Asn
                85                  90                  95 tac cag tcg acc tac ggc gcc tcg acc agc ggc gac tcc ctg acg ctc    336
Tyr Gln Ser Thr Tyr Gly Ala Ser Thr Ser Gly Asp Ser Leu Thr Leu
            100                 105                 110 aag ttc gtc acc aag cac gag tac ggc acc aac atc ggc tcg cgc ttc    384
Lys Phe Val Thr Lys His Glu Tyr Gly Thr Asn Ile Gly Ser Arg Phe
        115                 120                 125 tac ctc atg gcc aac cag aac aag tac cag atg ttc acc ctg atg aac    432
Tyr Leu Met Ala Asn Gln Asn Lys Tyr Gln Met Phe Thr Leu Met Asn
    130                 135                 140
```

```
aac gag ttc gcc ttc gat gtc gac ctc tcc aag gtt gag tgc ggt atc        480
Asn Glu Phe Ala Phe Asp Val Asp Leu Ser Lys Val Glu Cys Gly Ile
145                 150                 155                 160 aac agc gct ctg tac ttc gtc gcc atg gag gag gat ggt ggc atg gcc        528
Asn Ser Ala Leu Tyr Phe Val Ala Met Glu Glu Asp Gly Gly Met Ala
                165                 170                 175 agc tac ccg agc aac cgt gct ggt gcc aag tac ggc acg ggc tac tgc        576
Ser Tyr Pro Ser Asn Arg Ala Gly Ala Lys Tyr Gly Thr Gly Tyr Cys
            180                 185                 190 gat gcc caa tgc gcc cgt gac ctc aag ttc att ggc ggc aag gcc aac        624
Asp Ala Gln Cys Ala Arg Asp Leu Lys Phe Ile Gly Gly Lys Ala Asn
        195                 200                 205 att gag ggc tgg cgc ccg tcc acc aac gac ccc aac gcc ggt gtc ggt        672
Ile Glu Gly Trp Arg Pro Ser Thr Asn Asp Pro Asn Ala Gly Val Gly
    210                 215                 220 ccc atg ggt gcc tgc tgc gct gag atc gac gtt tgg gag tcc aac gcc        720
Pro Met Gly Ala Cys Cys Ala Glu Ile Asp Val Trp Glu Ser Asn Ala
225                 230                 235                 240 tat gct tat gcc ttc acc ccc cac gcc tgc ggc agc aag aac cgc tac        768
Tyr Ala Tyr Ala Phe Thr Pro His Ala Cys Gly Ser Lys Asn Arg Tyr
                245                 250                 255 cac atc tgc gag acc aac aac tgc ggt ggt acc tac tcg gat gac cgc        816
His Ile Cys Glu Thr Asn Asn Cys Gly Gly Thr Tyr Ser Asp Asp Arg
            260                 265                 270 ttc gcc ggc tac tgc gac gcc aac ggc tgc gac tac aac ccc tac cgc        864
Phe Ala Gly Tyr Cys Asp Ala Asn Gly Cys Asp Tyr Asn Pro Tyr Arg
        275                 280                 285 atg ggc aac aag gac ttc tat ggc aag ggc aag acc gtc gac acc aac        912
Met Gly Asn Lys Asp Phe Tyr Gly Lys Gly Lys Thr Val Asp Thr Asn
    290                 295                 300 cgc aag ttc acc gtt gtc tcc cgc ttc gag cgt aac agg ctc tct cag        960
Arg Lys Phe Thr Val Val Ser Arg Phe Glu Arg Asn Arg Leu Ser Gln
305                 310                 315                 320 ttc ttc gtc cag gac ggc cgc aag atc gag gtg ccc cct ccg acc tgg       1008
Phe Phe Val Gln Asp Gly Arg Lys Ile Glu Val Pro Pro Pro Thr Trp
                325                 330                 335 ccc ggc ctc ccg aac agc gcc gac atc acc cct gag ctc tgc gat gct       1056
Pro Gly Leu Pro Asn Ser Ala Asp Ile Thr Pro Glu Leu Cys Asp Ala
            340                 345                 350 cag ttc cgc gtc ttc gat gac cgc aac cgc ttc gcc gag acc ggt ggc       1104
Gln Phe Arg Val Phe Asp Asp Arg Asn Arg Phe Ala Glu Thr Gly Gly
        355                 360                 365 ttc gat gct ctg aac gag gcc ctc acc att ccc atg gtc ctt gtc atg       1152
Phe Asp Ala Leu Asn Glu Ala Leu Thr Ile Pro Met Val Leu Val Met
    370                 375                 380 tcc atc tgg gat gac cac cac tcc aac atg ctc tgg ctc gac tcc agc       1200
Ser Ile Trp Asp Asp His His Ser Asn Met Leu Trp Leu Asp Ser Ser
385                 390                 395                 400 tac ccg ccc gag aag gcc ggc ctc ccc ggt ggc gac cgt ggc ccg tgc       1248
Tyr Pro Pro Glu Lys Ala Gly Leu Pro Gly Gly Asp Arg Gly Pro Cys
                405                 410                 415 ccg acc acc tct ggt gtc cct gcc gag gtc gag gct cag tac ccc gat       1296
Pro Thr Thr Ser Gly Val Pro Ala Glu Val Glu Ala Gln Tyr Pro Asp
            420                 425                 430 gct cag gtc gtc tgg tcc aac atc cgc ttc ggc ccc atc ggc tcg acc       1344
Ala Gln Val Val Trp Ser Asn Ile Arg Phe Gly Pro Ile Gly Ser Thr
        435                 440                 445 gtc aac gtc taa                                                        1356
Val Asn Val
```

<210> SEQ ID NO 6
<211> LENGTH: 451
<212> TYPE: PRT
<213> ORGANISM: Scytalidium sp.

<400> SEQUENCE: 6

Met Gln Ile Lys Ser Tyr Ile Gln Tyr Leu Ala Ala Ala Leu Pro Leu
1               5                   10                  15

Leu Ser Ser Val Ala Ala Gln Ala Gly Thr Ile Thr Ala Glu Asn
            20                  25                  30

His Pro Arg Met Thr Trp Lys Arg Cys Ser Gly Pro Gly Asn Cys Gln
            35                  40                  45

Thr Val Gln Gly Glu Val Val Ile Asp Ala Asn Trp Arg Trp Leu His
        50                  55                  60

Asn Asn Gly Gln Asn Cys Tyr Glu Gly Asn Lys Trp Thr Ser Gln Cys
65                  70                  75                  80

Ser Ser Ala Thr Asp Cys Ala Gln Arg Cys Ala Leu Asp Gly Ala Asn
                85                  90                  95

Tyr Gln Ser Thr Tyr Gly Ala Ser Thr Ser Gly Asp Ser Leu Thr Leu
            100                 105                 110

Lys Phe Val Thr Lys His Glu Tyr Gly Thr Asn Ile Gly Ser Arg Phe
        115                 120                 125

Tyr Leu Met Ala Asn Gln Asn Lys Tyr Gln Met Phe Thr Leu Met Asn
130                 135                 140

Asn Glu Phe Ala Phe Asp Val Asp Leu Ser Lys Val Glu Cys Gly Ile
145                 150                 155                 160

Asn Ser Ala Leu Tyr Phe Val Ala Met Glu Glu Asp Gly Gly Met Ala
                165                 170                 175

Ser Tyr Pro Ser Asn Arg Ala Gly Ala Lys Tyr Gly Thr Gly Tyr Cys
            180                 185                 190

Asp Ala Gln Cys Ala Arg Asp Leu Lys Phe Ile Gly Gly Lys Ala Asn
        195                 200                 205

Ile Glu Gly Trp Arg Pro Ser Thr Asn Asp Pro Asn Ala Gly Val Gly
        210                 215                 220

Pro Met Gly Ala Cys Cys Ala Glu Ile Asp Val Trp Glu Ser Asn Ala
225                 230                 235                 240

Tyr Ala Tyr Ala Phe Thr Pro His Ala Cys Gly Ser Lys Asn Arg Tyr
                245                 250                 255

His Ile Cys Glu Thr Asn Asn Cys Gly Gly Thr Tyr Ser Asp Asp Arg
            260                 265                 270

Phe Ala Gly Tyr Cys Asp Ala Asn Gly Cys Asp Tyr Asn Pro Tyr Arg
        275                 280                 285

Met Gly Asn Lys Asp Phe Tyr Gly Lys Gly Lys Thr Val Asp Thr Asn
        290                 295                 300

Arg Lys Phe Thr Val Val Ser Arg Phe Glu Asn Arg Leu Ser Gln
305                 310                 315                 320

Phe Phe Val Gln Asp Gly Arg Lys Ile Glu Val Pro Pro Thr Trp
                325                 330                 335

Pro Gly Leu Pro Asn Ser Ala Asp Ile Thr Pro Glu Leu Cys Asp Ala
            340                 345                 350

Gln Phe Arg Val Phe Asp Asp Arg Asn Arg Phe Ala Glu Thr Gly Gly
        355                 360                 365

```
Phe Asp Ala Leu Asn Glu Ala Leu Thr Ile Pro Met Val Leu Val Met
        370                 375                 380

Ser Ile Trp Asp Asp His His Ser Asn Met Leu Trp Leu Asp Ser Ser
385                 390                 395                 400

Tyr Pro Pro Glu Lys Ala Gly Leu Pro Gly Gly Asp Arg Gly Pro Cys
                405                 410                 415

Pro Thr Thr Ser Gly Val Pro Ala Glu Val Glu Ala Gln Tyr Pro Asp
            420                 425                 430

Ala Gln Val Val Trp Ser Asn Ile Arg Phe Gly Pro Ile Gly Ser Thr
        435                 440                 445

Val Asn Val
    450

<210> SEQ ID NO 7
<211> LENGTH: 1374
<212> TYPE: DNA
<213> ORGANISM: Thermoascus aurantiacus
<220> FEATURE:
<221> NAME/KEY: CDS
<222> LOCATION: (1)..(1374)

<400> SEQUENCE: 7
```

| | | | | | | | | | | | | | | | | |
|---|---|---|---|---|---|---|---|---|---|---|---|---|---|---|---|---|
| atg | tat | cag | cgc | gct | ctt | ctc | ttc | tct | ttc | ttc | ctc | tcc | gcc | gcc | cgc | 48 |
| Met | Tyr | Gln | Arg | Ala | Leu | Leu | Phe | Ser | Phe | Phe | Leu | Ser | Ala | Ala | Arg | |
| 1 | | | | 5 | | | | | 10 | | | | | 15 | | |
| gcg | cag | cag | gcc | ggt | acc | cta | acc | gca | gag | aat | cac | cct | tcc | ctg | acc | 96 |
| Ala | Gln | Gln | Ala | Gly | Thr | Leu | Thr | Ala | Glu | Asn | His | Pro | Ser | Leu | Thr | |
| | | | 20 | | | | | 25 | | | | | 30 | | | |
| tgg | cag | caa | tgc | tcc | agc | ggc | ggt | agt | tgt | acc | acg | cag | aat | gga | aaa | 144 |
| Trp | Gln | Gln | Cys | Ser | Ser | Gly | Gly | Ser | Cys | Thr | Thr | Gln | Asn | Gly | Lys | |
| | | 35 | | | | | 40 | | | | | 45 | | | | |
| gtc | gtt | atc | gat | gcg | aac | tgg | cgt | tgg | gtc | cat | acc | acc | tct | gga | tac | 192 |
| Val | Val | Ile | Asp | Ala | Asn | Trp | Arg | Trp | Val | His | Thr | Thr | Ser | Gly | Tyr | |
| | 50 | | | | | 55 | | | | | 60 | | | | | |
| acc | aac | tgc | tac | acg | ggc | aat | acg | tgg | gac | acc | agt | atc | tgt | ccc | gac | 240 |
| Thr | Asn | Cys | Tyr | Thr | Gly | Asn | Thr | Trp | Asp | Thr | Ser | Ile | Cys | Pro | Asp | |
| 65 | | | | | 70 | | | | | 75 | | | | | 80 | |
| gac | gtg | acc | tgc | gct | cag | aat | tgt | gcc | ttg | gat | gga | gcg | gat | tac | agt | 288 |
| Asp | Val | Thr | Cys | Ala | Gln | Asn | Cys | Ala | Leu | Asp | Gly | Ala | Asp | Tyr | Ser | |
| | | | | 85 | | | | | 90 | | | | | 95 | | |
| ggc | acc | tat | ggt | gtt | acg | acc | agt | ggc | aac | gcc | ctg | aga | ctg | aac | ttt | 336 |
| Gly | Thr | Tyr | Gly | Val | Thr | Thr | Ser | Gly | Asn | Ala | Leu | Arg | Leu | Asn | Phe | |
| | | | 100 | | | | | 105 | | | | | 110 | | | |
| gtc | acc | caa | agc | tca | ggg | aag | aac | att | ggc | tcg | cgc | ctg | tac | ctg | ctg | 384 |
| Val | Thr | Gln | Ser | Ser | Gly | Lys | Asn | Ile | Gly | Ser | Arg | Leu | Tyr | Leu | Leu | |
| | | 115 | | | | | 120 | | | | | 125 | | | | |
| cag | gac | gac | acc | act | tat | cag | atc | ttc | aag | ctg | ctg | ggt | cag | gag | ttt | 432 |
| Gln | Asp | Asp | Thr | Thr | Tyr | Gln | Ile | Phe | Lys | Leu | Leu | Gly | Gln | Glu | Phe | |
| | 130 | | | | | 135 | | | | | 140 | | | | | |
| acc | ttc | gat | gtc | gac | gtc | tcc | aat | ctc | cct | tgc | ggg | ctg | aac | ggc | gcc | 480 |
| Thr | Phe | Asp | Val | Asp | Val | Ser | Asn | Leu | Pro | Cys | Gly | Leu | Asn | Gly | Ala | |
| 145 | | | | | 150 | | | | | 155 | | | | | 160 | |
| ctc | tac | ttt | gtg | gcc | atg | gac | gcc | gac | ggc | gga | ttg | tcc | aaa | tac | cct | 528 |
| Leu | Tyr | Phe | Val | Ala | Met | Asp | Ala | Asp | Gly | Gly | Leu | Ser | Lys | Tyr | Pro | |
| | | | | 165 | | | | | 170 | | | | | 175 | | |
| ggc | aac | aag | gca | ggc | gct | aag | tat | ggc | act | ggt | tac | tgc | gac | tct | cag | 576 |
| Gly | Asn | Lys | Ala | Gly | Ala | Lys | Tyr | Gly | Thr | Gly | Tyr | Cys | Asp | Ser | Gln | |
| | | | 180 | | | | | 185 | | | | | 190 | | | |
| tgc | cct | cgg | gat | ctc | aag | ttc | atc | aac | ggt | cag | gcc | aac | gtt | gaa | ggc | 624 |
| Cys | Pro | Arg | Asp | Leu | Lys | Phe | Ile | Asn | Gly | Gln | Ala | Asn | Val | Glu | Gly | |

```
                195                 200                 205
tgg cag ccg tct gcc aac gac cca aat gcc ggc gtt ggt aac cac ggt      672
Trp Gln Pro Ser Ala Asn Asp Pro Asn Ala Gly Val Gly Asn His Gly
    210                 215                 220 tcc tgc tgc gct gag atg gat gtc tgg gaa gcc aac agc atc tct act      720
Ser Cys Cys Ala Glu Met Asp Val Trp Glu Ala Asn Ser Ile Ser Thr
225                 230                 235                 240 gcg gtg acg cct cac cca tgc gac acc ccc ggc cag acc atg tgc cag      768
Ala Val Thr Pro His Pro Cys Asp Thr Pro Gly Gln Thr Met Cys Gln
                245                 250                 255 gga gac gac tgt ggt gga acc tac tcc tcc act cga tat gct ggt acc      816
Gly Asp Asp Cys Gly Gly Thr Tyr Ser Ser Thr Arg Tyr Ala Gly Thr
            260                 265                 270 tgc gac cct gat ggc tgc gac ttc aat cct tac cgc cag ggc aac cac      864
Cys Asp Pro Asp Gly Cys Asp Phe Asn Pro Tyr Arg Gln Gly Asn His
        275                 280                 285 tcg ttc tac ggc ccc ggg aag atc gtc gac act agc tcc aaa ttc acc      912
Ser Phe Tyr Gly Pro Gly Lys Ile Val Asp Thr Ser Ser Lys Phe Thr
    290                 295                 300 gtc gtc acc cag ttc atc acc gac gac ggg acc ccc tcc ggc acc ctg      960
Val Val Thr Gln Phe Ile Thr Asp Asp Gly Thr Pro Ser Gly Thr Leu
305                 310                 315                 320 acg gag atc aaa cgc ttc tac gtc cag aac ggc aag gtg atc ccc cag     1008
Thr Glu Ile Lys Arg Phe Tyr Val Gln Asn Gly Lys Val Ile Pro Gln
                325                 330                 335 tcg gag tcg acg atc agc ggc gtc acc ggc aac tca atc acc acc gag     1056
Ser Glu Ser Thr Ile Ser Gly Val Thr Gly Asn Ser Ile Thr Thr Glu
            340                 345                 350 tat tgc acg gcc cag aag gcc gcc ttc ggc gac aac acc ggc ttc ttc     1104
Tyr Cys Thr Ala Gln Lys Ala Ala Phe Gly Asp Asn Thr Gly Phe Phe
        355                 360                 365 acg cac ggc ggg ctt cag aag atc agt cag gct ctg gct cag ggc atg     1152
Thr His Gly Gly Leu Gln Lys Ile Ser Gln Ala Leu Ala Gln Gly Met
    370                 375                 380 gtc ctc gtc atg agc ctg tgg gac gat cac gcc gcc aac atg ctc tgg     1200
Val Leu Val Met Ser Leu Trp Asp Asp His Ala Ala Asn Met Leu Trp
385                 390                 395                 400 ctg gac agc acc tac ccg act gat gcg gac ccg gac acc cct ggc gtc     1248
Leu Asp Ser Thr Tyr Pro Thr Asp Ala Asp Pro Asp Thr Pro Gly Val
                405                 410                 415 gcg cgc ggt acc tgc ccc acg acc tcc ggc gtc ccg gcc gac gtt gag     1296
Ala Arg Gly Thr Cys Pro Thr Thr Ser Gly Val Pro Ala Asp Val Glu
            420                 425                 430 tcg cag aac ccc aat tca tat gtt atc tac tcc aac atc aag gtc gga     1344
Ser Gln Asn Pro Asn Ser Tyr Val Ile Tyr Ser Asn Ile Lys Val Gly
        435                 440                 445 ccc atc aac tcg acc ttc acc gcc aac taa                             1374
Pro Ile Asn Ser Thr Phe Thr Ala Asn
    450                 455

<210> SEQ ID NO 8
<211> LENGTH: 457
<212> TYPE: PRT
<213> ORGANISM: Thermoascus aurantiacus

<400> SEQUENCE: 8

Met Tyr Gln Arg Ala Leu Leu Phe Ser Phe Phe Leu Ser Ala Ala Arg
1               5                   10                  15

Ala Gln Gln Ala Gly Thr Leu Thr Ala Glu Asn His Pro Ser Leu Thr
            20                  25                  30
```

-continued

```
Trp Gln Gln Cys Ser Ser Gly Gly Ser Cys Thr Thr Gln Asn Gly Lys
             35                  40                  45

Val Val Ile Asp Ala Asn Trp Arg Trp Val His Thr Thr Ser Gly Tyr
 50                  55                  60

Thr Asn Cys Tyr Thr Gly Asn Thr Trp Asp Thr Ser Ile Cys Pro Asp
 65                  70                  75                  80

Asp Val Thr Cys Ala Gln Asn Cys Ala Leu Asp Gly Ala Asp Tyr Ser
                     85                  90                  95

Gly Thr Tyr Gly Val Thr Thr Ser Gly Asn Ala Leu Arg Leu Asn Phe
                100                 105                 110

Val Thr Gln Ser Ser Gly Lys Asn Ile Gly Ser Arg Leu Tyr Leu Leu
            115                 120                 125

Gln Asp Asp Thr Thr Tyr Gln Ile Phe Lys Leu Leu Gly Gln Glu Phe
        130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205

Trp Gln Pro Ser Ala Asn Asp Pro Asn Ala Gly Val Gly Asn His Gly
        210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
                260                 265                 270

Cys Asp Pro Asp Gly Cys Asp Phe Asn Pro Tyr Arg Gln Gly Asn His
            275                 280                 285

Ser Phe Tyr Gly Pro Gly Lys Ile Val Asp Thr Ser Lys Phe Thr
        290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
                340                 345                 350

Tyr Cys Thr Ala Gln Lys Ala Ala Phe Gly Asp Asn Thr Gly Phe Phe
            355                 360                 365

Thr His Gly Gly Leu Gln Lys Ile Ser Gln Ala Leu Ala Gln Gly Met
        370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
                420                 425                 430

Ser Gln Asn Pro Asn Ser Tyr Val Ile Tyr Ser Asn Ile Lys Val Gly
            435                 440                 445
```

```
                                      -continued

Pro Ile Asn Ser Thr Phe Thr Ala Asn
    450                 455

<210> SEQ ID NO 9
<211> LENGTH: 1617
<212> TYPE: DNA
<213> ORGANISM: Thielavia australiensis
<220> FEATURE:
<221> NAME/KEY: CDS
<222> LOCATION: (1)..(1617)

<400> SEQUENCE: 9 atg tat gcc aag ttc gcg acc ctc gcc gcc ctc gtg gct ggc gcc tcc        48
Met Tyr Ala Lys Phe Ala Thr Leu Ala Ala Leu Val Ala Gly Ala Ser
1               5                  10                  15 gcc cag gcc gtc tgc agc ctt acc gct gag acg cac cct tcc ctg acg        96
Ala Gln Ala Val Cys Ser Leu Thr Ala Glu Thr His Pro Ser Leu Thr
                20                  25                  30 tgg cag aag tgc acg gcc ccc ggc agc tgc acc aac gtc gcc ggc tcc       144
Trp Gln Lys Cys Thr Ala Pro Gly Ser Cys Thr Asn Val Ala Gly Ser
            35                  40                  45 atc acc atc gac gcc aac tgg cgc tgg act cac cag acc tcg tcc gcg       192
Ile Thr Ile Asp Ala Asn Trp Arg Trp Thr His Gln Thr Ser Ser Ala
        50                  55                  60 acc aac tgc tac agc ggc agc aag tgg gac tcg tcc atc tgc acg acc       240
Thr Asn Cys Tyr Ser Gly Ser Lys Trp Asp Ser Ser Ile Cys Thr Thr
65                  70                  75                  80 ggc acc gac tgc gcc tcc aag tgc tgc att gat ggc gcc gag tac tcg       288
Gly Thr Asp Cys Ala Ser Lys Cys Cys Ile Asp Gly Ala Glu Tyr Ser
                85                  90                  95 agc acc tac ggc atc acc acc agc ggc aat gcc ctg aac ctc aag ttc       336
Ser Thr Tyr Gly Ile Thr Thr Ser Gly Asn Ala Leu Asn Leu Lys Phe
               100                 105                 110 gtc acc aag ggc cag tac tcg acc aac att ggc tcg cgt acc tac ctc       384
Val Thr Lys Gly Gln Tyr Ser Thr Asn Ile Gly Ser Arg Thr Tyr Leu
           115                 120                 125 atg gag tcg gac acc aag tac cag atg ttc aag ctc ctt ggc aac gag       432
Met Glu Ser Asp Thr Lys Tyr Gln Met Phe Lys Leu Leu Gly Asn Glu
       130                 135                 140 ttc acc ttc gac gtc gat gtc tcc aac ctc ggc tgc ggc ctc aac ggc       480
Phe Thr Phe Asp Val Asp Val Ser Asn Leu Gly Cys Gly Leu Asn Gly
145                 150                 155                 160 gcc ctg tac ttc gtc tcc atg gat gcc gac ggt ggc atg tcc aag tac       528
Ala Leu Tyr Phe Val Ser Met Asp Ala Asp Gly Gly Met Ser Lys Tyr
                165                 170                 175 tcg ggc aac aag gcc ggt gcc aag tac ggt acc ggc tac tgc gat gct       576
Ser Gly Asn Lys Ala Gly Ala Lys Tyr Gly Thr Gly Tyr Cys Asp Ala
                180                 185                 190 cag tgc ccc cgc gac ctc aag ttc atc aac ggc gag gcc aac gtt gag       624
Gln Cys Pro Arg Asp Leu Lys Phe Ile Asn Gly Glu Ala Asn Val Glu
            195                 200                 205 ggc tgg gag agc tcg acc aac gac gcc aac gcc ggc tcg ggc aag tac       672
Gly Trp Glu Ser Ser Thr Asn Asp Ala Asn Ala Gly Ser Gly Lys Tyr
        210                 215                 220 ggc agc tgc tgc acc gag atg gac gtc tgg gag gcc aac aac atg gcg       720
Gly Ser Cys Cys Thr Glu Met Asp Val Trp Glu Ala Asn Asn Met Ala
225                 230                 235                 240 act gcc ttc act cct cac cct tgc acc acc att ggc cag act cgc tgc       768
Thr Ala Phe Thr Pro His Pro Cys Thr Thr Ile Gly Gln Thr Arg Cys
                245                 250                 255 gag ggc gac acc tgc ggc ggc acc tac agc tca gac cgc tac gcc ggc       816
```

```
                    Glu Gly Asp Thr Cys Gly Gly Thr Tyr Ser Ser Asp Arg Tyr Ala Gly
                                    260                 265                 270 gtc tgc gac ccc gac gga tgc gac ttc aac tcg tac cgc cag ggc aac           864
Val Cys Asp Pro Asp Gly Cys Asp Phe Asn Ser Tyr Arg Gln Gly Asn
            275                 280                 285 aag acc ttc tac ggc aag ggc atg acc gtc gac acc acc aag aag atc           912
Lys Thr Phe Tyr Gly Lys Gly Met Thr Val Asp Thr Thr Lys Lys Ile
290                 295                 300 acg gtc gtc acc cag ttc ctc aag aac tcg gcc ggc gag ctc tcc gag           960
Thr Val Val Thr Gln Phe Leu Lys Asn Ser Ala Gly Glu Leu Ser Glu
305                 310                 315                 320 atc aag cgc ttc tac gcc cag gac ggc aag gtc atc ccg aac agt gag           1008
Ile Lys Arg Phe Tyr Ala Gln Asp Gly Lys Val Ile Pro Asn Ser Glu
                325                 330                 335 tct acc att gcc ggc atc ccc ggc aac tcc atc acc aag gcc tac tgc           1056
Ser Thr Ile Ala Gly Ile Pro Gly Asn Ser Ile Thr Lys Ala Tyr Cys
            340                 345                 350 gac gcc cag aag acc gtc ttc cag aac acc gac gac ttc acc gcc aag           1104
Asp Ala Gln Lys Thr Val Phe Gln Asn Thr Asp Asp Phe Thr Ala Lys
        355                 360                 365 ggc ggc ctc gtc cag atg ggc aag gcc ctc gcc ggc gac atg gtc ctc           1152
Gly Gly Leu Val Gln Met Gly Lys Ala Leu Ala Gly Asp Met Val Leu
370                 375                 380 gtc atg tcc gtc tgg gac gac cac gcc gtc aac atg ctc tgg cta gac           1200
Val Met Ser Val Trp Asp Asp His Ala Val Asn Met Leu Trp Leu Asp
385                 390                 395                 400 tcg acc tac ccg acc gac cag gtc ggc gtt gcc ggc gct gag cgc ggc           1248
Ser Thr Tyr Pro Thr Asp Gln Val Gly Val Ala Gly Ala Glu Arg Gly
                405                 410                 415 gcc tgc ccc acc acc tcg ggc gtc ccc tcg gat gtt gag gcc aac gcc           1296
Ala Cys Pro Thr Thr Ser Gly Val Pro Ser Asp Val Glu Ala Asn Ala
            420                 425                 430 ccc aac tcc aac gtc atc ttc tcc aac atc cgc ttc ggc ccc atc ggc           1344
Pro Asn Ser Asn Val Ile Phe Ser Asn Ile Arg Phe Gly Pro Ile Gly
        435                 440                 445 tcc acc gtc cag ggc ctg ccc agc tcc ggc ggc acc tcc agc agc tcg           1392
Ser Thr Val Gln Gly Leu Pro Ser Ser Gly Gly Thr Ser Ser Ser Ser
450                 455                 460 agc gcc gct ccc cag tcg acc agc acc aag gcc tcg acc acc acc tca           1440
Ser Ala Ala Pro Gln Ser Thr Ser Thr Lys Ala Ser Thr Thr Thr Ser
465                 470                 475                 480 gct gtc cgc acc acc tcg act gcc acc acc aag acc acc tcc tcg gct           1488
Ala Val Arg Thr Thr Ser Thr Ala Thr Thr Lys Thr Thr Ser Ser Ala
                485                 490                 495 ccc gcc cag ggc acc aac act gcc aag cat tgg cag caa tgc ggt ggt           1536
Pro Ala Gln Gly Thr Asn Thr Ala Lys His Trp Gln Gln Cys Gly Gly
            500                 505                 510 aac ggc tgg acc ggc ccg acg gtg tgc gag tct ccc tac aag tgc acc           1584
Asn Gly Trp Thr Gly Pro Thr Val Cys Glu Ser Pro Tyr Lys Cys Thr
        515                 520                 525 aag cag aac gac tgg tac tcg cag tgc ctc taa                               1617
Lys Gln Asn Asp Trp Tyr Ser Gln Cys Leu
530                 535

<210> SEQ ID NO 10
<211> LENGTH: 538
<212> TYPE: PRT
<213> ORGANISM: Thielavia australiensis

<400> SEQUENCE: 10
```

-continued

```
Met Tyr Ala Lys Phe Ala Thr Leu Ala Ala Leu Val Ala Gly Ala Ser
1               5                   10                  15

Ala Gln Ala Val Cys Ser Leu Thr Ala Glu Thr His Pro Ser Leu Thr
            20                  25                  30

Trp Gln Lys Cys Thr Ala Pro Gly Ser Cys Thr Asn Val Ala Gly Ser
        35                  40                  45

Ile Thr Ile Asp Ala Asn Trp Arg Trp Thr His Gln Thr Ser Ser Ala
50                  55                  60

Thr Asn Cys Tyr Ser Gly Ser Lys Trp Asp Ser Ile Cys Thr Thr
65                  70                  75                  80

Gly Thr Asp Cys Ala Ser Lys Cys Cys Ile Asp Gly Ala Glu Tyr Ser
                85                  90                  95

Ser Thr Tyr Gly Ile Thr Thr Ser Gly Asn Ala Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Lys Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ala
            180                 185                 190

Gln Cys Pro Arg Asp Leu Lys Phe Ile Asn Gly Glu Ala Asn Val Glu
        195                 200                 205

Gly Trp Glu Ser Ser Thr Asn Asp Ala Asn Ala Gly Ser Gly Lys Tyr
    210                 215                 220

Gly Ser Cys Cys Thr Glu Met Asp Val Trp Glu Ala Asn Asn Met Ala
225                 230                 235                 240

Thr Ala Phe Thr Pro His Pro Cys Thr Thr Ile Gly Gln Thr Arg Cys
                245                 250                 255

Glu Gly Asp Thr Cys Gly Gly Thr Tyr Ser Ser Asp Arg Tyr Ala Gly
            260                 265                 270

Val Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Thr Gln Phe Leu Lys Asn Ser Ala Gly Glu Leu Ser Glu
305                 310                 315                 320

Ile Lys Arg Phe Tyr Ala Gln Asp Gly Lys Val Ile Pro Asn Ser Glu
                325                 330                 335

Ser Thr Ile Ala Gly Ile Pro Gly Asn Ser Ile Thr Lys Ala Tyr Cys
            340                 345                 350

Asp Ala Gln Lys Thr Val Phe Gln Asn Thr Asp Phe Thr Ala Lys
        355                 360                 365

Gly Gly Leu Val Gln Met Gly Lys Ala Leu Ala Gly Asp Met Val Leu
    370                 375                 380

Val Met Ser Val Trp Asp Asp His Ala Val Asn Met Leu Trp Leu Asp
385                 390                 395                 400

Ser Thr Tyr Pro Thr Asp Gln Val Gly Val Ala Gly Ala Glu Arg Gly
                405                 410                 415

Ala Cys Pro Thr Thr Ser Gly Val Pro Ser Asp Val Glu Ala Asn Ala
```

```
                420                 425                 430
Pro Asn Ser Asn Val Ile Phe Ser Asn Ile Arg Phe Gly Pro Ile Gly
            435                 440                 445
Ser Thr Val Gln Gly Leu Pro Ser Ser Gly Gly Thr Ser Ser Ser Ser
        450                 455                 460
Ser Ala Ala Pro Gln Ser Thr Ser Thr Lys Ala Ser Thr Thr Thr Ser
465                 470                 475                 480
Ala Val Arg Thr Thr Ser Thr Ala Thr Thr Lys Thr Thr Ser Ser Ala
                485                 490                 495
Pro Ala Gln Gly Thr Asn Thr Ala Lys His Trp Gln Gln Cys Gly Gly
            500                 505                 510
Asn Gly Trp Thr Gly Pro Thr Val Cys Glu Ser Pro Tyr Lys Cys Thr
        515                 520                 525
Lys Gln Asn Asp Trp Tyr Ser Gln Cys Leu
            530                 535

<210> SEQ ID NO 11
<211> LENGTH: 1248
<212> TYPE: DNA
<213> ORGANISM: Verticillium tenerum
<220> FEATURE:
<221> NAME/KEY: CDS
<222> LOCATION: (1)..(1248)

<400> SEQUENCE: 11 atg aag aag gct ctc atc acc agc ctc tcc ctg ctg gcc acg gcc atg      48
Met Lys Lys Ala Leu Ile Thr Ser Leu Ser Leu Leu Ala Thr Ala Met
1               5                   10                  15 ggc cag cag gcc ggt acc ctc gag acc gag acg cat ccc aag ctg acc      96
Gly Gln Gln Ala Gly Thr Leu Glu Thr Glu Thr His Pro Lys Leu Thr
            20                  25                  30 tgg cag cgc tgc acc acc tcc ggc tgt acc aac gtc aac ggc gag gtc     144
Trp Gln Arg Cys Thr Thr Ser Gly Cys Thr Asn Val Asn Gly Glu Val
        35                  40                  45 gtc atc gac gcc aac tgg cgt tgg gcc cac gac atc aac ggc tac gag     192
Val Ile Asp Ala Asn Trp Arg Trp Ala His Asp Ile Asn Gly Tyr Glu
    50                  55                  60 aac tgc ttc gag ggc aac acc tgg acc ggc acc tgc agc ggc gcc gac     240
Asn Cys Phe Glu Gly Asn Thr Trp Thr Gly Thr Cys Ser Gly Ala Asp
65                  70                  75                  80 ggc tgc gcg aag aac tgc gcc gtc gag gga gcc aac tac cag tcg acc     288
Gly Cys Ala Lys Asn Cys Ala Val Glu Gly Ala Asn Tyr Gln Ser Thr
                85                  90                  95 tac ggt gtc tcg acc agc ggc aac gcc ctc tcc ctg cgc ttc gtc acc     336
Tyr Gly Val Ser Thr Ser Gly Asn Ala Leu Ser Leu Arg Phe Val Thr
            100                 105                 110 gag cac gag cac ggc gtc aac acc ggt tcg cgc acg tac ctc atg gag     384
Glu His Glu His Gly Val Asn Thr Gly Ser Arg Thr Tyr Leu Met Glu
        115                 120                 125 agc gcc acc aag tac cag atg ttc acc ctg atg aac aac gag ctc gcc     432
Ser Ala Thr Lys Tyr Gln Met Phe Thr Leu Met Asn Asn Glu Leu Ala
    130                 135                 140 ttc gac gtc gac ctg tcc aag gtc gcc tgc ggc atg aac agc gcc ctc     480
Phe Asp Val Asp Leu Ser Lys Val Ala Cys Gly Met Asn Ser Ala Leu
145                 150                 155                 160 tac ctc gtc ccc atg aag gcc gac ggc ggt ctc tcg tcc gag acc aac     528
Tyr Leu Val Pro Met Lys Ala Asp Gly Gly Leu Ser Ser Glu Thr Asn
                165                 170                 175 aac aac gcc ggc gcc aag tac ggt acc ggt tac tgc gac gcc cag tgc     576
```

```
Asn Asn Ala Gly Ala Lys Tyr Gly Thr Gly Tyr Cys Asp Ala Gln Cys
                180                 185                 190 gct cgc gat ctc aag ttc gtc aac ggc aag gcc aac atc gag ggc tgg       624
Ala Arg Asp Leu Lys Phe Val Asn Gly Lys Ala Asn Ile Glu Gly Trp
        195                 200                 205 caa gcc tcc aag acc gac gag aac tct ggc gtc ggt aac atg ggc tcc       672
Gln Ala Ser Lys Thr Asp Glu Asn Ser Gly Val Gly Asn Met Gly Ser
    210                 215                 220 tgc tgt gct gag att gac gtt tgg gag tcc aac cgc gag tct ttc gcc       720
Cys Cys Ala Glu Ile Asp Val Trp Glu Ser Asn Arg Glu Ser Phe Ala
225                 230                 235                 240 ttc acc cct cac gct tgc tcg cag aac gag tac cac gtc tgc acc ggc       768
Phe Thr Pro His Ala Cys Ser Gln Asn Glu Tyr His Val Cys Thr Gly
                245                 250                 255 gcc aac tgc ggc ggt acc tac tcg gac gac cgc ttc gcc ggc aag tgc       816
Ala Asn Cys Gly Gly Thr Tyr Ser Asp Asp Arg Phe Ala Gly Lys Cys
        260                 265                 270 gat gcc aac ggt tgc gac tac aac ccc ttc cgc gtg ggc aac cag aac       864
Asp Ala Asn Gly Cys Asp Tyr Asn Pro Phe Arg Val Gly Asn Gln Asn
    275                 280                 285 ttc tac ggc ccc ggc atg acc gtc aac acc aac tcc aag ttc act gtc       912
Phe Tyr Gly Pro Gly Met Thr Val Asn Thr Asn Ser Lys Phe Thr Val
290                 295                 300 atc tct cgc ttc cgg gag aac gag gcc tac cag gtc ttc atc cag aac       960
Ile Ser Arg Phe Arg Glu Asn Glu Ala Tyr Gln Val Phe Ile Gln Asn
305                 310                 315                 320 ggc cgc acc atc gag gtc ccc cgt ccc acc ctc tcc ggc atc acc cag      1008
Gly Arg Thr Ile Glu Val Pro Arg Pro Thr Leu Ser Gly Ile Thr Gln
                325                 330                 335 ttc gag gcc aag atc acc ccc gag ttc tgc tcg acc tac ccc acc gtc      1056
Phe Glu Ala Lys Ile Thr Pro Glu Phe Cys Ser Thr Tyr Pro Thr Val
        340                 345                 350 ttc ggc gac cgc gac cgc cac ggc gag atc ggc ggc cac acc gcc ctc      1104
Phe Gly Asp Arg Asp Arg His Gly Glu Ile Gly Gly His Thr Ala Leu
    355                 360                 365 aac gcg gcc ctc cgc atg ccc atg gtc ctc gtc atg tcc atc tgg gcc      1152
Asn Ala Ala Leu Arg Met Pro Met Val Leu Val Met Ser Ile Trp Ala
370                 375                 380 gac cac tac gcc aac atg ctc tgg ctc gac tcc atc tac ccg cca gag      1200
Asp His Tyr Ala Asn Met Leu Trp Leu Asp Ser Ile Tyr Pro Pro Glu
385                 390                 395                 400 aag agg ggc cag ccc ggc gcc cac cgc ggc cgc aga tct aga ggg tga      1248
Lys Arg Gly Gln Pro Gly Ala His Arg Gly Arg Arg Ser Arg Gly
                405                 410                 415

<210> SEQ ID NO 12
<211> LENGTH: 415
<212> TYPE: PRT
<213> ORGANISM: Verticillium tenerum

<400> SEQUENCE: 12

Met Lys Lys Ala Leu Ile Thr Ser Leu Ser Leu Leu Ala Thr Ala Met
1               5                   10                  15

Gly Gln Gln Ala Gly Thr Leu Glu Thr Glu Thr His Pro Lys Leu Thr
                20                  25                  30

Trp Gln Arg Cys Thr Thr Ser Gly Cys Thr Asn Val Asn Gly Glu Val
            35                  40                  45

Val Ile Asp Ala Asn Trp Arg Trp Ala His Asp Ile Asn Gly Tyr Glu
        50                  55                  60
```

Asn Cys Phe Glu Gly Asn Thr Trp Thr Gly Thr Cys Ser Gly Ala Asp
 65                  70                  75                  80

Gly Cys Ala Lys Asn Cys Ala Val Glu Gly Ala Asn Tyr Gln Ser Thr
             85                  90                  95

Tyr Gly Val Ser Thr Ser Gly Asn Ala Leu Ser Leu Arg Phe Val Thr
            100                 105                 110

Glu His Glu His Gly Val Asn Thr Gly Ser Arg Thr Tyr Leu Met Glu
        115                 120                 125

Ser Ala Thr Lys Tyr Gln Met Phe Thr Leu Met Asn Asn Glu Leu Ala
    130                 135                 140

Phe Asp Val Asp Leu Ser Lys Val Ala Cys Gly Met Asn Ser Ala Leu
145                 150                 155                 160

Tyr Leu Val Pro Met Lys Ala Asp Gly Gly Leu Ser Ser Glu Thr Asn
                165                 170                 175

Asn Asn Ala Gly Ala Lys Tyr Gly Thr Gly Tyr Cys Asp Ala Gln Cys
            180                 185                 190

Ala Arg Asp Leu Lys Phe Val Asn Gly Lys Ala Asn Ile Glu Gly Trp
        195                 200                 205

Gln Ala Ser Lys Thr Asp Glu Asn Ser Gly Val Gly Asn Met Gly Ser
    210                 215                 220

Cys Cys Ala Glu Ile Asp Val Trp Glu Ser Asn Arg Glu Ser Phe Ala
225                 230                 235                 240

Phe Thr Pro His Ala Cys Ser Gln Asn Glu Tyr His Val Cys Thr Gly
                245                 250                 255

Ala Asn Cys Gly Gly Thr Tyr Ser Asp Asp Arg Phe Ala Gly Lys Cys
            260                 265                 270

Asp Ala Asn Gly Cys Asp Tyr Asn Pro Phe Arg Val Gly Asn Gln Asn
        275                 280                 285

Phe Tyr Gly Pro Gly Met Thr Val Asn Thr Asn Ser Lys Phe Thr Val
    290                 295                 300

Ile Ser Arg Phe Arg Glu Asn Glu Ala Tyr Gln Val Phe Ile Gln Asn
305                 310                 315                 320

Gly Arg Thr Ile Glu Val Pro Arg Pro Thr Leu Ser Gly Ile Thr Gln
                325                 330                 335

Phe Glu Ala Lys Ile Thr Pro Glu Phe Cys Ser Thr Tyr Pro Thr Val
            340                 345                 350

Phe Gly Asp Arg Asp Arg His Gly Glu Ile Gly Gly His Thr Ala Leu
        355                 360                 365

Asn Ala Ala Leu Arg Met Pro Met Val Leu Val Met Ser Ile Trp Ala
    370                 375                 380

Asp His Tyr Ala Asn Met Leu Trp Leu Asp Ser Ile Tyr Pro Pro Glu
385                 390                 395                 400

Lys Arg Gly Gln Pro Gly Ala His Arg Gly Arg Ser Arg Gly
                405                 410                 415

<210> SEQ ID NO 13
<211> LENGTH: 1341
<212> TYPE: DNA
<213> ORGANISM: Neotermes castaneus
<220> FEATURE:
<221> NAME/KEY: CDS
<222> LOCATION: (1)..(1341)

<400> SEQUENCE: 13 gca cga ggg ctc gct gct gca ttg ttc acc ttt gca tgt agc gtt ggt     48
Ala Arg Gly Leu Ala Ala Ala Leu Phe Thr Phe Ala Cys Ser Val Gly

| | | | | | | | | | | | | | | | | |
|---|---|---|---|---|---|---|---|---|---|---|---|---|---|---|---|---|
| 1 | | | | 5 | | | | | 10 | | | | | 15 | | |

| | | | | | | | | | | | | | | | | |
|---|---|---|---|---|---|---|---|---|---|---|---|---|---|---|---|---|
| atc | ggc | acc | aaa | acg | gcc | gag | aac | cac | ccg | aag | ctg | aac | tgg | cag | aac | 96 |
| Ile | Gly | Thr | Lys | Thr | Ala | Glu | Asn | His | Pro | Lys | Leu | Asn | Trp | Gln | Asn | |
| | | | 20 | | | | | 25 | | | | | 30 | | | |
| tgc | gcc | tcc | aag | ggc | agc | tgc | tca | caa | gtg | tcc | ggc | gaa | gtg | aca | atg | 144 |
| Cys | Ala | Ser | Lys | Gly | Ser | Cys | Ser | Gln | Val | Ser | Gly | Glu | Val | Thr | Met | |
| | | | | 35 | | | | | 40 | | | | | 45 | | |
| gac | tcg | aac | tgg | cgg | tgg | acc | cac | gat | ggc | aac | ggc | aag | aac | tgc | tac | 192 |
| Asp | Ser | Asn | Trp | Arg | Trp | Thr | His | Asp | Gly | Asn | Gly | Lys | Asn | Cys | Tyr | |
| | | 50 | | | | | 55 | | | | | 60 | | | | |
| gac | ggc | aac | acc | tgg | atc | tcc | agc | ctc | tgc | cca | gac | ggc | aag | acc | tgc | 240 |
| Asp | Gly | Asn | Thr | Trp | Ile | Ser | Ser | Leu | Cys | Pro | Asp | Gly | Lys | Thr | Cys | |
| 65 | | | | | 70 | | | | | 75 | | | | | 80 | |
| tct | gac | aag | tgc | gtc | ctc | gat | ggc | gcc | gaa | tac | caa | gcg | acc | tac | ggc | 288 |
| Ser | Asp | Lys | Cys | Val | Leu | Asp | Gly | Ala | Glu | Tyr | Gln | Ala | Thr | Tyr | Gly | |
| | | | | 85 | | | | | 90 | | | | | 95 | | |
| atc | acc | tcg | aac | ggg | acc | gcg | gtc | acc | ctc | aag | ttc | gtc | acc | cac | ggc | 336 |
| Ile | Thr | Ser | Asn | Gly | Thr | Ala | Val | Thr | Leu | Lys | Phe | Val | Thr | His | Gly | |
| | | | | 100 | | | | | 105 | | | | | 110 | | |
| tcg | tac | tcg | acg | aac | atc | ggc | tcc | cgc | ctg | tat | ctc | ctc | aag | gac | gaa | 384 |
| Ser | Tyr | Ser | Thr | Asn | Ile | Gly | Ser | Arg | Leu | Tyr | Leu | Leu | Lys | Asp | Glu | |
| | | | 115 | | | | | 120 | | | | | 125 | | | |
| aac | act | tac | tac | atc | ttc | aag | gtg | aac | aac | aag | gaa | ttc | aca | ttc | agc | 432 |
| Asn | Thr | Tyr | Tyr | Ile | Phe | Lys | Val | Asn | Asn | Lys | Glu | Phe | Thr | Phe | Ser | |
| | | 130 | | | | | 135 | | | | | 140 | | | | |
| gtc | gat | gtg | tcg | aag | ctc | ccg | tgc | ggc | ctg | aac | ggt | gcc | ctc | tac | ttc | 480 |
| Val | Asp | Val | Ser | Lys | Leu | Pro | Cys | Gly | Leu | Asn | Gly | Ala | Leu | Tyr | Phe | |
| 145 | | | | | 150 | | | | | 155 | | | | | 160 | |
| gtc | tcg | atg | gac | gcc | gac | ggt | ggc | gca | gga | aag | tat | tca | ggt | gcg | aag | 528 |
| Val | Ser | Met | Asp | Ala | Asp | Gly | Gly | Ala | Gly | Lys | Tyr | Ser | Gly | Ala | Lys | |
| | | | | 165 | | | | | 170 | | | | | 175 | | |
| cca | ggc | gcg | aag | tac | ggc | ctc | ggc | tac | tgc | gat | gcg | caa | tgc | ccg | agc | 576 |
| Pro | Gly | Ala | Lys | Tyr | Gly | Leu | Gly | Tyr | Cys | Asp | Ala | Gln | Cys | Pro | Ser | |
| | | | 180 | | | | | 185 | | | | | 190 | | | |
| gat | ctg | aag | ttc | atc | aac | ggc | gaa | gcg | aac | agc | gat | ggc | tgg | aag | ccc | 624 |
| Asp | Leu | Lys | Phe | Ile | Asn | Gly | Glu | Ala | Asn | Ser | Asp | Gly | Trp | Lys | Pro | |
| | | 195 | | | | | 200 | | | | | 205 | | | | |
| cag | gcg | aac | gac | aag | aat | gcg | gga | aac | ggc | aaa | tac | gga | tcg | tgc | tgc | 672 |
| Gln | Ala | Asn | Asp | Lys | Asn | Ala | Gly | Asn | Gly | Lys | Tyr | Gly | Ser | Cys | Cys | |
| | 210 | | | | | 215 | | | | | 220 | | | | | |
| tcg | gaa | atg | gac | gtt | tgg | gag | gcg | aac | tcg | cag | gca | aca | gct | tac | act | 720 |
| Ser | Glu | Met | Asp | Val | Trp | Glu | Ala | Asn | Ser | Gln | Ala | Thr | Ala | Tyr | Thr | |
| 225 | | | | | 230 | | | | | 235 | | | | | 240 | |
| ccg | cac | gtc | tgc | aag | acc | acg | ggc | cag | cag | cgc | tgc | tcg | ggc | aca | tcg | 768 |
| Pro | His | Val | Cys | Lys | Thr | Thr | Gly | Gln | Gln | Arg | Cys | Ser | Gly | Thr | Ser | |
| | | | | 245 | | | | | 250 | | | | | 255 | | |
| gaa | tgc | ggc | ggc | cag | gat | ggc | gca | gcg | cgt | ttc | cag | gga | ctg | tgc | gac | 816 |
| Glu | Cys | Gly | Gly | Gln | Asp | Gly | Ala | Ala | Arg | Phe | Gln | Gly | Leu | Cys | Asp | |
| | | | | | 260 | | | | | 265 | | | | | 270 | |
| gag | gac | ggt | tgc | gac | ttc | aac | agc | tgg | cgc | cag | ggc | gac | aag | acg | ttc | 864 |
| Glu | Asp | Gly | Cys | Asp | Phe | Asn | Ser | Trp | Arg | Gln | Gly | Asp | Lys | Thr | Phe | |
| | | | 275 | | | | | 280 | | | | | 285 | | | |
| tac | ggc | ccg | gga | ttg | act | gtt | gac | acg | aag | tcg | ccg | ttc | aca | gtc | gtc | 912 |
| Tyr | Gly | Pro | Gly | Leu | Thr | Val | Asp | Thr | Lys | Ser | Pro | Phe | Thr | Val | Val | |
| | | 290 | | | | | 295 | | | | | 300 | | | | |
| aca | caa | ttc | gtc | gga | agt | ccg | gtg | aag | gaa | atc | cgc | agg | aag | tac | gtc | 960 |
| Thr | Gln | Phe | Val | Gly | Ser | Pro | Val | Lys | Glu | Ile | Arg | Arg | Lys | Tyr | Val | |
| 305 | | | | | 310 | | | | | 315 | | | | | 320 | |
| cag | aac | gga | aag | gtg | att | gag | aac | tcg | aag | aac | aag | att | tcg | gga | att | 1008 |

```
Gln Asn Gly Lys Val Ile Glu Asn Ser Lys Asn Lys Ile Ser Gly Ile
                325                 330                 335 gac gag acg aac gca gtg agt gat act ttc tgc gat cag caa aag aag    1056
Asp Glu Thr Asn Ala Val Ser Asp Thr Phe Cys Asp Gln Gln Lys Lys
                340                 345                 350 gcc ttc ggt gat acg aac gat ttc aag aac aag ggc ggt ttc gct aag    1104
Ala Phe Gly Asp Thr Asn Asp Phe Lys Asn Lys Gly Gly Phe Ala Lys
                355                 360                 365 ttg ggt cag gtg ttc gag act ggt cag gtt ctc gtg ctg tcg ctg tgg    1152
Leu Gly Gln Val Phe Glu Thr Gly Gln Val Leu Val Leu Ser Leu Trp
    370                 375                 380 gat gac cac tcg gtt gca atg ctg tgg ttg gac tcg gcc tac cca acg    1200
Asp Asp His Ser Val Ala Met Leu Trp Leu Asp Ser Ala Tyr Pro Thr
385                 390                 395                 400 aac aag gat aag agc agc cca ggt gtt gac cgt ggg cct tgc ccg acg    1248
Asn Lys Asp Lys Ser Ser Pro Gly Val Asp Arg Gly Pro Cys Pro Thr
                405                 410                 415 act tcc ggg aag ccg gat gat gtt gaa agc caa tct ccc gat gca acc    1296
Thr Ser Gly Lys Pro Asp Asp Val Glu Ser Gln Ser Pro Asp Ala Thr
            420                 425                 430 gtc att tat ggc aac atc aag ttc ggt gca ctg gac tcc act tac         1341
Val Ile Tyr Gly Asn Ile Lys Phe Gly Ala Leu Asp Ser Thr Tyr
            435                 440                 445

<210> SEQ ID NO 14
<211> LENGTH: 447
<212> TYPE: PRT
<213> ORGANISM: Neotermes castaneus

<400> SEQUENCE: 14

Ala Arg Gly Leu Ala Ala Leu Phe Thr Phe Ala Cys Ser Val Gly
1               5                   10                  15

Ile Gly Thr Lys Thr Ala Glu Asn His Pro Lys Leu Asn Trp Gln Asn
                20                  25                  30

Cys Ala Ser Lys Gly Ser Cys Ser Gln Val Ser Gly Glu Val Thr Met
                35                  40                  45

Asp Ser Asn Trp Arg Trp Thr His Asp Gly Asn Gly Lys Asn Cys Tyr
    50                  55                  60

Asp Gly Asn Thr Trp Ile Ser Ser Leu Cys Pro Asp Gly Lys Thr Cys
65                  70                  75                  80

Ser Asp Lys Cys Val Leu Asp Gly Ala Glu Tyr Gln Ala Thr Tyr Gly
                85                  90                  95

Ile Thr Ser Asn Gly Thr Ala Val Thr Leu Lys Phe Val Thr His Gly
                100                 105                 110

Ser Tyr Ser Thr Asn Ile Gly Ser Arg Leu Tyr Leu Leu Lys Asp Glu
            115                 120                 125

Asn Thr Tyr Tyr Ile Phe Lys Val Asn Lys Glu Phe Thr Phe Ser
    130                 135                 140

Val Asp Val Ser Lys Leu Pro Cys Gly Leu Asn Gly Ala Leu Tyr Phe
145                 150                 155                 160

Val Ser Met Asp Ala Asp Gly Ala Gly Lys Tyr Ser Gly Ala Lys
                165                 170                 175

Pro Gly Ala Lys Tyr Gly Leu Gly Tyr Cys Asp Ala Gln Cys Pro Ser
                180                 185                 190

Asp Leu Lys Phe Ile Asn Gly Glu Ala Asn Ser Asp Gly Trp Lys Pro
            195                 200                 205

Gln Ala Asn Asp Lys Asn Ala Gly Asn Gly Lys Tyr Gly Ser Cys Cys
```

-continued

```
                210                 215                 220
Ser Glu Met Asp Val Trp Glu Ala Asn Ser Gln Ala Thr Ala Tyr Thr
225                 230                 235                 240

Pro His Val Cys Lys Thr Thr Gly Gln Gln Arg Cys Ser Gly Thr Ser
                245                 250                 255

Glu Cys Gly Gly Gln Asp Gly Ala Ala Arg Phe Gln Gly Leu Cys Asp
            260                 265                 270

Glu Asp Gly Cys Asp Phe Asn Ser Trp Arg Gln Gly Asp Lys Thr Phe
        275                 280                 285

Tyr Gly Pro Gly Leu Thr Val Asp Thr Lys Ser Pro Phe Thr Val Val
    290                 295                 300

Thr Gln Phe Val Gly Ser Pro Val Lys Glu Ile Arg Arg Lys Tyr Val
305                 310                 315                 320

Gln Asn Gly Lys Val Ile Glu Asn Ser Lys Asn Lys Ile Ser Gly Ile
                325                 330                 335

Asp Glu Thr Asn Ala Val Ser Asp Thr Phe Cys Asp Gln Gln Lys Lys
            340                 345                 350

Ala Phe Gly Asp Thr Asn Asp Phe Lys Asn Lys Gly Phe Ala Lys
        355                 360                 365

Leu Gly Gln Val Phe Glu Thr Gly Gln Val Leu Val Leu Ser Leu Trp
    370                 375                 380

Asp Asp His Ser Val Ala Met Leu Trp Leu Asp Ser Ala Tyr Pro Thr
385                 390                 395                 400

Asn Lys Asp Lys Ser Ser Pro Gly Val Asp Arg Gly Pro Cys Pro Thr
                405                 410                 415

Thr Ser Gly Lys Pro Asp Asp Val Glu Ser Gln Ser Pro Asp Ala Thr
            420                 425                 430

Val Ile Tyr Gly Asn Ile Lys Phe Gly Ala Leu Asp Ser Thr Tyr
        435                 440                 445
```

<210> SEQ ID NO 15
<211> LENGTH: 1359
<212> TYPE: DNA
<213> ORGANISM: Melanocarpus albomyces
<220> FEATURE:
<221> NAME/KEY: CDS
<222> LOCATION: (1)..(1359)

<400> SEQUENCE: 15

```
atg atg atg aag cag tac ctc cag tac ctc gcg gcc gcg ctg ccg ctc     48
Met Met Met Lys Gln Tyr Leu Gln Tyr Leu Ala Ala Ala Leu Pro Leu
1               5                   10                  15 gtc ggc ctc gcc gcc ggc cag cgc gct ggt aac gag acg ccc gag agc     96
Val Gly Leu Ala Ala Gly Gln Arg Ala Gly Asn Glu Thr Pro Glu Ser
            20                  25                  30 cac ccc ccg ctc acc tgg cag agg tgc acg gcc ccg ggc aac tgc cag    144
His Pro Pro Leu Thr Trp Gln Arg Cys Thr Ala Pro Gly Asn Cys Gln
        35                  40                  45 acc gtg aac gcc gag gtc gta att gac gcc aac tgg cgc tgg ctg cac    192
Thr Val Asn Ala Glu Val Val Ile Asp Ala Asn Trp Arg Trp Leu His
    50                  55                  60 gac gac aac atg cag aac tgc tac gac ggc aac cag tgg acc aac gcc    240
Asp Asp Asn Met Gln Asn Cys Tyr Asp Gly Asn Gln Trp Thr Asn Ala
65                  70                  75                  80 tgc agc acc gcc acc gac tgc gct gag aag tgc atg atc gag ggt gcc    288
Cys Ser Thr Ala Thr Asp Cys Ala Glu Lys Cys Met Ile Glu Gly Ala
                85                  90                  95
```

```
ggc gac tac ctg ggc acc tac ggc gcc tcg acc agc ggc gac gcc ctg      336
Gly Asp Tyr Leu Gly Thr Tyr Gly Ala Ser Thr Ser Gly Asp Ala Leu
        100                 105                 110 acg ctc aag ttc gtc acg aag cac gag tac ggc acc aac gtc ggc tcg      384
Thr Leu Lys Phe Val Thr Lys His Glu Tyr Gly Thr Asn Val Gly Ser
        115                 120                 125 cgc ttc tac ctc atg aac ggc ccg gac aag tac cag atg ttc gac ctc      432
Arg Phe Tyr Leu Met Asn Gly Pro Asp Lys Tyr Gln Met Phe Asp Leu
        130                 135                 140 ctg ggc aac gag ctt gcc ttt gac gtc gac ctc tcg acc gtc gag tgc      480
Leu Gly Asn Glu Leu Ala Phe Asp Val Asp Leu Ser Thr Val Glu Cys
145                 150                 155                 160 ggc atc aac agc gcc ctg tac ttc gtc gcc atg gag gag gac ggc ggc      528
Gly Ile Asn Ser Ala Leu Tyr Phe Val Ala Met Glu Glu Asp Gly Gly
                165                 170                 175 atg gcc agc tac ccg agc aac cag gcc ggc gcc cgg tac ggc act ggg      576
Met Ala Ser Tyr Pro Ser Asn Gln Ala Gly Ala Arg Tyr Gly Thr Gly
                180                 185                 190 tac tgc gat gcc caa tgc gct cgt gac ctc aag ttc gtt ggc ggc aag      624
Tyr Cys Asp Ala Gln Cys Ala Arg Asp Leu Lys Phe Val Gly Gly Lys
                195                 200                 205 gcc aac att gag ggc tgg aag ccg tcc acc aac gac ccc aac gct ggc      672
Ala Asn Ile Glu Gly Trp Lys Pro Ser Thr Asn Asp Pro Asn Ala Gly
210                 215                 220 gtc ggc ccg tac ggc ggc tgc tgc gct gag atc gac gtc tgg gag tcg      720
Val Gly Pro Tyr Gly Gly Cys Cys Ala Glu Ile Asp Val Trp Glu Ser
225                 230                 235                 240 aac gcc tat gcc ttc gct ttc acg ccg cac gcg tgc acg acc aac gag      768
Asn Ala Tyr Ala Phe Ala Phe Thr Pro His Ala Cys Thr Thr Asn Glu
                245                 250                 255 tac cac gtc tgc gag acc acc aac tgc ggt ggc acc tac tcg gag gac      816
Tyr His Val Cys Glu Thr Thr Asn Cys Gly Gly Thr Tyr Ser Glu Asp
                260                 265                 270 cgc ttc gcc ggc aag tgc gac gcc aac ggc tgc gac tac aac ccc tac      864
Arg Phe Ala Gly Lys Cys Asp Ala Asn Gly Cys Asp Tyr Asn Pro Tyr
                275                 280                 285 cgc atg ggc aac ccc gac ttc tac ggc aag ggc aag acg ctc gac acc      912
Arg Met Gly Asn Pro Asp Phe Tyr Gly Lys Gly Lys Thr Leu Asp Thr
290                 295                 300 agc cgc aag ttc acc gtc gtc tcc cgc ttc gag gag aac aag ctc tcc      960
Ser Arg Lys Phe Thr Val Val Ser Arg Phe Glu Glu Asn Lys Leu Ser
305                 310                 315                 320 cag tac ttc atc cag gac ggc cgc aag atc gag atc ccg ccg ccg acg     1008
Gln Tyr Phe Ile Gln Asp Gly Arg Lys Ile Glu Ile Pro Pro Pro Thr
                325                 330                 335 tgg gag ggc atg ccc aac agc agc gag atc acc ccc gag ctc tgc tcc     1056
Trp Glu Gly Met Pro Asn Ser Ser Glu Ile Thr Pro Glu Leu Cys Ser
                340                 345                 350 acc atg ttc gat gtg ttc aac gac cgc aac cgc ttc gag gag gtc ggc     1104
Thr Met Phe Asp Val Phe Asn Asp Arg Asn Arg Phe Glu Glu Val Gly
                355                 360                 365 ggc ttc gag cag ctg aac aac gcc ctc cgg gtt ccc atg gtc ctc gtc     1152
Gly Phe Glu Gln Leu Asn Asn Ala Leu Arg Val Pro Met Val Leu Val
370                 375                 380 atg tcc atc tgg gac gac cac tac gcc aac atg ctc tgg ctc gac tcc     1200
Met Ser Ile Trp Asp Asp His Tyr Ala Asn Met Leu Trp Leu Asp Ser
385                 390                 395                 400 atc tac ccg ccc gag aag gag ggc cag ccc ggc gcc gcc cgt ggc gac     1248
Ile Tyr Pro Pro Glu Lys Glu Gly Gln Pro Gly Ala Ala Arg Gly Asp
                405                 410                 415
```

```
tgc ccc acg gac tcg ggt gtc ccc gcc gag gtc gag gct cag ttc ccc    1296
Cys Pro Thr Asp Ser Gly Val Pro Ala Glu Val Glu Ala Gln Phe Pro
        420                 425                 430 gac gcc cag gtc gtc tgg tcc aac atc cgc ttc ggc ccc atc ggc tcg    1344
Asp Ala Gln Val Val Trp Ser Asn Ile Arg Phe Gly Pro Ile Gly Ser
        435                 440                 445 acc tac gac ttc taa                                                 1359
Thr Tyr Asp Phe
    450

<210> SEQ ID NO 16
<211> LENGTH: 452
<212> TYPE: PRT
<213> ORGANISM: Melanocarpus albomyces

<400> SEQUENCE: 16

Met Met Met Lys Gln Tyr Leu Gln Tyr Leu Ala Ala Ala Leu Pro Leu
1               5                   10                  15

Val Gly Leu Ala Ala Gly Gln Arg Ala Gly Asn Glu Thr Pro Glu Ser
            20                  25                  30

His Pro Pro Leu Thr Trp Gln Arg Cys Thr Ala Pro Gly Asn Cys Gln
        35                  40                  45

Thr Val Asn Ala Glu Val Val Ile Asp Ala Asn Trp Arg Trp Leu His
    50                  55                  60

Asp Asp Asn Met Gln Asn Cys Tyr Asp Gly Asn Gln Trp Thr Asn Ala
65                  70                  75                  80

Cys Ser Thr Ala Thr Asp Cys Ala Glu Lys Cys Met Ile Glu Gly Ala
                85                  90                  95

Gly Asp Tyr Leu Gly Thr Tyr Gly Ala Ser Thr Ser Gly Asp Ala Leu
            100                 105                 110

Thr Leu Lys Phe Val Thr Lys His Glu Tyr Gly Thr Asn Val Gly Ser
        115                 120                 125

Arg Phe Tyr Leu Met Asn Gly Pro Asp Lys Tyr Gln Met Phe Asp Leu
    130                 135                 140

Leu Gly Asn Glu Leu Ala Phe Asp Val Asp Leu Ser Thr Val Glu Cys
145                 150                 155                 160

Gly Ile Asn Ser Ala Leu Tyr Phe Val Ala Met Glu Glu Asp Gly Gly
                165                 170                 175

Met Ala Ser Tyr Pro Ser Asn Gln Ala Gly Ala Arg Tyr Gly Thr Gly
            180                 185                 190

Tyr Cys Asp Ala Gln Cys Ala Arg Asp Leu Lys Phe Val Gly Gly Lys
        195                 200                 205

Ala Asn Ile Glu Gly Trp Lys Pro Ser Thr Asn Asp Pro Asn Ala Gly
    210                 215                 220

Val Gly Pro Tyr Gly Gly Cys Cys Ala Glu Ile Asp Val Trp Glu Ser
225                 230                 235                 240

Asn Ala Tyr Ala Phe Ala Phe Thr Pro His Ala Cys Thr Thr Asn Glu
                245                 250                 255

Tyr His Val Cys Glu Thr Thr Asn Cys Gly Gly Thr Tyr Ser Glu Asp
            260                 265                 270

Arg Phe Ala Gly Lys Cys Asp Ala Asn Gly Cys Asp Tyr Asn Pro Tyr
        275                 280                 285

Arg Met Gly Asn Pro Asp Phe Tyr Gly Lys Gly Lys Thr Leu Asp Thr
    290                 295                 300

Ser Arg Lys Phe Thr Val Val Ser Arg Phe Glu Glu Asn Lys Leu Ser
```

```
                305                 310                 315                 320
        Gln Tyr Phe Ile Gln Asp Gly Arg Lys Ile Glu Ile Pro Pro Thr
                        325                 330                 335

Trp Glu Gly Met Pro Asn Ser Ser Glu Ile Thr Pro Glu Leu Cys Ser
                        340                 345                 350

Thr Met Phe Asp Val Phe Asn Asp Arg Asn Arg Phe Glu Glu Val Gly
                        355                 360                 365

Gly Phe Glu Gln Leu Asn Asn Ala Leu Arg Val Pro Met Val Leu Val
                        370                 375                 380

Met Ser Ile Trp Asp Asp His Tyr Ala Asn Met Leu Trp Leu Asp Ser
        385                 390                 395                 400

Ile Tyr Pro Pro Glu Lys Glu Gly Gln Pro Gly Ala Ala Arg Gly Asp
                        405                 410                 415

Cys Pro Thr Asp Ser Gly Val Pro Ala Glu Val Glu Ala Gln Phe Pro
                        420                 425                 430

Asp Ala Gln Val Val Trp Ser Asn Ile Arg Phe Gly Pro Ile Gly Ser
                        435                 440                 445

Thr Tyr Asp Phe
            450

<210> SEQ ID NO 17
<211> LENGTH: 221
<212> TYPE: DNA
<213> ORGANISM: Trichothecium roseum
<220> FEATURE:
<221> NAME/KEY: misc_feature
<222> LOCATION: (1)..(221)
<223> OTHER INFORMATION: Partial CBH1 encoding sequence

<400> SEQUENCE: 17
tacgcccagt gcgcccgtga cctcaagttc ctcggcggca cttccaacta cgacggctgg      60
aagccctcgg acactgacga cagcgccggt gtcggcaacc gcggatcctg ctgcgccgag     120
attgacatct gggagtccaa ctcgcacgcc ttcgccttca cccccacgc ctgcgagaac     180 aacgagtacc acatctgcga gaccaccgac tgcggcggca c                        221

<210> SEQ ID NO 18
<211> LENGTH: 239
<212> TYPE: DNA
<213> ORGANISM: Humicola nigrescens
<220> FEATURE:
<221> NAME/KEY: misc_feature
<222> LOCATION: (1)..(239)
<223> OTHER INFORMATION: Partial CBH1 encoding sequence

<400> SEQUENCE: 18
tacggcacgg ggtactgcga cgcccaatgc gcccgcgatc tcaagttcgt tggcggcaag      60
gccaatgttg agggctggaa acagtccacc aacgatgcca atgccggcgt gggtccgatg     120
ggcggttgct gcgccgaaat tgacgtctgg gaatcgaacg cccatgcctt cgccttcacg     180
ccgcacgcgt gcgagaacaa caagtaccac atctgcgaga ctgacggatg cggcggcac     239

<210> SEQ ID NO 19
<211> LENGTH: 199
<212> TYPE: DNA
<213> ORGANISM: Cladorrhinum foecundissimum
<220> FEATURE:
<221> NAME/KEY: misc_feature
<222> LOCATION: (1)..(199)
<223> OTHER INFORMATION: Partial CBH1 encoding sequence
```

```
<400> SEQUENCE: 19
tacataaacg gtatcggcaa cgttgagggt tggtcctcct ctaccaacga tcccaacgct      60
ggtgtcggta accrcggtac ttgctgctcc gagaatggat atctgggagg ccaacaagat     120
ctcgaccgcc tacactcccc acccctgcac caccatcgac cagcacatgt gcgagggcaa     180
ctcgtgcggc ggaacctac                                                  199

<210> SEQ ID NO 20
<211> LENGTH: 191
<212> TYPE: DNA
<213> ORGANISM: Diplodia gossypina
<220> FEATURE:
<221> NAME/KEY: misc_feature
<222> LOCATION: (1)..(191)
<223> OTHER INFORMATION: Partial CBH1 encoding sequence

<400> SEQUENCE: 20
gttgatccga cggcaaggcc caacgtcgag ggctgggtcc cgtccgagaa cgactccaac      60
gctggtgtcg gcaaccttgg ctcttgctgt gctgagatgg atatctggga ggccaactcc     120
atctcgaccg cctacacccc ccacagctgc aagacggtcg cccagcactc ttgcactggc     180
gacgactgcg g                                                          191

<210> SEQ ID NO 21
<211> LENGTH: 232
<212> TYPE: DNA
<213> ORGANISM: Myceliophthora thermophila
<220> FEATURE:
<221> NAME/KEY: misc_feature
<222> LOCATION: (1)..(232)
<223> OTHER INFORMATION: Partial CBH1 encoding sequence

<400> SEQUENCE: 21
gggtactgcg acgcccaatg cgcacgcgac ctcaagttcg tcggcggcaa gggcaacatc      60
gagggctgga agccgtccac caacgatgcc aatgccggtg tcggtcctta tggcgggtgc     120
tgcgctgaga tcgacgtctg ggagtcgaac aagtatgctt tcgctttcac cccgcacggt     180
tgcgagaacc ctaaatacca cgtctgcgag accaccaact gcggcggcac ct             232

<210> SEQ ID NO 22
<211> LENGTH: 467
<212> TYPE: DNA
<213> ORGANISM: Rhizomucor pusillus
<220> FEATURE:
<221> NAME/KEY: misc_feature
<222> LOCATION: (1)..(467)
<223> OTHER INFORMATION: Partial CBH1 encoding sequence

<400> SEQUENCE: 22
tccttcgcct ttacccccca cgcttgctcg cagnaacgag taccacgtct gcaccaccaa      60
caactgcggc ggcaccctact cggacgaccg cttcgccggc aagtgcgacg ccaacggttg    120
cgactacaac ccgttccgcc tgggcaacca ggacttctac ggcccgggca tgaccgtcga    180
caccaactcc aagttcaccg tcatctcccg cttcagggag aacgaggcct accaggtctt    240
catgcagggc ggccggacca tcgaggtccc ggccccgcag ctgtccgggc tcacccagtt    300
cgacgccaag atcaccccg agttctgcga cacctacccg accgtcttcg acgaccgcaa    360
ccgccacggc gagatcggcg gccacaccgc cctcaacgcc gccctgcgca tgcccatggt    420
cctcgtcatg tccatctggg ctgaccacta cgccagctgc tagtgtc                  467
```

<210> SEQ ID NO 23
<211> LENGTH: 534
<212> TYPE: DNA
<213> ORGANISM: Meripilus giganteus
<220> FEATURE:
<221> NAME/KEY: misc_feature
<222> LOCATION: (1)..(534)
<223> OTHER INFORMATION: Partial CBH1 encoding sequence

<400> SEQUENCE: 23

```
gggagggctc cccgaacgac ccgaacgcgg gaagcggcca gtacggaacg tgctgcaacg    60
agatggacat ctgggaggcg aaccagaacg gcgcggcggt cacgccgcac gtctgctccg   120
tcgacggcca gacgcgctgc gagggcacgg actgcggcga cggcgacgag cggtacgacg   180
gcatctgcga caaggacggc tgcgacttca actcgtaccg catgggcgac cagtccttcc   240
tcggcctcgg caagaccgtc gacacctcga agaagttcac cgtcgtcacc cagttcctca   300
ccgcggacaa cacgacgtcc ggccagctca cggagatccg ccggctgtac gtgcaggacg   360
gcaaggtcat cgcgaactcg aagacgaaca tccccggcct cgactcgttc gactccatca   420
ccgacgactt ctgcaacgcg cagaaggagg tcttcggcga caccaactcg ttcgagaagc   480
tcggcggcct cgcggagatg ggcaaggcct tccagaaggg catggtcctc gtca          534
```

<210> SEQ ID NO 24
<211> LENGTH: 563
<212> TYPE: DNA
<213> ORGANISM: Exidia glandulosa
<220> FEATURE:
<221> NAME/KEY: misc_feature
<222> LOCATION: (1)..(563)
<223> OTHER INFORMATION: Partial CBH1 encoding sequence

<400> SEQUENCE: 24

```
gccacgtcga gggctggact ccttcmccaa cgatgccaac gccggcattg gcacccacgg    60
ctcctgctgt tcggagatgg acatctggga ggctaacaat gttgccgctg cgtacacccc   120
ccatccttgc acaactatcg gccagtcgat ctgctcgggc gattcttgcg gaggaaccta   180
cagctctgac cgttacgccg gtgtctgcga tccagacggt tgcgatttca acagctaccg   240
catgggcgac acgggcttct acggcaaggg cctgacagtc gacacgagct ccaagttcac   300
cgtcgtcacc cagttcctca ccggctccga cggcaacctt ccgagatca agcgcttcta   360 cgtccagaac ggcaaggtca ttcccaactc gcagtccaag attgccggcg tcagcggcaa   420
ctccatcacc accgacttct gctccgccca gaagaccgcc ttcggcgaca ccaacgtctt   480
cgcgcaaaag ggaggtactc gccgggatgg gcgccgccct caaggccggc atggtcctcg   540
tcatgtccat ctgggacgac cac                                            563
```

<210> SEQ ID NO 25
<211> LENGTH: 218
<212> TYPE: DNA
<213> ORGANISM: Xylaria hypoxylon
<220> FEATURE:
<221> NAME/KEY: misc_feature
<222> LOCATION: (1)..(218)
<223> OTHER INFORMATION: Partial CBH1 encoding sequence

<400> SEQUENCE: 25

```
gacgctcagt gtgcccgtga cttgaagttc gtcggtggca agggcaacgt tgagggatgg    60
gagccatcca ccaacgacga caacgccggt gttggcccctt acggwgcctg ctgtgccgaa   120
atsgatgtst gggagtccaa ctstcactct ttcgctttca cccctcaccc wtgcaccacc   180
```
aacgaatacc acgtctgtga gcaggacgag tgtggcgg                                    218

<210> SEQ ID NO 26
<211> LENGTH: 492
<212> TYPE: DNA
<213> ORGANISM: Acremonium sp.
<220> FEATURE:
<221> NAME/KEY: misc_feature
<222> LOCATION: (1)..(492)
<223> OTHER INFORMATION: Partial CBH1 encoding sequence

<400> SEQUENCE: 26
gggacggggt actgcgacgc ccaatgcgcc cgtgatctca agttcgtcgg cggcaaggcc     60
aacattgagg gctggaggcc gtccaccaac gacgcgaacg ccggcgtcgg cccgatgggc    120
ggctgctgcg cggaaatcga tgtctgggag tccaacgccc acgcttttgc cttcacgccg    180
cacgcgtgcg agaacaacaa ctaccacatc tgcgagacct ccaactgcgg cggtacctac    240
tccgacgacc gcttcgccgg cctctgcgac gccaacggct gcgactacaa cccgtaccgc    300
atgggcaacc ccgacttcta cggcaagggc aagactcttg acacctcgcg gaagttcacc    360
gtcgtcaccc gctttcagga gaacgacctc tcgcagtact tcgtccagga cggcccgaag    420
atcgagatcc cgcccccgac ctgggacggc ctcccgaaga gcagcacata cgccgagctg    480
tgcgcgaccc ag                                                       492

<210> SEQ ID NO 27
<211> LENGTH: 481
<212> TYPE: DNA
<213> ORGANISM: Acremonium sp.
<220> FEATURE:
<221> NAME/KEY: misc_feature
<222> LOCATION: (1)..(481)
<223> OTHER INFORMATION: Partial CBH1 encoding sequence

<400> SEQUENCE: 27
ggctccgttt actcctaccc ttgcacggaa atcggccaga gccgctgcga gggcgacagc     60
tgcggcggta cctacagcac cgaccgctac gctggcgtct cgaccccga tggatgcgac    120
ttcaactcgt accgccaggg caacaagacc ttctatggca agggcatgac cgtcgacacc    180
accaagaaga ttaccgtcgt cacccagttc ctcaccgact cgtccggcaa cctgtccgag    240
atcaagcgct tctacgccca gaacggcgtc gtcatcccca actccgagtc caccattgct    300
ggcgtccctg gcaactcgat cacccaggac tactgcgaca agcagaagac cgcctttggt    360
gacaacaacg acttcgacaa gaagggtggt ctcgcccaga tgggtaaggc cctggcccaa    420
cccatggtcc tcgtcatgtc cgtctgggat gaccatgccg tcaacatgct ctgcttcgaa    480
a                                                                   481

<210> SEQ ID NO 28
<211> LENGTH: 463
<212> TYPE: DNA
<213> ORGANISM: Chaetomium sp.
<220> FEATURE:
<221> NAME/KEY: misc_feature
<222> LOCATION: (1)..(463)
<223> OTHER INFORMATION: Partial CBH1 encoding sequence

<400> SEQUENCE: 28
ctccccgtct tcacgccgca cgcgtgcaag aacatcaagt accacgtctg cgagacgtcg     60
ggatgcggcg gcacctactc ggaggaccgc ttcgcgggcg actgcgacgc caacggttgc    120
gactacaacc cctaccgcat gggcaacacc gacttctacg gcaagggcat gacggtcgac    180

```
accagcaaga agttcaccgt cgtgacccaa ttccaggaga acaagctcac ccagttcttc    240
gtccagaacg gcaagaagat cgagatccct ggccccaagt gggacggcat tgagggcgac    300
agcgccgcca tcacgcccca gctgtgcact tccatgttca aggccttcga cgaccgcgat    360
cgcttctcgg aggtcggcgg cttcacccag atcaaccagg ccctctcggt gcccatggtg    420
ctcgtcatgt ccatctggga cgaccactac gccaacatgc ttg                      463

<210> SEQ ID NO 29
<211> LENGTH: 513
<212> TYPE: DNA
<213> ORGANISM: Chaetomidium pingtungium
<220> FEATURE:
<221> NAME/KEY: misc_feature
<222> LOCATION: (1)..(513)
<223> OTHER INFORMATION: Partial CBH1 encoding sequence

<400> SEQUENCE: 29
gaagggtggc agccctcctc caacgatgcc aatgcgggta ccggcaacca cgggtcctgc     60
tgcgcggaga tggatatctg ggaggccaac agcatctcca cggccttcac cccccatccg    120
tgcgacacgc ccggccaggt gatgtgcacc ggtgatgcct gcggtggcac ctacagctcc    180
gaccgctacg gcggcacctg cgaccccgac ggatgtgatt tcaactcctt ccgccagggc    240
aacaagacct tctacggccc tggcatgacc gtcgacacca agagcaagtt taccgtcgtc    300
acccagttca tcaccgacga cggcacctcc agcggcaccc tcaaggagat caagcgcttc    360
tacgtgcaga acggcaaggt gatccccaac tcggagtcga cctggaccgg cgtcagcggc    420
aactccatca ccaccgagta ctgcaccgcc cagaagagcc tgttccagga ccagaacgtc    480
ttcgaaaagc acggtggcct cgagggcatg ggt                                 513

<210> SEQ ID NO 30
<211> LENGTH: 579
<212> TYPE: DNA
<213> ORGANISM: Myceliophthora thermophila
<220> FEATURE:
<221> NAME/KEY: misc_feature
<222> LOCATION: (1)..(579)
<223> OTHER INFORMATION: Partial CBH1 encoding sequence

<400> SEQUENCE: 30
gagatggata tttgggaggc caacaacatg gccgccgcct tcactcccca cccttgcacc     60
gtgatcggcc agtcgcgctg cgagggcgac tcgtgcggcg gtacctacag caccgaccgc    120
tatgccggca tctgcgaccc cgacggatgc gacttcaact cgtaccgcca gggcaacaag    180
accttctacg gcaagggcat gacggtcgac acgaccaaga gatcacggt cgtcacccag    240 ttcctcaaga actcggccgg cgagctctcc gagatcaagc ggttctacgt ccagaacggc    300
aaggtcatcc ccaactccga gtccaccatc ccgggcgtcg agggcaactc cattacccag    360
gactggtgcg accgcagaa ggccgctttc ggcgacgtga ccgactttca ggacaagggc    420
ggcatggtcc agatgggcaa ggccctcgcg ggcccaatgg tcctcgtcat gtccatctgg    480
gacgaccacg ccgtcaacat gctctggctc gaaatcacta gtgcggccgc tgcaggtcga    540
ccatatggga gagctccacg cgttggatgc atagcttga                           579

<210> SEQ ID NO 31
<211> LENGTH: 514
<212> TYPE: DNA
<213> ORGANISM: Myceliophthora hinnulea
<220> FEATURE:
```

```
<221> NAME/KEY: misc_feature
<222> LOCATION: (1)..(514)
<223> OTHER INFORMATION: Partial CBH1 encoding sequence

<400> SEQUENCE: 31
cgtgagggct gggagagctc gaccaacgat gccaacgccg gcacgggcag gtacggcagc      60
tgctgctccg agatggacgt ctgggaggcc aacaacatgg ccaccgcctt caccccccat     120
ccttgcacca tcatcggcca gtcgcgctgc gagggcgaga cgtgcggcgg cacctacagc     180
tcggaccgct acgccggcgt ctgcgacccc gacggctgcg acttcaactc gtaccgccag     240
ggcaacaaga ccttctacgg caagggcatg acggtcgaca cgaccaagaa gctcacggtc     300
gtcacgcagt tcctcaagaa ctcggccggc gagctgtccg agatcaagcg gttctacgtc     360
caggacggca aggtgatccc caactccgag tccaccatcc ccggcgtcga gggcaactcg     420
atcacgcagg actggtgcga ccgccagaag gccgccttcg gcgacgtcac cgacttccag     480
gacaagggcg gcatggtcca gatggcaagg cgct                                 514

<210> SEQ ID NO 32
<211> LENGTH: 477
<212> TYPE: DNA
<213> ORGANISM: Sporotrichum pruinosum
<220> FEATURE:
<221> NAME/KEY: misc_feature
<222> LOCATION: (1)..(477)
<223> OTHER INFORMATION: Partial CBH1 encoding sequence

<400> SEQUENCE: 32 caccccttgcc gcaccacgaa cgacggtggc taccaacgct gccaaggacg tgactgcaac      60
cagcctcgtt atgagggtct ttgcgatcct gacggttgcg actacaaccc tttccgtatg     120
ggtaaccgcg aattctacgg ccctggaaag accgtcgaca ccaacaggaa gttcactgtt     180
gtgacccaat tcattaccga caacaactct gacactggta ccctcgtcga catccgccgc     240
ctctacgtcc aagacggccg tgtcattgcc aaccctccca ccaacttccc cggtctcatg     300
cccgcccacg actccatcac ttagcaattc tgtgacgacg ccaagcgagc attcgaggac     360
aacgacagct ttggcaggaa cggtggtctt gctcacatgg gtcgctccct tgccaagggc     420
catgtcctcg ccctttccat ttggaatgat cacactgcca acatgctctg gctcgaa       477

<210> SEQ ID NO 33
<211> LENGTH: 500
<212> TYPE: DNA
<213> ORGANISM: Thielavia cf. microspora
<220> FEATURE:
<221> NAME/KEY: misc_feature
<222> LOCATION: (1)..(500)
<223> OTHER INFORMATION: Partial CBH1 encoding sequence

<400> SEQUENCE: 33
gagatagatg tctgggagtc caactcgcac tcgtttgcct tcacgccgca cgcgtgcaag      60
aacaacaagt accacgtctg ccagacgacc gggtgcggcg gcacctactc ggaggaccgc     120
ttcgccggcg actgcgacgc caacggctgc gactacaacc cctaccgcat gggcaacacc     180
gacttttacg gcaagggcaa gacggtcgac acgagcaaga gtttaccat ggtgacccag     240 ttccaaaaga acaagctcgt ccagttcttt gtccaggacg gcaagaagat cgacatcccc     300
ggccccaagt gggacggcct gcagcagggc agcgccgcca tcaccccgga gctgtgcacc     360
ttcatgttca aggccttcaa cgaccgcgac cgcttctcag aggttggcgg cttcgaccag     420
atcaacacgg ccctctcggt gccaatggtg ctcgtcatgt ccatctggga tgatcactac     480
```

```
gccaacatgc tctggcttga                                                500
```

<210> SEQ ID NO 34
<211> LENGTH: 470
<212> TYPE: DNA
<213> ORGANISM: Scytalidium sp.
<220> FEATURE:
<221> NAME/KEY: misc_feature
<222> LOCATION: (1)..(470)
<223> OTHER INFORMATION: Partial CBH1 encoding sequence

<400> SEQUENCE: 34

```
cgttnggccc gcgtcgcatg ctcccgcccg catggcccgc gggatttcca gccagagcat      60
gttggagtgg tggtcatccc agatggacat gacaaggacc atgggaatgg tgagggcctc     120
gttcagagca tcgaagccac cggtctcggc gaagcggttg cggtcatcga agacgcggaa     180
ctgagcatcg cagagctcag gggtgatgtc ggcgctgttc gggaggccgg gccaggtcgg     240
aggggggcacc tcgatcttgc ggccgtcctg gacgaagaac tgagagagcc tgttacgctc    300
gaagcgggag acaacggtga acttgcggtt ggtgtcgacg gtcttgccct gccatagaa      360
gtccttgttg cccatgcggt aggggttgta gtcgcagccg ttggcatcgc agtagccggc     420
gaagcggtca tccgagtagg taccaccgca gttgttggtc tccagatgtg                470
```

<210> SEQ ID NO 35
<211> LENGTH: 491
<212> TYPE: DNA
<213> ORGANISM: Scytalidium sp.
<220> FEATURE:
<221> NAME/KEY: misc_feature
<222> LOCATION: (1)..(491)
<223> OTHER INFORMATION: Partial CBH1 encoding sequence

<400> SEQUENCE: 35

```
gaaatcgacg tctgggagtc gaacgcctat gcctatgcct taccccgcac gcttgcggca      60
gccagaaccg ctaccacgtc tgcgagacca acaactgcgg tggtacctac tcggatgacc     120
gcttcgccgg ttactgcgat gccaacggct gcgactacaa cccgtaccgc atgggcaaca     180
gggacttcta cggcaagggc ctgcaggtcg acaccagccg gaagttcacc gtcgtgagcc     240
gcttcgagcg caacaagctc acccagttct tcgttcagga cggccgcaag atcgagcccc     300
ctgcgccgac ctgggacggc atcccgaaga gcgccgacat cacccccgag ttctgcagcg     360
cccagttcaa ggtcttcgac gaccgtgacc gcttcgcgga ctggcggc ttcgatgccc       420
tgaacgatgc tctcagcatt cccatggtcc ttgtcatgtc catctgggat taccactact    480
ccaacataat c                                                          491
```

<210> SEQ ID NO 36
<211> LENGTH: 221
<212> TYPE: DNA
<213> ORGANISM: Trichophaea saccata
<220> FEATURE:
<221> NAME/KEY: misc_feature
<222> LOCATION: (1)..(221)
<223> OTHER INFORMATION: Partial CBH1 encoding sequence

<400> SEQUENCE: 36

```
tgcgactccc agtgtccccg cgatctcaag ttcatcaatg gacagggcaa cgttgaaggc      60
tggaagccat cctcaaatga tgccaacgca ggcgtcgggg gacacggttc ctgctgcgca     120
gagatggatg tttgggaggc caattccatc tccgcggccg taacaccgca ctcgtgctcc     180
```

```
acaaccagcc agacgatgtg caacggcgac tcctgcggcg g          221
```

<210> SEQ ID NO 37
<211> LENGTH: 1365
<212> TYPE: DNA
<213> ORGANISM: Diplodia gossypina
<220> FEATURE:
<221> NAME/KEY: CDS
<222> LOCATION: (1)..(1365)

<400> SEQUENCE: 37

```
atg ctt acc cag gca gtt ctc gct act ctc gcc acc ctg gcc gcc agc          48
Met Leu Thr Gln Ala Val Leu Ala Thr Leu Ala Thr Leu Ala Ala Ser
1               5                   10                  15 cag cag gtc ggc acc cag aag gag gag gtc cac ccc tcc atg acc tgg          96
Gln Gln Val Gly Thr Gln Lys Glu Glu Val His Pro Ser Met Thr Trp
            20                  25                  30 cag act tgc acc agc agc ggc tgc acc acc aac cag ggc tcc atc gtc         144
Gln Thr Cys Thr Ser Ser Gly Cys Thr Thr Asn Gln Gly Ser Ile Val
        35                  40                  45 gtt gac gcc aac tgg cgc tgg gtc cac aac acc gag ggc tac acc aac         192
Val Asp Ala Asn Trp Arg Trp Val His Asn Thr Glu Gly Tyr Thr Asn
    50                  55                  60 tgc tac acg ggc aac acc tgg aac gcc gac tac tgc acc gac aac acc         240
Cys Tyr Thr Gly Asn Thr Trp Asn Ala Asp Tyr Cys Thr Asp Asn Thr
65                  70                  75                  80 gag tgc gcc tcc aac tgc gcc ctc gac ggc gcc gac tac tct ggc acc         288
Glu Cys Ala Ser Asn Cys Ala Leu Asp Gly Ala Asp Tyr Ser Gly Thr
                85                  90                  95 tac ggc gct acc acc tcc ggc gac tcg ctg cgc ctg aac ttc atc acc         336
Tyr Gly Ala Thr Thr Ser Gly Asp Ser Leu Arg Leu Asn Phe Ile Thr
            100                 105                 110 aac ggc cag cag aag aac att ggc tcc cgc atg tac ctc atg cag gat         384
Asn Gly Gln Gln Lys Asn Ile Gly Ser Arg Met Tyr Leu Met Gln Asp
        115                 120                 125 gac gag acc tac gcc gtc cac aag ctc ctc aac aag gag ttc acc ttc         432
Asp Glu Thr Tyr Ala Val His Lys Leu Leu Asn Lys Glu Phe Thr Phe
    130                 135                 140 gac gtc gac acc tcc aag ctg cct tgc ggc ctc aac ggt gcc gtc tac         480
Asp Val Asp Thr Ser Lys Leu Pro Cys Gly Leu Asn Gly Ala Val Tyr
145                 150                 155                 160 ttc gtc tcc atg gac gct gac ggt ggc atg gcc aag ttc ccc gac aac         528
Phe Val Ser Met Asp Ala Asp Gly Gly Met Ala Lys Phe Pro Asp Asn
                165                 170                 175 aag gcc ggc gcc aag tac ggt acc ggt tac tgc gac tcg cag tgc ccc         576
Lys Ala Gly Ala Lys Tyr Gly Thr Gly Tyr Cys Asp Ser Gln Cys Pro
            180                 185                 190 cgt gac ctc aag ttc atc gac ggc aag gcc aac gtc gag ggc tgg gtc         624
Arg Asp Leu Lys Phe Ile Asp Gly Lys Ala Asn Val Glu Gly Trp Val
        195                 200                 205 ccg tcc gag aac gac tcc aac gct ggt gtc ggc aac ctt ggc tct tgc         672
Pro Ser Glu Asn Asp Ser Asn Ala Gly Val Gly Asn Leu Gly Ser Cys
    210                 215                 220 tgt gct gag atg gat atc tgg gag gcc aac tcc atc tcg acc gcc tac         720
Cys Ala Glu Met Asp Ile Trp Glu Ala Asn Ser Ile Ser Thr Ala Tyr
225                 230                 235                 240 acc ccc cac agc tgc aag acg gtc gcc cag cac tct tgc act ggc gac         768
Thr Pro His Ser Cys Lys Thr Val Ala Gln His Ser Cys Thr Gly Asp
                245                 250                 255 gac tgc ggt ggc acc tac tcc gcg acc cgc tac gcc ggc gac tgc gac         816
Asp Cys Gly Gly Thr Tyr Ser Ala Thr Arg Tyr Ala Gly Asp Cys Asp
```

```
                    260                 265                 270
ccc gac gga tgc gac ttc aac tcg tac cgc cag ggc gtc aag gac ttc          864
Pro Asp Gly Cys Asp Phe Asn Ser Tyr Arg Gln Gly Val Lys Asp Phe
            275                 280                 285 tac ggg ccc ggc atg acc gtc gac agc aac tcg gtc gtc acc gtc gtc          912
Tyr Gly Pro Gly Met Thr Val Asp Ser Asn Ser Val Val Thr Val Val
        290                 295                 300 acg cag ttc atc acc aac gac ggc acc gcg tcc ggc acc ctc tcc gag          960
Thr Gln Phe Ile Thr Asn Asp Gly Thr Ala Ser Gly Thr Leu Ser Glu
305                 310                 315                 320 atc aag cgc ttc tac gtc cag aac ggc aag gtt atc ccc aac tcc gag         1008
Ile Lys Arg Phe Tyr Val Gln Asn Gly Lys Val Ile Pro Asn Ser Glu
                325                 330                 335 tcc acc atc gcc ggc gtc agc ggc aac agc atc acc tcc gcg tac tgc         1056
Ser Thr Ile Ala Gly Val Ser Gly Asn Ser Ile Thr Ser Ala Tyr Cys
            340                 345                 350 gac gcg cag aag gag gtc ttc ggc gac aac acg tcg ttc cag gac cag         1104
Asp Ala Gln Lys Glu Val Phe Gly Asp Asn Thr Ser Phe Gln Asp Gln
        355                 360                 365 ggc ggc ttg gcc agc atg agc cag gcc ctc aac gcc ggc atg gtc ctc         1152
Gly Gly Leu Ala Ser Met Ser Gln Ala Leu Asn Ala Gly Met Val Leu
370                 375                 380 gtc atg tcc atc tgg gac gac cac cac agc aac atg ctc tgg ctc gac         1200
Val Met Ser Ile Trp Asp Asp His His Ser Asn Met Leu Trp Leu Asp
385                 390                 395                 400 tcc gac tac ccc gtc gac gcc gac ccg agc cag ccc ggc atc tcc cgc         1248
Ser Asp Tyr Pro Val Asp Ala Asp Pro Ser Gln Pro Gly Ile Ser Arg
                405                 410                 415 ggt act tgc ccc acc acc tct ggt gtc ccc agc gag gtt gag gag agc         1296
Gly Thr Cys Pro Thr Thr Ser Gly Val Pro Ser Glu Val Glu Glu Ser
            420                 425                 430 gcc gct agc gcc tac gtc gtc tac tcg aac att aag gtt ggt gac ctt         1344
Ala Ala Ser Ala Tyr Val Val Tyr Ser Asn Ile Lys Val Gly Asp Leu
        435                 440                 445 aac agc act ttc tct gct tag                                             1365
Asn Ser Thr Phe Ser Ala
    450

<210> SEQ ID NO 38
<211> LENGTH: 454
<212> TYPE: PRT
<213> ORGANISM: Diplodia gossypina

<400> SEQUENCE: 38

Met Leu Thr Gln Ala Val Leu Ala Thr Leu Ala Thr Leu Ala Leu Ala Ser
1               5                   10                  15

Gln Gln Val Gly Thr Gln Lys Glu Val His Pro Ser Met Thr Trp
            20                  25                  30

Gln Thr Cys Thr Ser Ser Gly Cys Thr Thr Asn Gln Gly Ser Ile Val
        35                  40                  45

Val Asp Ala Asn Trp Arg Trp Val His Asn Thr Glu Gly Tyr Thr Asn
    50                  55                  60

Cys Tyr Thr Gly Asn Thr Trp Asn Ala Asp Tyr Cys Thr Asp Asn Thr
65                  70                  75                  80

Glu Cys Ala Ser Asn Cys Ala Leu Asp Gly Ala Asp Tyr Ser Gly Thr
                85                  90                  95

Tyr Gly Ala Thr Thr Ser Gly Asp Ser Leu Arg Leu Asn Phe Ile Thr
            100                 105                 110
```

Asn Gly Gln Gln Lys Asn Ile Gly Ser Arg Met Tyr Leu Met Gln Asp
            115                 120                 125

Asp Glu Thr Tyr Ala Val His Lys Leu Leu Asn Lys Glu Phe Thr Phe
        130                 135                 140

Asp Val Asp Thr Ser Lys Leu Pro Cys Gly Leu Asn Gly Ala Val Tyr
145                 150                 155                 160

Phe Val Ser Met Asp Ala Asp Gly Met Ala Lys Phe Pro Asp Asn
                165                 170                 175

Lys Ala Gly Ala Lys Tyr Gly Thr Gly Tyr Cys Asp Ser Gln Cys Pro
                180                 185                 190

Arg Asp Leu Lys Phe Ile Asp Gly Lys Ala Asn Val Glu Gly Trp Val
            195                 200                 205

Pro Ser Glu Asn Asp Ser Asn Ala Gly Val Gly Asn Leu Gly Ser Cys
    210                 215                 220

Cys Ala Glu Met Asp Ile Trp Glu Ala Asn Ser Ile Ser Thr Ala Tyr
225                 230                 235                 240

Thr Pro His Ser Cys Lys Thr Val Ala Gln His Ser Cys Thr Gly Asp
                245                 250                 255

Asp Cys Gly Gly Thr Tyr Ser Ala Thr Arg Tyr Ala Gly Asp Cys Asp
                260                 265                 270

Pro Asp Gly Cys Asp Phe Asn Ser Tyr Arg Gln Gly Val Lys Asp Phe
            275                 280                 285

Tyr Gly Pro Gly Met Thr Val Asp Ser Asn Ser Val Thr Val Val
    290                 295                 300

Thr Gln Phe Ile Thr Asn Asp Gly Thr Ala Ser Gly Thr Leu Ser Glu
305                 310                 315                 320

Ile Lys Arg Phe Tyr Val Gln Asn Gly Lys Val Ile Pro Asn Ser Glu
                325                 330                 335

Ser Thr Ile Ala Gly Val Ser Gly Asn Ser Ile Thr Ser Ala Tyr Cys
                340                 345                 350

Asp Ala Gln Lys Glu Val Phe Gly Asp Asn Thr Ser Phe Gln Asp Gln
            355                 360                 365

Gly Gly Leu Ala Ser Met Ser Gln Ala Leu Asn Ala Gly Met Val Leu
    370                 375                 380

Val Met Ser Ile Trp Asp Asp His His Ser Asn Met Leu Trp Leu Asp
385                 390                 395                 400

Ser Asp Tyr Pro Val Asp Ala Asp Pro Ser Gln Pro Gly Ile Ser Arg
                405                 410                 415

Gly Thr Cys Pro Thr Thr Ser Gly Val Pro Ser Glu Val Glu Glu Ser
                420                 425                 430

Ala Ala Ser Ala Tyr Val Val Tyr Ser Asn Ile Lys Val Gly Asp Leu
            435                 440                 445

Asn Ser Thr Phe Ser Ala
    450

<210> SEQ ID NO 39
<211> LENGTH: 1377
<212> TYPE: DNA
<213> ORGANISM: Trichophaea saccata
<220> FEATURE:
<221> NAME/KEY: CDS
<222> LOCATION: (1)..(1377)

<400> SEQUENCE: 39 atg caa cgc ctt ctc gtt ctt ctc acc tcc ctt ctc gct ttc acc tat       48
Met Gln Arg Leu Leu Val Leu Leu Thr Ser Leu Leu Ala Phe Thr Tyr -continued

```
1               5                  10                 15
ggc caa caa gtt ggc act caa cag gcc gaa gtc cac ccc tcg atg acc    96
Gly Gln Gln Val Gly Thr Gln Gln Ala Glu Val His Pro Ser Met Thr
             20                  25                  30 tgg cag cag tgt aca aag tcc ggc ggc tgc acc acg aag aac ggc aaa   144
Trp Gln Gln Cys Thr Lys Ser Gly Gly Cys Thr Thr Lys Asn Gly Lys
         35                  40                  45 gtc gtg atc gat gcc aac tgg cgt tgg gta cac aat gtc ggc ggc tac   192
Val Val Ile Asp Ala Asn Trp Arg Trp Val His Asn Val Gly Gly Tyr
     50                  55                  60 acc aat tgc tac act ggc aac acc tgg gac agt tcg ctt tgt ccc gac   240
Thr Asn Cys Tyr Thr Gly Asn Thr Trp Asp Ser Ser Leu Cys Pro Asp
65                  70                  75                  80 gat gtc acc tgc gcg aag aat tgc gct ctt gat ggc gcg gac tac tct   288
Asp Val Thr Cys Ala Lys Asn Cys Ala Leu Asp Gly Ala Asp Tyr Ser
                 85                  90                  95 ggc act tat gga gtt act gcg ggc ggg aat tcg ttg aag ctc acc ttc   336
Gly Thr Tyr Gly Val Thr Ala Gly Gly Asn Ser Leu Lys Leu Thr Phe
             100                 105                 110 gtc act aag ggt caa tac tct act aat gtg ggc tcg cga ttg tat atg   384
Val Thr Lys Gly Gln Tyr Ser Thr Asn Val Gly Ser Arg Leu Tyr Met
         115                 120                 125 ctc gcc gac gac agc aca tac cag atg tat aat ctg ctg aac cag gag   432
Leu Ala Asp Asp Ser Thr Tyr Gln Met Tyr Asn Leu Leu Asn Gln Glu
     130                 135                 140 ttt acg ttc gac gtt gat gtt tct aat ctt cct tgt ggg ctt aac ggg   480
Phe Thr Phe Asp Val Asp Val Ser Asn Leu Pro Cys Gly Leu Asn Gly
145                 150                 155                 160 gct ctg tat ttc gtc tcg atg gat aag gat ggt ggg atg tcg aag tac   528
Ala Leu Tyr Phe Val Ser Met Asp Lys Asp Gly Gly Met Ser Lys Tyr
                 165                 170                 175 tct ggg aac aag gct ggt gcc aag tat gga act ggg tac tgc gac tcc   576
Ser Gly Asn Lys Ala Gly Ala Lys Tyr Gly Thr Gly Tyr Cys Asp Ser
             180                 185                 190 cag tgt ccc cgc gat ctc aag ttc atc aat gga cag ggc aac gtt gaa   624
Gln Cys Pro Arg Asp Leu Lys Phe Ile Asn Gly Gln Gly Asn Val Glu
         195                 200                 205 ggc tgg aag cca tcc tca aat gat gcc aac gca ggc gtc ggg gga cac   672
Gly Trp Lys Pro Ser Ser Asn Asp Ala Asn Ala Gly Val Gly Gly His
     210                 215                 220 ggt tcc tgc tgc gca gag atg gat gtt tgg gag gcc aat tcc atc tcc   720
Gly Ser Cys Cys Ala Glu Met Asp Val Trp Glu Ala Asn Ser Ile Ser
225                 230                 235                 240 gcg gcc gta aca ccg cac tcg tgc tcc aca acc agc cag acg atg tgc   768
Ala Ala Val Thr Pro His Ser Cys Ser Thr Thr Ser Gln Thr Met Cys
                 245                 250                 255 aac ggc gac tcc tgc ggc ggt acc tac tca gcc aca cga tac gct ggt   816
Asn Gly Asp Ser Cys Gly Gly Thr Tyr Ser Ala Thr Arg Tyr Ala Gly
             260                 265                 270 gtc tgc gat ccc gat ggc tgc gac ttc aac tcc tac cgt atg ggc gac   864
Val Cys Asp Pro Asp Gly Cys Asp Phe Asn Ser Tyr Arg Met Gly Asp
         275                 280                 285 acg acc ttc tac ggc aag gga aag acg gtc gat acc agc tcc aag ttc   912
Thr Thr Phe Tyr Gly Lys Gly Lys Thr Val Asp Thr Ser Ser Lys Phe
     290                 295                 300 acg gtc gtg acc cag ttc atc acc gac act gga acc gcc tcc ggc tcg   960
Thr Val Val Thr Gln Phe Ile Thr Asp Thr Gly Thr Ala Ser Gly Ser
305                 310                 315                 320 ctc acg gag atc cgc cgc ttc tac gtc cag aac gga aag ttg atc ccc  1008
```

| | | | | | | | | | | | | |
|---|---|---|---|---|---|---|---|---|---|---|---|---|
| Leu | Thr | Glu | Ile | Arg<br>325 | Arg | Phe | Tyr | Val<br>330 | Gln | Asn | Gly | Lys | Leu<br>335 | Ile | Pro |

```
aac tcc cag tcg aag atc tcg ggc gtc act ggc aac tcc atc acc tct      1056
Asn Ser Gln Ser Lys Ile Ser Gly Val Thr Gly Asn Ser Ile Thr Ser
        340                 345                 350 gct ttc tgc gac gct cag aag gcg gct ttc ggc gat aac tac acg ttc      1104
Ala Phe Cys Asp Ala Gln Lys Ala Ala Phe Gly Asp Asn Tyr Thr Phe
            355                 360                 365 aag gac aag ggc ggc ttc gca tcc atg act act gct atg aag aac gga      1152
Lys Asp Lys Gly Gly Phe Ala Ser Met Thr Thr Ala Met Lys Asn Gly
    370                 375                 380 atg gtc ctg gtt atg agt ctt tgg gat gac cac tac gcc aat atg ctc      1200
Met Val Leu Val Met Ser Leu Trp Asp Asp His Tyr Ala Asn Met Leu
385                 390                 395                 400 tgg ctt gat agc gac tat ccc act aac gcg gac tcc tcc aag ccg ggt      1248
Trp Leu Asp Ser Asp Tyr Pro Thr Asn Ala Asp Ser Ser Lys Pro Gly
                405                 410                 415 gtt gct cgt ggc acc tgc ccg act tct tcc ggc gtg ccc tcg gat gtc      1296
Val Ala Arg Gly Thr Cys Pro Thr Ser Ser Gly Val Pro Ser Asp Val
            420                 425                 430 gag act aac aat gca agc gct tcg gtc acg tac tcc aac att aga ttt      1344
Glu Thr Asn Asn Ala Ser Ala Ser Val Thr Tyr Ser Asn Ile Arg Phe
    435                 440                 445 gga gat ctc aat tcc act tac acc gcc cag taa                          1377
Gly Asp Leu Asn Ser Thr Tyr Thr Ala Gln
    450                 455

<210> SEQ ID NO 40
<211> LENGTH: 458
<212> TYPE: PRT
<213> ORGANISM: Trichophaea saccata

<400> SEQUENCE: 40

Met Gln Arg Leu Leu Val Leu Thr Ser Leu Leu Ala Phe Thr Tyr
1               5                   10                  15

Gly Gln Gln Val Gly Thr Gln Ala Glu Val His Pro Ser Met Thr
                20                  25                  30

Trp Gln Gln Cys Thr Lys Ser Gly Gly Cys Thr Thr Lys Asn Gly Lys
        35                  40                  45

Val Val Ile Asp Ala Asn Trp Arg Trp Val His Asn Val Gly Gly Tyr
    50                  55                  60

Thr Asn Cys Tyr Thr Gly Asn Thr Trp Asp Ser Ser Leu Cys Pro Asp
65                  70                  75                  80

Asp Val Thr Cys Ala Lys Asn Cys Ala Leu Asp Gly Ala Asp Tyr Ser
                85                  90                  95

Gly Thr Tyr Gly Val Thr Ala Gly Gly Asn Ser Leu Lys Leu Thr Phe
                100                 105                 110

Val Thr Lys Gly Gln Tyr Ser Thr Asn Val Gly Ser Arg Leu Tyr Met
        115                 120                 125

Leu Ala Asp Asp Ser Thr Tyr Gln Met Tyr Asn Leu Leu Asn Gln Glu
    130                 135                 140

Phe Thr Phe Asp Val Asp Val Ser Asn Leu Pro Cys Gly Leu Asn Gly
145                 150                 155                 160

Ala Leu Tyr Phe Val Ser Met Asp Lys Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190
```

```
Gln Cys Pro Arg Asp Leu Lys Phe Ile Asn Gly Gln Gly Asn Val Glu
            195                 200                 205

Gly Trp Lys Pro Ser Ser Asn Asp Ala Asn Ala Gly Val Gly Gly His
    210                 215                 220

Gly Ser Cys Cys Ala Glu Met Asp Val Trp Glu Ala Asn Ser Ile Ser
225                 230                 235                 240

Ala Ala Val Thr Pro His Ser Cys Ser Thr Thr Ser Gln Thr Met Cys
                245                 250                 255

Asn Gly Asp Ser Cys Gly Gly Thr Tyr Ser Ala Thr Arg Tyr Ala Gly
            260                 265                 270

Val Cys Asp Pro Asp Gly Cys Asp Phe Asn Ser Tyr Arg Met Gly Asp
            275                 280                 285

Thr Thr Phe Tyr Gly Lys Gly Lys Thr Val Asp Thr Ser Ser Lys Phe
        290                 295                 300

Thr Val Val Thr Gln Phe Ile Thr Asp Thr Gly Thr Ala Ser Gly Ser
305                 310                 315                 320

Leu Thr Glu Ile Arg Arg Phe Tyr Val Gln Asn Gly Lys Leu Ile Pro
                325                 330                 335

Asn Ser Gln Ser Lys Ile Ser Gly Val Thr Gly Asn Ser Ile Thr Ser
            340                 345                 350

Ala Phe Cys Asp Ala Gln Lys Ala Ala Phe Gly Asp Asn Tyr Thr Phe
        355                 360                 365

Lys Asp Lys Gly Gly Phe Ala Ser Met Thr Thr Ala Met Lys Asn Gly
    370                 375                 380

Met Val Leu Val Met Ser Leu Trp Asp Asp His Tyr Ala Asn Met Leu
385                 390                 395                 400

Trp Leu Asp Ser Asp Tyr Pro Thr Asn Ala Asp Ser Ser Lys Pro Gly
                405                 410                 415

Val Ala Arg Gly Thr Cys Pro Thr Ser Ser Gly Val Pro Ser Asp Val
            420                 425                 430

Glu Thr Asn Asn Ala Ser Ala Ser Val Thr Tyr Ser Asn Ile Arg Phe
        435                 440                 445

Gly Asp Leu Asn Ser Thr Tyr Thr Ala Gln
    450                 455
```

<210> SEQ ID NO 41
<211> LENGTH: 1353
<212> TYPE: DNA
<213> ORGANISM: Myceliophthora thermophila
<220> FEATURE:
<221> NAME/KEY: CDS
<222> LOCATION: (1)..(1353)

<400> SEQUENCE: 41

```
atg aag cag tac ctc cag tac ctc gcg gcg acc ctg ccc ctg gtg ggc      48
Met Lys Gln Tyr Leu Gln Tyr Leu Ala Ala Thr Leu Pro Leu Val Gly
1               5                   10                  15 ctg gcc acg gcc cag cag gcg ggt aac ctg cag acc gag act cac ccc      96
Leu Ala Thr Ala Gln Gln Ala Gly Asn Leu Gln Thr Glu Thr His Pro
            20                  25                  30 agg ctc act tgg tcc aag tgc acg gcc ccg gga tcc tgc caa cag gtc     144
Arg Leu Thr Trp Ser Lys Cys Thr Ala Pro Gly Ser Cys Gln Gln Val
        35                  40                  45 aac ggc gag gtc gtc atc gac tcc aac tgg cgc tgg gtg cac gac gag     192
Asn Gly Glu Val Val Ile Asp Ser Asn Trp Arg Trp Val His Asp Glu
    50                  55                  60 aac gcg cag aac tgc tac gac ggc aac cag tgg acc aac gct tgc agc     240
```

```
                                                              -continued
Asn Ala Gln Asn Cys Tyr Asp Gly Asn Gln Trp Thr Asn Ala Cys Ser
 65              70                  75                  80 tct gcc acc gac tgc gcc gag aat tgc gcg ctc gag ggt gcc gac tac        288
Ser Ala Thr Asp Cys Ala Glu Asn Cys Ala Leu Glu Gly Ala Asp Tyr
                 85                  90                  95 cag ggc acc tat ggc gcc tcg acc agc ggc aat gcc ctg acg ctc acc        336
Gln Gly Thr Tyr Gly Ala Ser Thr Ser Gly Asn Ala Leu Thr Leu Thr
            100                 105                 110 ttc gtc act aag cac gag tac ggc acc aac att ggc tcg cgc ctc tac        384
Phe Val Thr Lys His Glu Tyr Gly Thr Asn Ile Gly Ser Arg Leu Tyr
        115                 120                 125 ctc atg aac ggc gcg aac aag tac cag atg ttc acc ctc aag ggc aac        432
Leu Met Asn Gly Ala Asn Lys Tyr Gln Met Phe Thr Leu Lys Gly Asn
    130                 135                 140 gag ctg gcc ttc gac gtc gac ctc tcg gcc gtc gag tgc ggc ctc aac        480
Glu Leu Ala Phe Asp Val Asp Leu Ser Ala Val Glu Cys Gly Leu Asn
145                 150                 155                 160 agc gcc ctc tac ttc gtg gcc atg gag gag gat ggc ggt gtg tcg agc        528
Ser Ala Leu Tyr Phe Val Ala Met Glu Glu Asp Gly Gly Val Ser Ser
                165                 170                 175 tac ccg acc aac acg gcc ggt gct aag ttc ggc act ggg tac tgc gac        576
Tyr Pro Thr Asn Thr Ala Gly Ala Lys Phe Gly Thr Gly Tyr Cys Asp
            180                 185                 190 gcc caa tgc gca cgc gac ctc aag ttc gtc ggc ggc aag ggc aac atc        624
Ala Gln Cys Ala Arg Asp Leu Lys Phe Val Gly Gly Lys Gly Asn Ile
        195                 200                 205 gag ggc tgg aag ccg tcc acc aac gat gcc aat gcc ggt gtc ggt cct        672
Glu Gly Trp Lys Pro Ser Thr Asn Asp Ala Asn Ala Gly Val Gly Pro
    210                 215                 220 tat ggc ggg tgc tgc gct gag atc gac gtc tgg gag tcg aac aag tat        720
Tyr Gly Gly Cys Cys Ala Glu Ile Asp Val Trp Glu Ser Asn Lys Tyr
225                 230                 235                 240 gct ttc gct ttc acc ccg cac ggt tgc gag aac cct aaa tac cac gtc        768
Ala Phe Ala Phe Thr Pro His Gly Cys Glu Asn Pro Lys Tyr His Val
                245                 250                 255 tgc gag acc acc aac tgc ggt ggc acc tac tcc gag gac cgc ttc gct        816
Cys Glu Thr Thr Asn Cys Gly Gly Thr Tyr Ser Glu Asp Arg Phe Ala
            260                 265                 270 ggt gac tgc gat gcc aac ggc tgc gac tac aac ccc tac cgc atg ggc        864
Gly Asp Cys Asp Ala Asn Gly Cys Asp Tyr Asn Pro Tyr Arg Met Gly
        275                 280                 285 aac cag gac ttc tac ggt ccc ggc ttg acg gtc gat acc agc aag aag        912
Asn Gln Asp Phe Tyr Gly Pro Gly Leu Thr Val Asp Thr Ser Lys Lys
    290                 295                 300 ttc acc gtc gtc agc cag ttc gag gag aac aag ctc acc cag ttc ttc        960
Phe Thr Val Val Ser Gln Phe Glu Glu Asn Lys Leu Thr Gln Phe Phe
305                 310                 315                 320 gtc cag gac ggc aag aag att gag atc ccc ggc ccc aag gtc gag ggc       1008
Val Gln Asp Gly Lys Lys Ile Glu Ile Pro Gly Pro Lys Val Glu Gly
                325                 330                 335 atc gat gcg gac agc gcc gct atc acc cct gag ctg tgc agt gcc ctg       1056
Ile Asp Ala Asp Ser Ala Ala Ile Thr Pro Glu Leu Cys Ser Ala Leu
            340                 345                 350 ttc aag gcc ttc gat gac cgt gac cgc ttc tcg gag gtt ggc ggc ttc       1104
Phe Lys Ala Phe Asp Asp Arg Asp Arg Phe Ser Glu Val Gly Gly Phe
        355                 360                 365 gat gcc atc aac acg gcc ctc agc act ccc atg gtc ctc gtc atg tcc       1152
Asp Ala Ile Asn Thr Ala Leu Ser Thr Pro Met Val Leu Val Met Ser
    370                 375                 380
```

```
atc tgg gat gat cac tac gcc aat atg ctc tgg ctc gac tcg agc tac    1200
Ile Trp Asp Asp His Tyr Ala Asn Met Leu Trp Leu Asp Ser Ser Tyr
385             390                 395                 400 ccc cct gag aag gct ggc cag cct ggc ggt gac cgt ggc ccg tgt cct    1248
Pro Pro Glu Lys Ala Gly Gln Pro Gly Gly Asp Arg Gly Pro Cys Pro
        405                 410                 415 cag gac tct ggc gtc ccg gcc gac gtt gag gct cag tac cct aat gcc    1296
Gln Asp Ser Gly Val Pro Ala Asp Val Glu Ala Gln Tyr Pro Asn Ala
            420                 425                 430 aag gtc atc tgg tcc aac atc cgc ttc ggc ccc atc ggc tcg act gtc    1344
Lys Val Ile Trp Ser Asn Ile Arg Phe Gly Pro Ile Gly Ser Thr Val
                435                 440                 445 aac gtc taa                                                        1353
Asn Val
    450

<210> SEQ ID NO 42
<211> LENGTH: 450
<212> TYPE: PRT
<213> ORGANISM: Myceliophthora thermophila

<400> SEQUENCE: 42

Met Lys Gln Tyr Leu Gln Tyr Leu Ala Ala Thr Leu Pro Leu Val Gly
1               5                   10                  15

Leu Ala Thr Ala Gln Gln Ala Gly Asn Leu Gln Thr Glu Thr His Pro
            20                  25                  30

Arg Leu Thr Trp Ser Lys Cys Thr Ala Pro Gly Ser Cys Gln Gln Val
        35                  40                  45

Asn Gly Glu Val Val Ile Asp Ser Asn Trp Arg Trp Val His Asp Glu
    50                  55                  60

Asn Ala Gln Asn Cys Tyr Asp Gly Asn Gln Trp Thr Asn Ala Cys Ser
65                  70                  75                  80

Ser Ala Thr Asp Cys Ala Glu Asn Cys Ala Leu Glu Gly Ala Asp Tyr
                85                  90                  95

Gln Gly Thr Tyr Gly Ala Ser Thr Ser Gly Asn Ala Leu Thr Leu Thr
            100                 105                 110

Phe Val Thr Lys His Glu Tyr Gly Thr Asn Ile Gly Ser Arg Leu Tyr
        115                 120                 125

Leu Met Asn Gly Ala Asn Lys Tyr Gln Met Phe Thr Leu Lys Gly Asn
    130                 135                 140

Glu Leu Ala Phe Asp Val Asp Leu Ser Ala Val Glu Cys Gly Leu Asn
145                 150                 155                 160

Ser Ala Leu Tyr Phe Val Ala Met Glu Glu Asp Gly Gly Val Ser Ser
                165                 170                 175

Tyr Pro Asn Thr Ala Gly Ala Lys Phe Gly Thr Gly Tyr Cys Asp
            180                 185                 190

Ala Gln Cys Ala Arg Asp Leu Lys Phe Val Gly Gly Lys Gly Asn Ile
        195                 200                 205

Glu Gly Trp Lys Pro Ser Thr Asn Asp Ala Asn Ala Gly Val Gly Pro
    210                 215                 220

Tyr Gly Gly Cys Cys Ala Glu Ile Asp Val Trp Glu Ser Asn Lys Tyr
225                 230                 235                 240

Ala Phe Ala Phe Thr Pro His Gly Cys Glu Asn Pro Lys Tyr His Val
                245                 250                 255

Cys Glu Thr Thr Asn Cys Gly Gly Thr Tyr Ser Glu Asp Arg Phe Ala
            260                 265                 270
```

```
Gly Asp Cys Asp Ala Asn Gly Cys Asp Tyr Asn Pro Tyr Arg Met Gly
            275                 280                 285

Asn Gln Asp Phe Tyr Gly Pro Gly Leu Thr Val Asp Thr Ser Lys Lys
    290                 295                 300

Phe Thr Val Val Ser Gln Phe Glu Glu Asn Lys Leu Thr Gln Phe Phe
305                 310                 315                 320

Val Gln Asp Gly Lys Lys Ile Glu Ile Pro Gly Pro Lys Val Glu Gly
                325                 330                 335

Ile Asp Ala Asp Ser Ala Ala Ile Thr Pro Glu Leu Cys Ser Ala Leu
            340                 345                 350

Phe Lys Ala Phe Asp Asp Arg Asp Arg Phe Ser Glu Val Gly Gly Phe
        355                 360                 365

Asp Ala Ile Asn Thr Ala Leu Ser Thr Pro Met Val Leu Val Met Ser
    370                 375                 380

Ile Trp Asp Asp His Tyr Ala Asn Met Leu Trp Leu Asp Ser Ser Tyr
385                 390                 395                 400

Pro Pro Glu Lys Ala Gly Gln Pro Gly Gly Asp Arg Gly Pro Cys Pro
                405                 410                 415

Gln Asp Ser Gly Val Pro Ala Asp Val Glu Ala Gln Tyr Pro Asn Ala
            420                 425                 430

Lys Val Ile Trp Ser Asn Ile Arg Phe Gly Pro Ile Gly Ser Thr Val
        435                 440                 445

Asn Val
    450

<210> SEQ ID NO 43
<211> LENGTH: 1341
<212> TYPE: DNA
<213> ORGANISM: Xylaria hypoxylon
<220> FEATURE:
<221> NAME/KEY: CDS
<222> LOCATION: (1)..(1341)

<400> SEQUENCE: 43 atg ttg tcc ctc gcc gtg tcg gcc gcc ctt ctc ggg ctc gcg tct gcc      48
Met Leu Ser Leu Ala Val Ser Ala Ala Leu Leu Gly Leu Ala Ser Ala
1               5                   10                  15 cag cag gtt gga aag gag caa tct gag act cac cct aag ctg tct tgg      96
Gln Gln Val Gly Lys Glu Gln Ser Glu Thr His Pro Lys Leu Ser Trp
            20                  25                  30 aag aag tgc acc agc ggt ggt tcc tgc acc cag acc aac gct gag gtg     144
Lys Lys Cys Thr Ser Gly Gly Ser Cys Thr Gln Thr Asn Ala Glu Val
        35                  40                  45 acc atc gac tct aac tgg cga tgg ctt cac tct ctc gaa ggc act gag     192
Thr Ile Asp Ser Asn Trp Arg Trp Leu His Ser Leu Glu Gly Thr Glu
    50                  55                  60 aac tgc tac gat ggt aac aag tgg acc tcg cag tgc agc act ggc gag     240
Asn Cys Tyr Asp Gly Asn Lys Trp Thr Ser Gln Cys Ser Thr Gly Glu
65                  70                  75                  80 gac tgc gcc acc aag tgc gcc atc gag ggt gcc gac tac agc aag acc     288
Asp Cys Ala Thr Lys Cys Ala Ile Glu Gly Ala Asp Tyr Ser Lys Thr
                85                  90                  95 tac ggt gcc tct act agc ggc gat gct ctt acc ctc aag ttc ctg acc     336
Tyr Gly Ala Ser Thr Ser Gly Asp Ala Leu Thr Leu Lys Phe Leu Thr
            100                 105                 110 aag cac gag tac gga acc aac atc ggc tcc cga ttc tac ctt atg aat     384
Lys His Glu Tyr Gly Thr Asn Ile Gly Ser Arg Phe Tyr Leu Met Asn
        115                 120                 125
```

| | | |
|---|---|---|
| ggt gcc gac aag tac cag acc ttc gac ctc aag ggt aac gag ttc acc<br>Gly Ala Asp Lys Tyr Gln Thr Phe Asp Leu Lys Gly Asn Glu Phe Thr<br>130                   135                  140 | | 432 |
| ttc gat gtc gac ctg tcc acc gtc gac tgt ggt ctt aac gcc gct ctt<br>Phe Asp Val Asp Leu Ser Thr Val Asp Cys Gly Leu Asn Ala Ala Leu<br>145                   150                  155                 160 | | 480 |
| tac ttc gtc gcc atg gag gaa gac ggt ggc atg gct agc tac ccc aac<br>Tyr Phe Val Ala Met Glu Glu Asp Gly Gly Met Ala Ser Tyr Pro Asn<br>                  165                  170                  175 | | 528 |
| aac aag gcc ggt gcc aag tac ggt acc ggt tac tgt gac gct cag tgt<br>Asn Lys Ala Gly Ala Lys Tyr Gly Thr Gly Tyr Cys Asp Ala Gln Cys<br>                  180                  185                  190 | | 576 |
| gcc cgt gac ttg aag ttc gtc ggt ggc aag ggc aac gtt gag gga tgg<br>Ala Arg Asp Leu Lys Phe Val Gly Gly Lys Gly Asn Val Glu Gly Trp<br>                195                  200                  205 | | 624 |
| gag cca tcc acc aac gac gac aac gcc ggt gtt ggc cct tac ggt gcc<br>Glu Pro Ser Thr Asn Asp Asp Asn Ala Gly Val Gly Pro Tyr Gly Ala<br>210                   215                  220 | | 672 |
| tgc tgt gcc gaa atc gat gtc tgg gag tcc aac tct cac tct ttc gct<br>Cys Cys Ala Glu Ile Asp Val Trp Glu Ser Asn Ser His Ser Phe Ala<br>225                   230                  235                 240 | | 720 |
| ttc acc cct cac cct tgc acc acc aac gaa tac cac gtc tgt gag cag<br>Phe Thr Pro His Pro Cys Thr Thr Asn Glu Tyr His Val Cys Glu Gln<br>                  245                  250                  255 | | 768 |
| gac gag tgt ggt ggt acc tac tct gag gac cga ttc gct ggc aag tgt<br>Asp Glu Cys Gly Gly Thr Tyr Ser Glu Asp Arg Phe Ala Gly Lys Cys<br>                  260                  265                  270 | | 816 |
| gat gcc aac ggt tgt gac tac aac cct tac cgc atg ggt aac acc gac<br>Asp Ala Asn Gly Cys Asp Tyr Asn Pro Tyr Arg Met Gly Asn Thr Asp<br>                  275                  280                  285 | | 864 |
| ttc tac ggc cag ggc aag acc gtc gac acc agc aag aaa ttc act gtt<br>Phe Tyr Gly Gln Gly Lys Thr Val Asp Thr Ser Lys Lys Phe Thr Val<br>                290                  295                  300 | | 912 |
| gtc acc cag ttc gcc gaa aac aag ttg act cag ttc ttc gtc cag gac<br>Val Thr Gln Phe Ala Glu Asn Lys Leu Thr Gln Phe Phe Val Gln Asp<br>305                   310                  315                 320 | | 960 |
| ggt aag aag att gag atc ccc ggt ccc aag att gac ggt ttc cct acc<br>Gly Lys Lys Ile Glu Ile Pro Gly Pro Lys Ile Asp Gly Phe Pro Thr<br>                  325                  330                  335 | | 1008 |
| gat agc gcc atc acc ccc gag tac tgc act gcc gaa ttc aac gtt cta<br>Asp Ser Ala Ile Thr Pro Glu Tyr Cys Thr Ala Glu Phe Asn Val Leu<br>                  340                  345                  350 | | 1056 |
| gga gac cgt gac cgc ttc agt gaa gtt ggt ggc ttc gac cag ctc aac<br>Gly Asp Arg Asp Arg Phe Ser Glu Val Gly Gly Phe Asp Gln Leu Asn<br>                  355                  360                  365 | | 1104 |
| aac gct ctt gac gta ccc atg gtc ctt gtc atg tcc atc tgg gac gac<br>Asn Ala Leu Asp Val Pro Met Val Leu Val Met Ser Ile Trp Asp Asp<br>370                   375                  380 | | 1152 |
| cac tac gcc aac atg ctt tgg ctc gac tcc agc tac ccc cct gag aag<br>His Tyr Ala Asn Met Leu Trp Leu Asp Ser Ser Tyr Pro Pro Glu Lys<br>385                   390                  395                 400 | | 1200 |
| gct ggc cag ccc ggt ggt gac cgt ggt gac tgt gcc ccc gac tcc ggt<br>Ala Gly Gln Pro Gly Gly Asp Arg Gly Asp Cys Ala Pro Asp Ser Gly<br>                  405                  410                  415 | | 1248 |
| gtc ccc tcc gac gtc gag gcc agc atc ccc gat gcc aag gtc gtc tgg<br>Val Pro Ser Asp Val Glu Ala Ser Ile Pro Asp Ala Lys Val Val Trp<br>                  420                  425                  430 | | 1296 |
| tcc aac atc cgc ttc ggt ccc atc ggc tct act gtc gag gtt taa<br>Ser Asn Ile Arg Phe Gly Pro Ile Gly Ser Thr Val Glu Val<br>                  435                  440                  445 | | 1341 |

<210> SEQ ID NO 44
<211> LENGTH: 446
<212> TYPE: PRT
<213> ORGANISM: Xylaria hypoxylon

<400> SEQUENCE: 44

```
Met Leu Ser Leu Ala Val Ser Ala Ala Leu Gly Leu Ala Ser Ala
1               5                   10                  15

Gln Gln Val Gly Lys Glu Gln Ser Glu Thr His Pro Lys Leu Ser Trp
            20                  25                  30

Lys Lys Cys Thr Ser Gly Gly Ser Cys Thr Gln Thr Asn Ala Glu Val
        35                  40                  45

Thr Ile Asp Ser Asn Trp Arg Trp Leu His Ser Leu Glu Gly Thr Glu
    50                  55                  60

Asn Cys Tyr Asp Gly Asn Lys Trp Thr Ser Gln Cys Ser Thr Gly Glu
65                  70                  75                  80

Asp Cys Ala Thr Lys Cys Ala Ile Glu Gly Ala Asp Tyr Ser Lys Thr
                85                  90                  95

Tyr Gly Ala Ser Thr Ser Gly Asp Ala Leu Thr Leu Lys Phe Leu Thr
            100                 105                 110

Lys His Glu Tyr Gly Thr Asn Ile Gly Ser Arg Phe Tyr Leu Met Asn
        115                 120                 125

Gly Ala Asp Lys Tyr Gln Thr Phe Asp Leu Lys Gly Asn Glu Phe Thr
    130                 135                 140

Phe Asp Val Asp Leu Ser Thr Val Asp Cys Gly Leu Asn Ala Ala Leu
145                 150                 155                 160

Tyr Phe Val Ala Met Glu Glu Asp Gly Gly Met Ala Ser Tyr Pro Asn
                165                 170                 175

Asn Lys Ala Gly Ala Lys Tyr Gly Thr Gly Tyr Cys Asp Ala Gln Cys
            180                 185                 190

Ala Arg Asp Leu Lys Phe Val Gly Gly Lys Gly Asn Val Glu Gly Trp
        195                 200                 205

Glu Pro Ser Thr Asn Asp Asp Asn Ala Gly Val Gly Pro Tyr Gly Ala
    210                 215                 220

Cys Cys Ala Glu Ile Asp Val Trp Glu Ser Asn Ser His Ser Phe Ala
225                 230                 235                 240

Phe Thr Pro His Pro Cys Thr Thr Asn Glu Tyr His Val Cys Glu Gln
                245                 250                 255

Asp Glu Cys Gly Gly Thr Tyr Ser Glu Asp Arg Phe Ala Gly Lys Cys
            260                 265                 270

Asp Ala Asn Gly Cys Asp Tyr Asn Pro Tyr Arg Met Gly Asn Thr Asp
        275                 280                 285

Phe Tyr Gly Gln Gly Lys Thr Val Asp Thr Ser Lys Lys Phe Thr Val
    290                 295                 300

Val Thr Gln Phe Ala Glu Asn Lys Leu Thr Gln Phe Val Gln Asp
305                 310                 315                 320

Gly Lys Lys Ile Glu Ile Pro Gly Pro Lys Ile Asp Gly Phe Pro Thr
                325                 330                 335

Asp Ser Ala Ile Thr Pro Glu Tyr Cys Thr Ala Glu Phe Asn Val Leu
            340                 345                 350

Gly Asp Arg Asp Arg Phe Ser Glu Val Gly Gly Phe Asp Gln Leu Asn
        355                 360                 365

Asn Ala Leu Asp Val Pro Met Val Leu Val Met Ser Ile Trp Asp Asp
```

```
                370                 375                 380
His Tyr Ala Asn Met Leu Trp Leu Asp Ser Ser Tyr Pro Pro Glu Lys
385                 390                 395                 400

Ala Gly Gln Pro Gly Gly Asp Arg Gly Asp Cys Ala Pro Asp Ser Gly
                405                 410                 415

Val Pro Ser Asp Val Glu Ala Ser Ile Pro Asp Ala Lys Val Val Trp
                420                 425                 430

Ser Asn Ile Arg Phe Gly Pro Ile Gly Ser Thr Val Glu Val
                435                 440                 445

<210> SEQ ID NO 45
<211> LENGTH: 1584
<212> TYPE: DNA
<213> ORGANISM: Exidia glandulosa
<220> FEATURE:
<221> NAME/KEY: CDS
<222> LOCATION: (1)..(1584)

<400> SEQUENCE: 45 atg tac gcc aag ttc gct acc ctc gct gcc ctc gtg gca gct gcc agc    48
Met Tyr Ala Lys Phe Ala Thr Leu Ala Ala Leu Val Ala Ala Ala Ser
1               5                   10                  15 gcc cag cag gca tgc aca ctc acc gcc gag aac cat ccc tcc atg act    96
Ala Gln Gln Ala Cys Thr Leu Thr Ala Glu Asn His Pro Ser Met Thr
                20                  25                  30 tgg tct aag tgt gcc gcc gga ggt agc tgc act tcg gtt tct ggt tca   144
Trp Ser Lys Cys Ala Ala Gly Gly Ser Cys Thr Ser Val Ser Gly Ser
            35                  40                  45 gtc acc atc gat gcc aac tgg cga tgg ctt cac cag ctc aac agc gcc   192
Val Thr Ile Asp Ala Asn Trp Arg Trp Leu His Gln Leu Asn Ser Ala
        50                  55                  60 acc aac tgc tac gac ggc aac aag tgg aac acc acc tac tgc agc aca   240
Thr Asn Cys Tyr Asp Gly Asn Lys Trp Asn Thr Thr Tyr Cys Ser Thr
65                  70                  75                  80 gat gct act tgc gct gct cag tgc tgt gtt gat ggc tca gac tat gct   288
Asp Ala Thr Cys Ala Ala Gln Cys Cys Val Asp Gly Ser Asp Tyr Ala
                85                  90                  95 ggc acc tac ggt gcc acc act agc ggt aac gct ctg aac ctc aag ttc   336
Gly Thr Tyr Gly Ala Thr Thr Ser Gly Asn Ala Leu Asn Leu Lys Phe
                100                 105                 110 gtc acc caa ggg tcc tat tct aag aac atc ggt tcc cgg ttg tac ctc   384
Val Thr Gln Gly Ser Tyr Ser Lys Asn Ile Gly Ser Arg Leu Tyr Leu
            115                 120                 125 atg gag tcg gat acc aag tat cag atg ttt caa ctg ctc ggc cag gag   432
Met Glu Ser Asp Thr Lys Tyr Gln Met Phe Gln Leu Leu Gly Gln Glu
130                 135                 140 ttc act ttc gac gta gat gtc tcc aac ttg ggc tgc ggt ctc aac ggt   480
Phe Thr Phe Asp Val Asp Val Ser Asn Leu Gly Cys Gly Leu Asn Gly
145                 150                 155                 160 gcc ctc tac ttc gtc agc atg gac gct gac ggt ggc acg tcc aag tat   528
Ala Leu Tyr Phe Val Ser Met Asp Ala Asp Gly Gly Thr Ser Lys Tyr
                165                 170                 175 acc ggc aac aag gcc ggc gcc aag tat ggc act ggc tac tgc gac agc   576
Thr Gly Asn Lys Ala Gly Ala Lys Tyr Gly Thr Gly Tyr Cys Asp Ser
                180                 185                 190 cag tgc ccg cgc gac ctg aag ttc atc aat ggt cag gcc aac gtc gag   624
Gln Cys Pro Arg Asp Leu Lys Phe Ile Asn Gly Gln Ala Asn Val Glu
            195                 200                 205 ggc tgg act cct tcc acc aac gat gcc aac gcc ggc att ggc acc cac   672
Gly Trp Thr Pro Ser Thr Asn Asp Ala Asn Ala Gly Ile Gly Thr His
```

-continued

|     | 210 |     |     |     | 215 |     |     |     | 220 |     |     |     |     |     |      |
|---|---|---|---|---|---|---|---|---|---|---|---|---|---|---|---|
| ggc | tcc | tgc | tgt | tcg | gag | atg | gac | atc | tgg | gag | gct | aac | aat | gtt | gcc | 720 |
| Gly | Ser | Cys | Cys | Ser | Glu | Met | Asp | Ile | Trp | Glu | Ala | Asn | Asn | Val | Ala |     |
| 225 |     |     |     |     | 230 |     |     |     |     | 235 |     |     |     |     | 240 |     |

| gct | gcg | tac | acc | ccc | cat | cct | tgc | aca | act | atc | ggc | cag | tcg | atc | tgc | 768 |
|---|---|---|---|---|---|---|---|---|---|---|---|---|---|---|---|---|
| Ala | Ala | Tyr | Thr | Pro | His | Pro | Cys | Thr | Thr | Ile | Gly | Gln | Ser | Ile | Cys |     |
|     |     |     |     |     | 245 |     |     |     |     | 250 |     |     |     |     | 255 |     |

| tcg | ggc | gat | tct | tgc | gga | gga | acc | tac | agc | tct | gac | cgt | tac | gcc | ggt | 816 |
|---|---|---|---|---|---|---|---|---|---|---|---|---|---|---|---|---|
| Ser | Gly | Asp | Ser | Cys | Gly | Gly | Thr | Tyr | Ser | Ser | Asp | Arg | Tyr | Ala | Gly |     |
|     |     |     | 260 |     |     |     |     | 265 |     |     |     |     | 270 |     |     |     |

| gtc | tgc | gat | cca | gac | ggt | tgc | gat | ttc | aac | agc | tac | cgc | atg | ggc | gac | 864 |
|---|---|---|---|---|---|---|---|---|---|---|---|---|---|---|---|---|
| Val | Cys | Asp | Pro | Asp | Gly | Cys | Asp | Phe | Asn | Ser | Tyr | Arg | Met | Gly | Asp |     |
|     |     |     | 275 |     |     |     |     | 280 |     |     |     |     | 285 |     |     |     |

| acg | ggc | ttc | tac | ggc | aag | ggc | ctg | aca | gtc | gac | acg | agc | tcc | aag | ttc | 912 |
|---|---|---|---|---|---|---|---|---|---|---|---|---|---|---|---|---|
| Thr | Gly | Phe | Tyr | Gly | Lys | Gly | Leu | Thr | Val | Asp | Thr | Ser | Ser | Lys | Phe |     |
|     | 290 |     |     |     |     | 295 |     |     |     |     | 300 |     |     |     |     |     |

| acc | gtc | gtc | acc | cag | ttc | ctc | acc | ggc | tcc | gac | ggc | aac | ctt | tcc | gag | 960 |
|---|---|---|---|---|---|---|---|---|---|---|---|---|---|---|---|---|
| Thr | Val | Val | Thr | Gln | Phe | Leu | Thr | Gly | Ser | Asp | Gly | Asn | Leu | Ser | Glu |     |
| 305 |     |     |     |     | 310 |     |     |     |     | 315 |     |     |     |     | 320 |     |

| atc | aag | cgc | ttc | tac | gtc | cag | aac | ggc | aag | gtc | att | ccc | aac | tcg | cag | 1008 |
|---|---|---|---|---|---|---|---|---|---|---|---|---|---|---|---|---|
| Ile | Lys | Arg | Phe | Tyr | Val | Gln | Asn | Gly | Lys | Val | Ile | Pro | Asn | Ser | Gln |     |
|     |     |     |     | 325 |     |     |     |     | 330 |     |     |     |     | 335 |     |     |

| tcc | aag | att | gcc | ggc | gtc | agc | ggc | aac | tcc | atc | acc | acc | gac | ttc | tgc | 1056 |
|---|---|---|---|---|---|---|---|---|---|---|---|---|---|---|---|---|
| Ser | Lys | Ile | Ala | Gly | Val | Ser | Gly | Asn | Ser | Ile | Thr | Thr | Asp | Phe | Cys |     |
|     |     |     | 340 |     |     |     |     | 345 |     |     |     |     | 350 |     |     |     |

| tcc | gcc | cag | aag | acc | gcc | ttc | ggc | gac | acc | aac | gtc | ttc | gcg | caa | aag | 1104 |
|---|---|---|---|---|---|---|---|---|---|---|---|---|---|---|---|---|
| Ser | Ala | Gln | Lys | Thr | Ala | Phe | Gly | Asp | Thr | Asn | Val | Phe | Ala | Gln | Lys |     |
|     |     | 355 |     |     |     |     | 360 |     |     |     |     | 365 |     |     |     |     |

| gga | ggt | ctc | gcc | ggg | atg | ggc | gcc | gcc | ctc | aag | gcc | ggc | atg | gtc | ctc | 1152 |
|---|---|---|---|---|---|---|---|---|---|---|---|---|---|---|---|---|
| Gly | Gly | Leu | Ala | Gly | Met | Gly | Ala | Ala | Leu | Lys | Ala | Gly | Met | Val | Leu |     |
| 370 |     |     |     |     | 375 |     |     |     |     | 380 |     |     |     |     |     |     |

| gtc | atg | tcc | atc | tgg | gac | gac | cac | gca | gtc | aac | atg | ctg | tgg | ctg | gac | 1200 |
|---|---|---|---|---|---|---|---|---|---|---|---|---|---|---|---|---|
| Val | Met | Ser | Ile | Trp | Asp | Asp | His | Ala | Val | Asn | Met | Leu | Trp | Leu | Asp |     |
| 385 |     |     |     |     | 390 |     |     |     |     | 395 |     |     |     |     | 400 |     |

| tcg | acc | tac | ccg | acc | gac | agc | acc | aag | ccc | ggc | gcg | gcc | cgc | ggc | acc | 1248 |
|---|---|---|---|---|---|---|---|---|---|---|---|---|---|---|---|---|
| Ser | Thr | Tyr | Pro | Thr | Asp | Ser | Thr | Lys | Pro | Gly | Ala | Ala | Arg | Gly | Thr |     |
|     |     |     |     | 405 |     |     |     |     | 410 |     |     |     |     | 415 |     |     |

| tgc | ccg | acc | acc | tcc | ggc | gtc | ccc | gcc | gac | gtc | gag | gcc | cag | gtc | ccc | 1296 |
|---|---|---|---|---|---|---|---|---|---|---|---|---|---|---|---|---|
| Cys | Pro | Thr | Thr | Ser | Gly | Val | Pro | Ala | Asp | Val | Glu | Ala | Gln | Val | Pro |     |
|     |     |     | 420 |     |     |     |     | 425 |     |     |     |     | 430 |     |     |     |

| aac | tcg | aac | gtc | atc | tac | tcc | aac | atc | aag | gtc | ggc | ccc | atc | aac | tcg | 1344 |
|---|---|---|---|---|---|---|---|---|---|---|---|---|---|---|---|---|
| Asn | Ser | Asn | Val | Ile | Tyr | Ser | Asn | Ile | Lys | Val | Gly | Pro | Ile | Asn | Ser |     |
|     |     | 435 |     |     |     |     | 440 |     |     |     |     | 445 |     |     |     |     |

| act | ttc | acc | ggc | ggc | act | tcc | ggc | ggc | ggc | ggt | agc | agc | agc | agc | tcc | 1392 |
|---|---|---|---|---|---|---|---|---|---|---|---|---|---|---|---|---|
| Thr | Phe | Thr | Gly | Gly | Thr | Ser | Gly | Gly | Gly | Gly | Ser | Ser | Ser | Ser | Ser |     |
| 450 |     |     |     |     | 455 |     |     |     |     | 460 |     |     |     |     |     |     |

| acc | acc | atc | cga | acc | agc | acc | acc | agc | act | cgc | acc | acc | agc | acc | agc | 1440 |
|---|---|---|---|---|---|---|---|---|---|---|---|---|---|---|---|---|
| Thr | Thr | Ile | Arg | Thr | Ser | Thr | Thr | Ser | Thr | Arg | Thr | Thr | Ser | Thr | Ser |     |
| 465 |     |     |     | 470 |     |     |     |     | 475 |     |     |     |     | 480 |     |     |

| acc | gcg | ccc | ggc | ggc | ggc | tcc | act | ggc | agc | gcc | ggc | gcc | gat | cac | tgg | 1488 |
|---|---|---|---|---|---|---|---|---|---|---|---|---|---|---|---|---|
| Thr | Ala | Pro | Gly | Gly | Gly | Ser | Thr | Gly | Ser | Ala | Gly | Ala | Asp | His | Trp |     |
|     |     |     |     | 485 |     |     |     |     | 490 |     |     |     |     | 495 |     |     |

| gcg | caa | tgc | ggc | ggt | atc | ggc | tgg | act | ggt | ccc | acg | acc | tgc | aag | agc | 1536 |
|---|---|---|---|---|---|---|---|---|---|---|---|---|---|---|---|---|
| Ala | Gln | Cys | Gly | Gly | Ile | Gly | Trp | Thr | Gly | Pro | Thr | Thr | Cys | Lys | Ser |     |
|     |     |     | 500 |     |     |     |     | 505 |     |     |     |     | 510 |     |     |     |

| ccg | tac | acg | tgc | aca | gcc | tcc | aac | ccg | tac | tac | tcg | cag | tgc | ttg | taa | 1584 |
|---|---|---|---|---|---|---|---|---|---|---|---|---|---|---|---|---|
| Pro | Tyr | Thr | Cys | Thr | Ala | Ser | Asn | Pro | Tyr | Tyr | Ser | Gln | Cys | Leu |     |     |
|     |     | 515 |     |     |     |     | 520 |     |     |     |     | 525 |     |     |     |     |

```
<210> SEQ ID NO 46
<211> LENGTH: 527
<212> TYPE: PRT
<213> ORGANISM: Exidia glandulosa

<400> SEQUENCE: 46

Met Tyr Ala Lys Phe Ala Thr Leu Ala Ala Leu Val Ala Ala Ala Ser
1               5                   10                  15

Ala Gln Gln Ala Cys Thr Leu Thr Ala Glu Asn His Pro Ser Met Thr
            20                  25                  30

Trp Ser Lys Cys Ala Ala Gly Gly Ser Cys Thr Ser Val Ser Gly Ser
        35                  40                  45

Val Thr Ile Asp Ala Asn Trp Arg Trp Leu His Gln Leu Asn Ser Ala
    50                  55                  60

Thr Asn Cys Tyr Asp Gly Asn Lys Trp Asn Thr Thr Tyr Cys Ser Thr
65                  70                  75                  80

Asp Ala Thr Cys Ala Ala Gln Cys Cys Val Asp Gly Ser Asp Tyr Ala
                85                  90                  95

Gly Thr Tyr Gly Ala Thr Thr Ser Gly Asn Ala Leu Asn Leu Lys Phe
            100                 105                 110

Val Thr Gln Gly Ser Tyr Ser Lys Asn Ile Gly Ser Arg Leu Tyr Leu
        115                 120                 125

Met Glu Ser Asp Thr Lys Tyr Gln Met Phe Gln Leu Leu Gly Gln Glu
130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Thr Ser Lys Tyr
                165                 170                 175

Thr Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Ala Asn Val Glu
        195                 200                 205

Gly Trp Thr Pro Ser Thr Asn Asp Ala Asn Ala Gly Ile Gly Thr His
    210                 215                 220

Gly Ser Cys Cys Ser Glu Met Asp Ile Trp Glu Ala Asn Asn Val Ala
225                 230                 235                 240

Ala Ala Tyr Thr Pro His Pro Cys Thr Thr Ile Gly Gln Ser Ile Cys
                245                 250                 255

Ser Gly Asp Ser Cys Gly Gly Thr Tyr Ser Ser Asp Arg Tyr Ala Gly
            260                 265                 270

Val Cys Asp Pro Asp Gly Cys Asp Phe Asn Ser Tyr Arg Met Gly Asp
        275                 280                 285

Thr Gly Phe Tyr Gly Lys Gly Leu Thr Val Asp Thr Ser Ser Lys Phe
    290                 295                 300

Thr Val Val Thr Gln Phe Leu Thr Gly Ser Asp Gly Asn Leu Ser Glu
305                 310                 315                 320

Ile Lys Arg Phe Tyr Val Gln Asn Gly Lys Val Ile Pro Asn Ser Gln
                325                 330                 335

Ser Lys Ile Ala Gly Val Ser Gly Asn Ser Ile Thr Thr Asp Phe Cys
            340                 345                 350

Ser Ala Gln Lys Thr Ala Phe Gly Asp Thr Asn Val Phe Ala Gln Lys
        355                 360                 365

Gly Gly Leu Ala Gly Met Gly Ala Ala Leu Lys Ala Gly Met Val Leu
    370                 375                 380
```

```
Val Met Ser Ile Trp Asp Asp His Ala Val Asn Met Leu Trp Leu Asp
385                 390                 395                 400

Ser Thr Tyr Pro Thr Asp Ser Thr Lys Pro Gly Ala Ala Arg Gly Thr
            405                 410                 415

Cys Pro Thr Thr Ser Gly Val Pro Ala Asp Val Glu Ala Gln Val Pro
            420                 425                 430

Asn Ser Asn Val Ile Tyr Ser Asn Ile Lys Val Gly Pro Ile Asn Ser
            435                 440                 445

Thr Phe Thr Gly Gly Thr Ser Gly Gly Gly Ser Ser Ser Ser
    450                 455                 460

Thr Thr Ile Arg Thr Ser Thr Thr Ser Thr Arg Thr Thr Ser Thr Ser
465                 470                 475                 480

Thr Ala Pro Gly Gly Gly Ser Thr Gly Ser Ala Gly Ala Asp His Trp
                485                 490                 495

Ala Gln Cys Gly Gly Ile Gly Trp Thr Gly Pro Thr Thr Cys Lys Ser
                500                 505                 510

Pro Tyr Thr Cys Thr Ala Ser Asn Pro Tyr Tyr Ser Gln Cys Leu
            515                 520                 525

<210> SEQ ID NO 47
<211> LENGTH: 1368
<212> TYPE: DNA
<213> ORGANISM: Exidia glandulosa
<220> FEATURE:
<221> NAME/KEY: CDS
<222> LOCATION: (1)..(1368)

<400> SEQUENCE: 47 atg tac gcc aag ttc gct acc ctc gct gcc ctc gtg gca gct gcc agc      48
Met Tyr Ala Lys Phe Ala Thr Leu Ala Ala Leu Val Ala Ala Ala Ser
1               5                   10                  15 gcc cag cag gca tgc aca ctc acc gcc gag aac cat ccc tcc atg act      96
Ala Gln Gln Ala Cys Thr Leu Thr Ala Glu Asn His Pro Ser Met Thr
                20                  25                  30 tgg tct aag tgt gcc gcc gga ggt agc tgc act tcg gtt tct ggt tca     144
Trp Ser Lys Cys Ala Ala Gly Gly Ser Cys Thr Ser Val Ser Gly Ser
            35                  40                  45 gtc acc atc gat gcc aac tgg cga tgg ctt cac cag ctc aac agc gcc     192
Val Thr Ile Asp Ala Asn Trp Arg Trp Leu His Gln Leu Asn Ser Ala
        50                  55                  60 acc aac tgc tac gac ggc aac aag tgg aac acc acc tac tgc agc aca     240
Thr Asn Cys Tyr Asp Gly Asn Lys Trp Asn Thr Thr Tyr Cys Ser Thr
65                  70                  75                  80 gat gct act tgc gct gct cag tgc tgt gtt gat ggc tca gac tat gct     288
Asp Ala Thr Cys Ala Ala Gln Cys Cys Val Asp Gly Ser Asp Tyr Ala
                85                  90                  95 ggc acc tac ggt gcc acc act agc ggt aac gct ctg aac ctc aag ttc     336
Gly Thr Tyr Gly Ala Thr Thr Ser Gly Asn Ala Leu Asn Leu Lys Phe
                100                 105                 110 gtc acc caa ggg tcc tat tct aag aac atc ggt tcc cgg ttg tac ctc     384
Val Thr Gln Gly Ser Tyr Ser Lys Asn Ile Gly Ser Arg Leu Tyr Leu
            115                 120                 125 atg gag tcg gat acc aag tat cag atg ttt caa ctg ctc ggc cag gag     432
Met Glu Ser Asp Thr Lys Tyr Gln Met Phe Gln Leu Leu Gly Gln Glu
        130                 135                 140 ttc act ttc gac gta gat gtc tcc aac ttg ggc tgc ggt ctc aac ggt     480
Phe Thr Phe Asp Val Asp Val Ser Asn Leu Gly Cys Gly Leu Asn Gly
145                 150                 155                 160 gcc ctc tac ttc gtc agc atg gac gct gac ggt ggc acg tcc aag tat     528
```

```
Ala Leu Tyr Phe Val Ser Met Asp Ala Asp Gly Gly Thr Ser Lys Tyr
                165                 170                 175 acc ggc aac aag gcc ggc gcc aag tat ggc act ggc tac tgc gac agc      576
Thr Gly Asn Lys Ala Gly Ala Lys Tyr Gly Thr Gly Tyr Cys Asp Ser
            180                 185                 190 cag tgc ccg cgc gac ctg aag ttc atc aat ggt cag gcc aac gtc gag      624
Gln Cys Pro Arg Asp Leu Lys Phe Ile Asn Gly Gln Ala Asn Val Glu
        195                 200                 205 ggc tgg act cct tcc acc aac gat gcc aac gcc ggc att ggc acc cac      672
Gly Trp Thr Pro Ser Thr Asn Asp Ala Asn Ala Gly Ile Gly Thr His
    210                 215                 220 ggc tcc tgc tgt tcg gag atg gac atc tgg gag gct aac aat gtt gcc      720
Gly Ser Cys Cys Ser Glu Met Asp Ile Trp Glu Ala Asn Asn Val Ala
225                 230                 235                 240 gct gcg tac acc ccc cat cct tgc aca act atc ggc cag tcg atc tgc      768
Ala Ala Tyr Thr Pro His Pro Cys Thr Thr Ile Gly Gln Ser Ile Cys
                245                 250                 255 tcg ggc gat tct tgc gga gga acc tac agc tct gac cgt tac gcc ggt      816
Ser Gly Asp Ser Cys Gly Gly Thr Tyr Ser Ser Asp Arg Tyr Ala Gly
            260                 265                 270 gtc tgc gat cca gac ggt tgc gat ttc aac agc tac cgc atg ggc gac      864
Val Cys Asp Pro Asp Gly Cys Asp Phe Asn Ser Tyr Arg Met Gly Asp
        275                 280                 285 acg ggc ttc tac ggc aag ggc ctg aca gtc gac acg agc tcc aag ttc      912
Thr Gly Phe Tyr Gly Lys Gly Leu Thr Val Asp Thr Ser Ser Lys Phe
    290                 295                 300 acc gtc gtc acc cag ttc ctc acc ggc tcc gac ggc aac ctt tcc gag      960
Thr Val Val Thr Gln Phe Leu Thr Gly Ser Asp Gly Asn Leu Ser Glu
305                 310                 315                 320 atc aag cgc ttc tac gtc cag aac ggc aag gtc att ccc aac tcg cag     1008
Ile Lys Arg Phe Tyr Val Gln Asn Gly Lys Val Ile Pro Asn Ser Gln
                325                 330                 335 tcc aag att gcc ggc gtc agc ggc aac tcc atc acc acc gac ttc tgc     1056
Ser Lys Ile Ala Gly Val Ser Gly Asn Ser Ile Thr Thr Asp Phe Cys
            340                 345                 350 tcc gcc cag aag acc gcc ttc ggc gac acc aac gtc ttc gcg caa aag     1104
Ser Ala Gln Lys Thr Ala Phe Gly Asp Thr Asn Val Phe Ala Gln Lys
        355                 360                 365 gga ggt ctc gcc ggg atg ggc gcc gcc ctc aag gcc ggc atg gtc ctc     1152
Gly Gly Leu Ala Gly Met Gly Ala Ala Leu Lys Ala Gly Met Val Leu
    370                 375                 380 gtc atg tcc atc tgg gac gat cac tac gcc aac atg ctg tgg ctc gac     1200
Val Met Ser Ile Trp Asp Asp His Tyr Ala Asn Met Leu Trp Leu Asp
385                 390                 395                 400 tcg acc tac ccg act gac gcc tct ccc gat gag ccc ggc aag ggc cgc     1248
Ser Thr Tyr Pro Thr Asp Ala Ser Pro Asp Glu Pro Gly Lys Gly Arg
                405                 410                 415 ggc acc tgc gac acc agc tcg ggt gtt cct gct gac atc gag acc agc     1296
Gly Thr Cys Asp Thr Ser Ser Gly Val Pro Ala Asp Ile Glu Thr Ser
            420                 425                 430 cag gcc agc aac tca gtc atc tac tcg aac atc aag ttc gga ccc atc     1344
Gln Ala Ser Asn Ser Val Ile Tyr Ser Asn Ile Lys Phe Gly Pro Ile
        435                 440                 445 aac tcg acc ttc aag gcg tcc taa                                     1368
Asn Ser Thr Phe Lys Ala Ser
    450                 455

<210> SEQ ID NO 48
<211> LENGTH: 455
<212> TYPE: PRT
```

<213> ORGANISM: Exidia glandulosa

<400> SEQUENCE: 48

```
Met Tyr Ala Lys Phe Ala Thr Leu Ala Ala Leu Val Ala Ala Ser
1               5                   10                  15

Ala Gln Gln Ala Cys Thr Leu Thr Ala Glu Asn His Pro Ser Met Thr
            20                  25                  30

Trp Ser Lys Cys Ala Ala Gly Gly Ser Cys Thr Ser Val Ser Gly Ser
        35                  40                  45

Val Thr Ile Asp Ala Asn Trp Arg Trp Leu His Gln Leu Asn Ser Ala
    50                  55                  60

Thr Asn Cys Tyr Asp Gly Asn Lys Trp Asn Thr Thr Tyr Cys Ser Thr
65                  70                  75                  80

Asp Ala Thr Cys Ala Ala Gln Cys Cys Val Asp Gly Ser Asp Tyr Ala
                85                  90                  95

Gly Thr Tyr Gly Ala Thr Thr Ser Gly Asn Ala Leu Asn Leu Lys Phe
            100                 105                 110

Val Thr Gln Gly Ser Tyr Ser Lys Asn Ile Gly Ser Arg Leu Tyr Leu
        115                 120                 125

Met Glu Ser Asp Thr Lys Tyr Gln Met Phe Gln Leu Leu Gly Gln Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Thr Ser Lys Tyr
                165                 170                 175

Thr Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Ala Asn Val Glu
        195                 200                 205

Gly Trp Thr Pro Ser Thr Asn Asp Ala Asn Ala Gly Ile Gly Thr His
    210                 215                 220

Gly Ser Cys Cys Ser Glu Met Asp Ile Trp Glu Ala Asn Asn Val Ala
225                 230                 235                 240

Ala Ala Tyr Thr Pro His Pro Cys Thr Thr Ile Gly Gln Ser Ile Cys
                245                 250                 255

Ser Gly Asp Ser Cys Gly Gly Thr Tyr Ser Ser Asp Arg Tyr Ala Gly
            260                 265                 270

Val Cys Asp Pro Asp Gly Cys Asp Phe Asn Ser Tyr Arg Met Gly Asp
        275                 280                 285

Thr Gly Phe Tyr Gly Lys Gly Leu Thr Val Asp Thr Ser Ser Lys Phe
    290                 295                 300

Thr Val Val Thr Gln Phe Leu Thr Gly Ser Asp Gly Asn Leu Ser Glu
305                 310                 315                 320

Ile Lys Arg Phe Tyr Val Gln Asn Gly Lys Val Ile Pro Asn Ser Gln
                325                 330                 335

Ser Lys Ile Ala Gly Val Ser Gly Asn Ser Ile Thr Thr Asp Phe Cys
            340                 345                 350

Ser Ala Gln Lys Thr Ala Phe Gly Asp Thr Asn Val Phe Ala Gln Lys
        355                 360                 365

Gly Gly Leu Ala Gly Met Gly Ala Ala Leu Lys Ala Gly Met Val Leu
    370                 375                 380

Val Met Ser Ile Trp Asp Asp His Tyr Ala Asn Met Leu Trp Leu Asp
385                 390                 395                 400
```

```
Ser Thr Tyr Pro Thr Asp Ala Ser Pro Asp Glu Pro Gly Lys Gly Arg
            405                 410                 415

Gly Thr Cys Asp Thr Ser Ser Gly Val Pro Ala Asp Ile Glu Thr Ser
        420                 425                 430

Gln Ala Ser Asn Ser Val Ile Tyr Ser Asn Ile Lys Phe Gly Pro Ile
        435                 440                 445

Asn Ser Thr Phe Lys Ala Ser
    450                 455

<210> SEQ ID NO 49
<211> LENGTH: 1395
<212> TYPE: DNA
<213> ORGANISM: Poitrasia circinans
<220> FEATURE:
<221> NAME/KEY: CDS
<222> LOCATION: (1)..(1395)

<400> SEQUENCE: 49
```

| | | | | | | | | | | | | | | | | |
|---|---|---|---|---|---|---|---|---|---|---|---|---|---|---|---|---|
| atg | cat | cag | act | tcc | gtt | ctt | tct | tcg | ctc | tct | ttg | ctc | ctc | gca | gcc | 48 |
| Met | His | Gln | Thr | Ser | Val | Leu | Ser | Ser | Leu | Ser | Leu | Leu | Ala | Ala | | |
| 1 | | | | 5 | | | | | 10 | | | | | 15 | | |
| tcc | ggt | gcc | cag | cag | gtc | ggc | acc | cag | aat | gct | gag | act | cac | ccg | agt | 96 |
| Ser | Gly | Ala | Gln | Gln | Val | Gly | Thr | Gln | Asn | Ala | Glu | Thr | His | Pro | Ser | |
| | | 20 | | | | | 25 | | | | | 30 | | | | |
| ctg | acc | acc | cag | aag | tgt | acc | acc | gac | ggc | ggc | tgc | acc | gac | cag | tcc | 144 |
| Leu | Thr | Thr | Gln | Lys | Cys | Thr | Thr | Asp | Gly | Gly | Cys | Thr | Asp | Gln | Ser | |
| | | 35 | | | | | 40 | | | | | 45 | | | | |
| act | gcc | atc | gtg | ctt | gac | gcc | aac | tgg | cgc | tgg | ctg | cac | acc | acc | gag | 192 |
| Thr | Ala | Ile | Val | Leu | Asp | Ala | Asn | Trp | Arg | Trp | Leu | His | Thr | Thr | Glu | |
| 50 | | | | | 55 | | | | | 60 | | | | | | |
| ggc | tac | acc | aac | tgc | tac | act | ggc | cag | gaa | tgg | gac | acc | gac | atc | tgc | 240 |
| Gly | Tyr | Thr | Asn | Cys | Tyr | Thr | Gly | Gln | Glu | Trp | Asp | Thr | Asp | Ile | Cys | |
| 65 | | | | 70 | | | | | 75 | | | | | 80 | | |
| tcc | tcc | ccg | gag | gct | tgc | gcc | acc | ggc | tgc | gct | ctt | gac | ggt | gcc | gac | 288 |
| Ser | Ser | Pro | Glu | Ala | Cys | Ala | Thr | Gly | Cys | Ala | Leu | Asp | Gly | Ala | Asp | |
| | | | | 85 | | | | | 90 | | | | | 95 | | |
| tac | gag | ggc | act | tac | ggc | att | acg | act | gac | ggc | aac | gct | ctt | tcc | atg | 336 |
| Tyr | Glu | Gly | Thr | Tyr | Gly | Ile | Thr | Thr | Asp | Gly | Asn | Ala | Leu | Ser | Met | |
| | | | 100 | | | | | 105 | | | | | 110 | | | |
| aag | ttt | gtc | acc | cag | ggc | tcg | cag | aag | aac | gtc | ggc | ggt | cgt | gtt | tac | 384 |
| Lys | Phe | Val | Thr | Gln | Gly | Ser | Gln | Lys | Asn | Val | Gly | Gly | Arg | Val | Tyr | |
| | | | 115 | | | | | 120 | | | | | 125 | | | |
| ctg | ctt | gct | ccc | gac | tcc | gaa | gat | gcg | tac | gag | ctc | ttc | aag | ttg | aag | 432 |
| Leu | Leu | Ala | Pro | Asp | Ser | Glu | Asp | Ala | Tyr | Glu | Leu | Phe | Lys | Leu | Lys | |
| | 130 | | | | | 135 | | | | | 140 | | | | | |
| aac | cag | gag | ttc | act | ttc | gac | gtt | gac | gtc | tcc | gac | ctc | ccc | tgc | ggc | 480 |
| Asn | Gln | Glu | Phe | Thr | Phe | Asp | Val | Asp | Val | Ser | Asp | Leu | Pro | Cys | Gly | |
| 145 | | | | | 150 | | | | | 155 | | | | | 160 | |
| ctg | aac | ggc | gcc | ctg | tac | ttc | tcc | gag | atg | gat | gaa | gat | ggt | ggc | atg | 528 |
| Leu | Asn | Gly | Ala | Leu | Tyr | Phe | Ser | Glu | Met | Asp | Glu | Asp | Gly | Gly | Met | |
| | | | | 165 | | | | | 170 | | | | | 175 | | |
| tcc | aag | tac | gag | aac | aac | aag | gcc | ggc | gcc | aag | tac | ggc | act | ggc | tac | 576 |
| Ser | Lys | Tyr | Glu | Asn | Asn | Lys | Ala | Gly | Ala | Lys | Tyr | Gly | Thr | Gly | Tyr | |
| | | | 180 | | | | | 185 | | | | | 190 | | | |
| tgc | gac | acg | cag | tgc | ccc | cac | gac | gtc | aag | ttc | atc | aac | ggc | gag | gcc | 624 |
| Cys | Asp | Thr | Gln | Cys | Pro | His | Asp | Val | Lys | Phe | Ile | Asn | Gly | Glu | Ala | |
| | | | 195 | | | | | 200 | | | | | 205 | | | |
| aac | att | ctc | aac | tgg | acc | aag | tcc | gag | acc | gac | gtc | aac | gcc | ggc | act | 672 |
| Asn | Ile | Leu | Asn | Trp | Thr | Lys | Ser | Glu | Thr | Asp | Val | Asn | Ala | Gly | Thr | |
| | 210 | | | | | 215 | | | | | 220 | | | | | |

| | | |
|---|---|---|
| ggc caa tac ggc tcc tgc tgc aac gag atg gat atc tgg gag gcc aac<br>Gly Gln Tyr Gly Ser Cys Cys Asn Glu Met Asp Ile Trp Glu Ala Asn<br>225                          230                      235                      240 | | 720 |
| tcg cag gcc acc gcc gtc act ccc cac gtc tgc aac gcc gat gtc atc<br>Ser Gln Ala Thr Ala Val Thr Pro His Val Cys Asn Ala Asp Val Ile<br>                        245                      250                      255 | | 768 |
| ggc cag gtc cgt tgc aac ggc acc gac tgc ggt gac ggc gac aac cgc<br>Gly Gln Val Arg Cys Asn Gly Thr Asp Cys Gly Asp Gly Asp Asn Arg<br>        260                      265                      270 | | 816 |
| tac ggc ggc gtc tgc gac aag gat ggc tgc gac tac aac ccc tac cgc<br>Tyr Gly Gly Val Cys Asp Lys Asp Gly Cys Asp Tyr Asn Pro Tyr Arg<br>            275                      280                      285 | | 864 |
| atg ggc aac gag tcg ttc tac ggc tcc aac ggc agc acc atc gac acc<br>Met Gly Asn Glu Ser Phe Tyr Gly Ser Asn Gly Ser Thr Ile Asp Thr<br>        290                      295                      300 | | 912 |
| act gcc aag ttc acc gtc att acg cag ttc atc acc tcg gac aac act<br>Thr Ala Lys Phe Thr Val Ile Thr Gln Phe Ile Thr Ser Asp Asn Thr<br>305                          310                      315                      320 | | 960 |
| tcg act ggc gac ctc gtt gag atc cgc cgc aag tac gtc cag gac ggc<br>Ser Thr Gly Asp Leu Val Glu Ile Arg Arg Lys Tyr Val Gln Asp Gly<br>                        325                      330                      335 | | 1008 |
| acc gtc atc gag aac tcg ttc gcc gac tac gac acc ctg gcc acg ttc<br>Thr Val Ile Glu Asn Ser Phe Ala Asp Tyr Asp Thr Leu Ala Thr Phe<br>                340                      345                      350 | | 1056 |
| aac tcc atc tcg gac gac ttc tgc gac gcc cag aag acg ctc ttc ggc<br>Asn Ser Ile Ser Asp Asp Phe Cys Asp Ala Gln Lys Thr Leu Phe Gly<br>                        355                      360                      365 | | 1104 |
| gac gag aac gac ttc aag acc aag ggc ggc att gcc cgc atg ggc gag<br>Asp Glu Asn Asp Phe Lys Thr Lys Gly Gly Ile Ala Arg Met Gly Glu<br>        370                      375                      380 | | 1152 |
| tcc ttc gag cgc ggc atg gtc ctc gtc atg agc atc tgg gat gac cac<br>Ser Phe Glu Arg Gly Met Val Leu Val Met Ser Ile Trp Asp Asp His<br>385                          390                      395                      400 | | 1200 |
| gcg gcc aac gcc ctc tgg ctc gac tcg acc tac ccc gtc gac ggc gac<br>Ala Ala Asn Ala Leu Trp Leu Asp Ser Thr Tyr Pro Val Asp Gly Asp<br>                        405                      410                      415 | | 1248 |
| gcg acc aag cct ggc atc aag cgc ggc cct tgc ggc acc gac act ggt<br>Ala Thr Lys Pro Gly Ile Lys Arg Gly Pro Cys Gly Thr Asp Thr Gly<br>                420                      425                      430 | | 1296 |
| gtt ccc gcc gac gtc gag tcg gag tcg ccc gat tcg acc gtc atc tac<br>Val Pro Ala Asp Val Glu Ser Glu Ser Pro Asp Ser Thr Val Ile Tyr<br>                        435                      440                      445 | | 1344 |
| tcc aac att cgc tac gga gac att ggc tcc acc ttc aac gcc acc gct<br>Ser Asn Ile Arg Tyr Gly Asp Ile Gly Ser Thr Phe Asn Ala Thr Ala<br>        450                      455                      460 | | 1392 |
| tag | | 1395 |

```
<210> SEQ ID NO 50
<211> LENGTH: 464
<212> TYPE: PRT
<213> ORGANISM: Poitrasia circinans

<400> SEQUENCE: 50

Met His Gln Thr Ser Val Leu Ser Ser Leu Ser Leu Leu Ala Ala
1               5                   10                  15

Ser Gly Ala Gln Gln Val Gly Thr Gln Asn Ala Glu Thr His Pro Ser
            20                  25                  30

Leu Thr Thr Gln Lys Cys Thr Asp Gly Gly Cys Thr Asp Gln Ser
        35                  40                  45
```

```
Thr Ala Ile Val Leu Asp Ala Asn Trp Arg Trp Leu His Thr Thr Glu
 50                  55                  60

Gly Tyr Thr Asn Cys Tyr Thr Gly Gln Glu Trp Asp Thr Asp Ile Cys
 65                  70                  75                  80

Ser Ser Pro Glu Ala Cys Ala Thr Gly Cys Ala Leu Asp Gly Ala Asp
                 85                  90                  95

Tyr Glu Gly Thr Tyr Gly Ile Thr Thr Asp Gly Asn Ala Leu Ser Met
                100                 105                 110

Lys Phe Val Thr Gln Gly Ser Gln Lys Asn Val Gly Arg Val Tyr
                115                 120                 125

Leu Leu Ala Pro Asp Ser Glu Asp Ala Tyr Glu Leu Phe Lys Leu Lys
130                 135                 140

Asn Gln Glu Phe Thr Phe Asp Val Asp Val Ser Asp Leu Pro Cys Gly
145                 150                 155                 160

Leu Asn Gly Ala Leu Tyr Phe Ser Glu Met Asp Glu Asp Gly Gly Met
                165                 170                 175

Ser Lys Tyr Glu Asn Asn Lys Ala Gly Ala Lys Tyr Gly Thr Gly Tyr
                180                 185                 190

Cys Asp Thr Gln Cys Pro His Asp Val Lys Phe Ile Asn Gly Glu Ala
                195                 200                 205

Asn Ile Leu Asn Trp Thr Lys Ser Glu Thr Asp Val Asn Ala Gly Thr
                210                 215                 220

Gly Gln Tyr Gly Ser Cys Cys Asn Glu Met Asp Ile Trp Glu Ala Asn
225                 230                 235                 240

Ser Gln Ala Thr Ala Val Thr Pro His Val Cys Asn Ala Asp Val Ile
                245                 250                 255

Gly Gln Val Arg Cys Asn Gly Thr Asp Cys Gly Asp Gly Asp Asn Arg
                260                 265                 270

Tyr Gly Gly Val Cys Asp Lys Asp Gly Cys Asp Tyr Asn Pro Tyr Arg
                275                 280                 285

Met Gly Asn Glu Ser Phe Tyr Gly Ser Asn Gly Ser Thr Ile Asp Thr
                290                 295                 300

Thr Ala Lys Phe Thr Val Ile Thr Gln Phe Ile Thr Ser Asp Asn Thr
305                 310                 315                 320

Ser Thr Gly Asp Leu Val Glu Ile Arg Arg Lys Tyr Val Gln Asp Gly
                325                 330                 335

Thr Val Ile Glu Asn Ser Phe Ala Asp Tyr Asp Thr Leu Ala Thr Phe
                340                 345                 350

Asn Ser Ile Ser Asp Asp Phe Cys Asp Ala Gln Lys Thr Leu Phe Gly
                355                 360                 365

Asp Glu Asn Asp Phe Lys Thr Lys Gly Gly Ile Ala Arg Met Gly Glu
                370                 375                 380

Ser Phe Glu Arg Gly Met Val Leu Val Met Ser Ile Trp Asp Asp His
385                 390                 395                 400

Ala Ala Asn Ala Leu Trp Leu Asp Ser Thr Tyr Pro Val Asp Gly Asp
                405                 410                 415

Ala Thr Lys Pro Gly Ile Lys Arg Gly Pro Cys Gly Thr Asp Thr Gly
                420                 425                 430

Val Pro Ala Asp Val Glu Ser Glu Ser Pro Asp Ser Thr Val Ile Tyr
                435                 440                 445

Ser Asn Ile Arg Tyr Gly Asp Ile Gly Ser Thr Phe Asn Ala Thr Ala
450                 455                 460
```

```
<210> SEQ ID NO 51
<211> LENGTH: 1383
<212> TYPE: DNA
<213> ORGANISM: Coprinus cinereus
<220> FEATURE:
<221> NAME/KEY: CDS
<222> LOCATION: (1)..(1383)

<400> SEQUENCE: 51
```

| | | | | | | | | | | | | | | | | |
|---|---|---|---|---|---|---|---|---|---|---|---|---|---|---|---|---|
| atg | ttc | aag | aaa | gtc | gcc | ctc | acc | gct | ctc | tgc | ttc | ctc | gcc | gtc | gca | 48 |
| Met | Phe | Lys | Lys | Val | Ala | Leu | Thr | Ala | Leu | Cys | Phe | Leu | Ala | Val | Ala | |
| 1 | | | | 5 | | | | | 10 | | | | | 15 | | |
| cag | gcc | caa | cag | gtc | ggt | cgc | gaa | gtc | gct | gaa | aac | cac | ccc | cgt | ctc | 96 |
| Gln | Ala | Gln | Gln | Val | Gly | Arg | Glu | Val | Ala | Glu | Asn | His | Pro | Arg | Leu | |
| | | | 20 | | | | | 25 | | | | | 30 | | | |
| ccg | tgg | cag | cgt | tgc | act | cgc | aac | ggc | gga | tgc | cag | act | gtc | tcc | aac | 144 |
| Pro | Trp | Gln | Arg | Cys | Thr | Arg | Asn | Gly | Gly | Cys | Gln | Thr | Val | Ser | Asn | |
| | | | | 35 | | | | | 40 | | | | | 45 | | |
| ggt | cag | gtc | gtc | ctc | gac | gcc | aac | tgg | cga | tgg | ctc | cac | gtc | acc | gac | 192 |
| Gly | Gln | Val | Val | Leu | Asp | Ala | Asn | Trp | Arg | Trp | Leu | His | Val | Thr | Asp | |
| | | 50 | | | | | 55 | | | | | 60 | | | | |
| ggc | tac | acc | aac | tgc | tac | acc | ggt | aac | tcc | tgg | aac | agc | acc | gtc | tgc | 240 |
| Gly | Tyr | Thr | Asn | Cys | Tyr | Thr | Gly | Asn | Ser | Trp | Asn | Ser | Thr | Val | Cys | |
| 65 | | | | | 70 | | | | | 75 | | | | | 80 | |
| tcc | gac | ccc | acc | acc | tgc | gct | cag | cga | tgc | gct | ctc | gag | ggt | gcc | aac | 288 |
| Ser | Asp | Pro | Thr | Thr | Cys | Ala | Gln | Arg | Cys | Ala | Leu | Glu | Gly | Ala | Asn | |
| | | | | 85 | | | | | 90 | | | | | 95 | | |
| tac | cag | caa | acc | tac | ggt | atc | acc | acc | aac | gga | gac | gcc | ctc | acc | atc | 336 |
| Tyr | Gln | Gln | Thr | Tyr | Gly | Ile | Thr | Thr | Asn | Gly | Asp | Ala | Leu | Thr | Ile | |
| | | | 100 | | | | | 105 | | | | | 110 | | | |
| aag | ttc | ctc | acc | cga | tcc | caa | caa | acc | aac | gtc | ggt | gct | cgt | gtc | tac | 384 |
| Lys | Phe | Leu | Thr | Arg | Ser | Gln | Gln | Thr | Asn | Val | Gly | Ala | Arg | Val | Tyr | |
| | | | | 115 | | | | | 120 | | | | | 125 | | |
| ctc | atg | gag | aac | gag | aac | cga | tac | cag | atg | ttc | aac | ctc | ctc | aac | aag | 432 |
| Leu | Met | Glu | Asn | Glu | Asn | Arg | Tyr | Gln | Met | Phe | Asn | Leu | Leu | Asn | Lys | |
| | 130 | | | | | 135 | | | | | 140 | | | | | |
| gag | ttc | acc | ttc | gac | gtt | gac | gtc | tcc | aag | gtt | cct | tgc | ggt | atc | aac | 480 |
| Glu | Phe | Thr | Phe | Asp | Val | Asp | Val | Ser | Lys | Val | Pro | Cys | Gly | Ile | Asn | |
| 145 | | | | | 150 | | | | | 155 | | | | | 160 | |
| ggt | gcc | ctc | tac | ttc | atc | cag | atg | gac | gcc | gat | ggt | ggt | atg | agc | aag | 528 |
| Gly | Ala | Leu | Tyr | Phe | Ile | Gln | Met | Asp | Ala | Asp | Gly | Gly | Met | Ser | Lys | |
| | | | | 165 | | | | | 170 | | | | | 175 | | |
| caa | ccc | aac | aac | agg | gct | ggt | gct | aag | tac | ggt | acc | ggc | tac | tgc | gac | 576 |
| Gln | Pro | Asn | Asn | Arg | Ala | Gly | Ala | Lys | Tyr | Gly | Thr | Gly | Tyr | Cys | Asp | |
| | | | 180 | | | | | 185 | | | | | 190 | | | |
| tct | cag | tgc | ccc | cgt | gac | atc | aag | ttc | att | gac | ggc | gtg | gcc | aac | agc | 624 |
| Ser | Gln | Cys | Pro | Arg | Asp | Ile | Lys | Phe | Ile | Asp | Gly | Val | Ala | Asn | Ser | |
| | | 195 | | | | | 200 | | | | | 205 | | | | |
| gcc | gac | tgg | act | cca | tcc | gag | acc | gat | ccc | aat | gcc | gga | agg | ggt | cgc | 672 |
| Ala | Asp | Trp | Thr | Pro | Ser | Glu | Thr | Asp | Pro | Asn | Ala | Gly | Arg | Gly | Arg | |
| | 210 | | | | | 215 | | | | | 220 | | | | | |
| tac | ggc | att | tgc | tgc | gcc | gag | atg | gat | atc | tgg | gag | gcc | aac | tcc | atc | 720 |
| Tyr | Gly | Ile | Cys | Cys | Ala | Glu | Met | Asp | Ile | Trp | Glu | Ala | Asn | Ser | Ile | |
| 225 | | | | | 230 | | | | | 235 | | | | | 240 | |
| tcc | aat | gcc | tac | acc | ccc | cac | cct | tgc | cga | acc | cag | aac | gat | ggt | ggc | 768 |
| Ser | Asn | Ala | Tyr | Thr | Pro | His | Pro | Cys | Arg | Thr | Gln | Asn | Asp | Gly | Gly | |
| | | | | 245 | | | | | 250 | | | | | 255 | | |
| tac | cag | cgc | tgc | gag | ggc | cgc | gac | tgc | aac | cag | cct | cgc | tat | gag | ggt | 816 |
| Tyr | Gln | Arg | Cys | Glu | Gly | Arg | Asp | Cys | Asn | Gln | Pro | Arg | Tyr | Glu | Gly | |
| | | | 260 | | | | | 265 | | | | | 270 | | | |
| ctt | tgc | gat | cct | gat | ggc | tgt | gac | tac | aac | ccc | ttc | cgc | atg | ggt | aac | 864 |

-continued

```
Leu Cys Asp Pro Asp Gly Cys Asp Tyr Asn Pro Phe Arg Met Gly Asn
        275                 280                 285 aag gac ttc tac gga ccc gga aag acc gtc gac acc aac agg aag atg    912
Lys Asp Phe Tyr Gly Pro Gly Lys Thr Val Asp Thr Asn Arg Lys Met
290                 295                 300 acc gtc gtc acc caa ttc atc acc cac gac aac acc gac act ggc acc    960
Thr Val Val Thr Gln Phe Ile Thr His Asp Asn Thr Asp Thr Gly Thr
305                 310                 315                 320 ctc gtt gac atc cgc cgc ctc tac gtt caa gac ggc cgt gtc att gcc   1008
Leu Val Asp Ile Arg Arg Leu Tyr Val Gln Asp Gly Arg Val Ile Ala
            325                 330                 335 aac cct ccc acc aac ttc ccc ggt ctc atg ccc gcc cac gac tcc atc   1056
Asn Pro Pro Thr Asn Phe Pro Gly Leu Met Pro Ala His Asp Ser Ile
            340                 345                 350 acc gag cag ttc tgc act gac cag aag aac ctc ttc ggc gac tac agc   1104
Thr Glu Gln Phe Cys Thr Asp Gln Lys Asn Leu Phe Gly Asp Tyr Ser
                355                 360                 365 agc ttc gct cgt gac ggt ggt ctc gct cac atg ggt cgc tcc ctc gcc   1152
Ser Phe Ala Arg Asp Gly Gly Leu Ala His Met Gly Arg Ser Leu Ala
370                 375                 380 aag ggt cac gtc ctc gct ctc tcc atc tgg aac gac cac ggt gcc cac   1200
Lys Gly His Val Leu Ala Leu Ser Ile Trp Asn Asp His Gly Ala His
385                 390                 395                 400 atg ttg tgg ctc gac tcc aac tac ccc acc gac gct gac ccc aac aag   1248
Met Leu Trp Leu Asp Ser Asn Tyr Pro Thr Asp Ala Asp Pro Asn Lys
                405                 410                 415 ccc ggt att gct cgt ggt acc tgc ccg acc act ggt ggc acc ccc cgt   1296
Pro Gly Ile Ala Arg Gly Thr Cys Pro Thr Thr Gly Gly Thr Pro Arg
            420                 425                 430 gaa acc gaa caa aac cac cct gat gcc cag gtc atc ttc tcc aac att   1344
Glu Thr Glu Gln Asn His Pro Asp Ala Gln Val Ile Phe Ser Asn Ile
            435                 440                 445 aaa ttc ggt gac atc ggc tcg act ttc tct ggt tac taa                1383
Lys Phe Gly Asp Ile Gly Ser Thr Phe Ser Gly Tyr
450                 455                 460
```

<210> SEQ ID NO 52
<211> LENGTH: 460
<212> TYPE: PRT
<213> ORGANISM: Coprinus cinereus

<400> SEQUENCE: 52

```
Met Phe Lys Lys Val Ala Leu Thr Ala Leu Cys Phe Leu Ala Val Ala
1               5                   10                  15

Gln Ala Gln Gln Val Gly Arg Glu Val Ala Glu Asn His Pro Arg Leu
            20                  25                  30

Pro Trp Gln Arg Cys Thr Arg Asn Gly Gly Cys Gln Thr Val Ser Asn
        35                  40                  45

Gly Gln Val Val Leu Asp Ala Asn Trp Arg Trp Leu His Val Thr Asp
    50                  55                  60

Gly Tyr Thr Asn Cys Tyr Thr Gly Asn Ser Trp Asn Ser Thr Val Cys
65                  70                  75                  80

Ser Asp Pro Thr Thr Cys Ala Gln Arg Cys Ala Leu Glu Gly Ala Asn
                85                  90                  95

Tyr Gln Gln Thr Tyr Gly Ile Thr Thr Asn Gly Asp Ala Leu Thr Ile
            100                 105                 110

Lys Phe Leu Thr Arg Ser Gln Gln Thr Asn Val Gly Ala Arg Val Tyr
        115                 120                 125
```

```
Leu Met Glu Asn Glu Asn Arg Tyr Gln Met Phe Asn Leu Leu Asn Lys
    130                 135                 140

Glu Phe Thr Phe Asp Val Asp Val Ser Lys Val Pro Cys Gly Ile Asn
145                 150                 155                 160

Gly Ala Leu Tyr Phe Ile Gln Met Asp Ala Asp Gly Gly Met Ser Lys
                165                 170                 175

Gln Pro Asn Asn Arg Ala Gly Ala Lys Tyr Gly Thr Gly Tyr Cys Asp
                180                 185                 190

Ser Gln Cys Pro Arg Asp Ile Lys Phe Ile Asp Gly Val Ala Asn Ser
            195                 200                 205

Ala Asp Trp Thr Pro Ser Glu Thr Asp Pro Asn Ala Gly Arg Gly Arg
    210                 215                 220

Tyr Gly Ile Cys Cys Ala Glu Met Asp Ile Trp Glu Ala Asn Ser Ile
225                 230                 235                 240

Ser Asn Ala Tyr Thr Pro His Pro Cys Arg Thr Gln Asn Asp Gly Gly
                245                 250                 255

Tyr Gln Arg Cys Glu Gly Arg Asp Cys Asn Gln Pro Tyr Glu Gly
                260                 265                 270

Leu Cys Asp Pro Asp Gly Cys Asp Tyr Asn Pro Phe Arg Met Gly Asn
    275                 280                 285

Lys Asp Phe Tyr Gly Pro Gly Lys Thr Val Asp Thr Asn Arg Lys Met
    290                 295                 300

Thr Val Val Thr Gln Phe Ile Thr His Asp Asn Thr Asp Thr Gly Thr
305                 310                 315                 320

Leu Val Asp Ile Arg Arg Leu Tyr Val Gln Asp Gly Arg Val Ile Ala
                325                 330                 335

Asn Pro Pro Thr Asn Phe Pro Gly Leu Met Pro Ala His Asp Ser Ile
                340                 345                 350

Thr Glu Gln Phe Cys Thr Asp Gln Lys Asn Leu Phe Gly Asp Tyr Ser
            355                 360                 365

Ser Phe Ala Arg Asp Gly Gly Leu Ala His Met Gly Arg Ser Leu Ala
    370                 375                 380

Lys Gly His Val Leu Ala Leu Ser Ile Trp Asn Asp His Gly Ala His
385                 390                 395                 400

Met Leu Trp Leu Asp Ser Asn Tyr Pro Thr Asp Ala Asp Pro Asn Lys
                405                 410                 415

Pro Gly Ile Ala Arg Gly Thr Cys Pro Thr Thr Gly Gly Thr Pro Arg
                420                 425                 430

Glu Thr Glu Gln Asn His Pro Asp Ala Gln Val Ile Phe Ser Asn Ile
            435                 440                 445

Lys Phe Gly Asp Ile Gly Ser Thr Phe Ser Gly Tyr
    450                 455                 460

<210> SEQ ID NO 53
<211> LENGTH: 1353
<212> TYPE: DNA
<213> ORGANISM: Acremonium sp.
<220> FEATURE:
<221> NAME/KEY: CDS
<222> LOCATION: (1)..(1353)

<400> SEQUENCE: 53 atg atg aag cag tat ctt cag tac ctg gcg gcg gct ctg ccc cta atg      48
Met Met Lys Gln Tyr Leu Gln Tyr Leu Ala Ala Ala Leu Pro Leu Met
1               5                   10                  15 ggc ctt gcc gcg ggc cag caa gcc ggc cgg gag acg ccc gaa aac cac      96
```

```
                Gly Leu Ala Ala Gly Gln Gln Ala Gly Arg Glu Thr Pro Glu Asn His
                         20                  25                  30 ccc cgg ctc acc tgg aag aag tgc tcg ggc cag ggg tcc tgc cag acc           144
Pro Arg Leu Thr Trp Lys Lys Cys Ser Gly Gln Gly Ser Cys Gln Thr
         35                  40                  45 gtc aac ggc gag gtc gtc att gat gcc aac tgg cgc tgg ctc cac gac           192
Val Asn Gly Glu Val Val Ile Asp Ala Asn Trp Arg Trp Leu His Asp
 50                  55                  60 tcc aac atg cag aac tgc tac gac ggc aac cag tgg acc agc gcg tgc           240
Ser Asn Met Gln Asn Cys Tyr Asp Gly Asn Gln Trp Thr Ser Ala Cys
 65                  70                  75                  80 agc tcg gcc acc gac tgc gcc tcc aag tgc tac atc gag ggt gcc gac           288
Ser Ser Ala Thr Asp Cys Ala Ser Lys Cys Tyr Ile Glu Gly Ala Asp
                 85                  90                  95 tac ggc agg acc tac ggc gct tcg acg agc ggc gac tcc ctc acg ctc           336
Tyr Gly Arg Thr Tyr Gly Ala Ser Thr Ser Gly Asp Ser Leu Thr Leu
            100                 105                 110 aag ttt gtc act cag cac gag tac ggt acc aac atc ggc tcg cgc ttc           384
Lys Phe Val Thr Gln His Glu Tyr Gly Thr Asn Ile Gly Ser Arg Phe
                115                 120                 125 tac ctg atg agc agc ccg acc cgg tac cag atg ttc acc ctc atg aac           432
Tyr Leu Met Ser Ser Pro Thr Arg Tyr Gln Met Phe Thr Leu Met Asn
130                 135                 140 aac gaa ttt gct ttc gat gtc gac ctc tcg acc gtc gag tgc ggc atc           480
Asn Glu Phe Ala Phe Asp Val Asp Leu Ser Thr Val Glu Cys Gly Ile
145                 150                 155                 160 aac agc gcc ctg tac ttc gtc gcc atg gag gag gac ggc ggc atg gcc           528
Asn Ser Ala Leu Tyr Phe Val Ala Met Glu Glu Asp Gly Gly Met Ala
                165                 170                 175 agc tac ccc acc aac aag gcc gga gcc aag tac ggc acg ggt tac tgc           576
Ser Tyr Pro Thr Asn Lys Ala Gly Ala Lys Tyr Gly Thr Gly Tyr Cys
                180                 185                 190 gac gcc caa tgc gcc cgt gat ctc aag ttc gtc ggc ggc aag gcc aac           624
Asp Ala Gln Cys Ala Arg Asp Leu Lys Phe Val Gly Gly Lys Ala Asn
            195                 200                 205 att gag ggc tgg agg ccg tcc acc aac gac gcg aac gcc ggc gtc ggc           672
Ile Glu Gly Trp Arg Pro Ser Thr Asn Asp Ala Asn Ala Gly Val Gly
210                 215                 220 ccg atg ggc ggc tgc tgc gcg gaa atc gat gtt tgg gag tcc aac gcc           720
Pro Met Gly Gly Cys Cys Ala Glu Ile Asp Val Trp Glu Ser Asn Ala
225                 230                 235                 240 cac gct ttt gcc ttc acg ccg cac gcg tgc gag aac aac aac tac cac           768
His Ala Phe Ala Phe Thr Pro His Ala Cys Glu Asn Asn Asn Tyr His
                245                 250                 255 atc tgc gag acc tcc aac tgc ggc ggt acc tac tcc gac gac cgc ttc           816
Ile Cys Glu Thr Ser Asn Cys Gly Gly Thr Tyr Ser Asp Asp Arg Phe
            260                 265                 270 gcc ggc ctc tgc gac gcc aac ggc tgc gac tac aac ccg tac cgc atg           864
Ala Gly Leu Cys Asp Ala Asn Gly Cys Asp Tyr Asn Pro Tyr Arg Met
            275                 280                 285 ggc aac ccc gac ttc tac ggc aag ggc aag act ctt gac acc tcg cgg           912
Gly Asn Pro Asp Phe Tyr Gly Lys Gly Lys Thr Leu Asp Thr Ser Arg
            290                 295                 300 aag ttc acc gtc gtc acc cgc ttc cag gag aac gac ctc tcg cag tac           960
Lys Phe Thr Val Val Thr Arg Phe Gln Glu Asn Asp Leu Ser Gln Tyr
305                 310                 315                 320 ttc atc cag gac ggc cgc aag atc gag atc ccg ccc ccg acc tgg gac          1008
Phe Ile Gln Asp Gly Arg Lys Ile Glu Ile Pro Pro Pro Thr Trp Asp
                325                 330                 335
```

```
ggc ctc ccg aag agc agc cac atc acg ccc gag ctg tgc gcg acc cag    1056
Gly Leu Pro Lys Ser Ser His Ile Thr Pro Glu Leu Cys Ala Thr Gln
            340                 345                 350 ttc gac gtc ttc gac gac cgc aac cgc ttc gag gag gtc ggc ggc ttc    1104
Phe Asp Val Phe Asp Asp Arg Asn Arg Phe Glu Glu Val Gly Gly Phe
        355                 360                 365 ccc gcc ctc aac gcc gct ctc cgc atc ccc atg gtc ctt gtc atg tcc    1152
Pro Ala Leu Asn Ala Ala Leu Arg Ile Pro Met Val Leu Val Met Ser
370                 375                 380 atc tgg gac gac cac tac gcc aac atg ctc tgg ctc gac tcc gtc tac    1200
Ile Trp Asp Asp His Tyr Ala Asn Met Leu Trp Leu Asp Ser Val Tyr
385                 390                 395                 400 ccg ccc gag aag gag ggc acc ccc ggc gcc gag cgt ggc cct tgc ccc    1248
Pro Pro Glu Lys Glu Gly Thr Pro Gly Ala Glu Arg Gly Pro Cys Pro
                405                 410                 415 cag acc tct ggt gtc ccc gcc gaa gtc gag gcc cag tac ccc aac gcc    1296
Gln Thr Ser Gly Val Pro Ala Glu Val Glu Ala Gln Tyr Pro Asn Ala
            420                 425                 430 aag gtc gtc tgg tcc aac atc cgc ttc ggc ccc atc ggc tcg acc tac    1344
Lys Val Val Trp Ser Asn Ile Arg Phe Gly Pro Ile Gly Ser Thr Tyr
        435                 440                 445 aac atg taa                                                         1353
Asn Met
    450

<210> SEQ ID NO 54
<211> LENGTH: 450
<212> TYPE: PRT
<213> ORGANISM: Acremonium sp.

<400> SEQUENCE: 54

Met Met Lys Gln Tyr Leu Gln Tyr Leu Ala Ala Ala Leu Pro Leu Met
1               5                   10                  15

Gly Leu Ala Ala Gly Gln Gln Ala Gly Arg Glu Thr Pro Glu Asn His
            20                  25                  30

Pro Arg Leu Thr Trp Lys Lys Cys Ser Gly Gln Gly Ser Cys Gln Thr
        35                  40                  45

Val Asn Gly Glu Val Val Ile Asp Ala Asn Trp Arg Trp Leu His Asp
    50                  55                  60

Ser Asn Met Gln Asn Cys Tyr Asp Gly Asn Gln Trp Thr Ser Ala Cys
65                  70                  75                  80

Ser Ser Ala Thr Asp Cys Ala Ser Lys Cys Tyr Ile Glu Gly Ala Asp
                85                  90                  95

Tyr Gly Arg Thr Tyr Gly Ala Ser Thr Ser Gly Asp Ser Leu Thr Leu
            100                 105                 110

Lys Phe Val Thr Gln His Glu Tyr Gly Thr Asn Ile Gly Ser Arg Phe
        115                 120                 125

Tyr Leu Met Ser Ser Pro Thr Arg Tyr Gln Met Phe Thr Leu Met Asn
    130                 135                 140

Asn Glu Phe Ala Phe Asp Val Asp Leu Ser Thr Val Glu Cys Gly Ile
145                 150                 155                 160

Asn Ser Ala Leu Tyr Phe Val Ala Met Glu Glu Asp Gly Gly Met Ala
                165                 170                 175

Ser Tyr Pro Thr Asn Lys Ala Gly Ala Lys Tyr Gly Thr Gly Tyr Cys
            180                 185                 190

Asp Ala Gln Cys Ala Arg Asp Leu Lys Phe Val Gly Gly Lys Ala Asn
        195                 200                 205
```

```
Ile Glu Gly Trp Arg Pro Ser Thr Asn Asp Ala Asn Ala Gly Val Gly
    210                 215                 220

Pro Met Gly Gly Cys Cys Ala Glu Ile Asp Val Trp Glu Ser Asn Ala
225                 230                 235                 240

His Ala Phe Ala Phe Thr Pro His Ala Cys Glu Asn Asn Asn Tyr His
                245                 250                 255

Ile Cys Glu Thr Ser Asn Cys Gly Gly Thr Tyr Ser Asp Asp Arg Phe
            260                 265                 270

Ala Gly Leu Cys Asp Ala Asn Gly Cys Asp Tyr Asn Pro Tyr Arg Met
        275                 280                 285

Gly Asn Pro Asp Phe Tyr Gly Lys Gly Lys Thr Leu Asp Thr Ser Arg
    290                 295                 300

Lys Phe Thr Val Val Thr Arg Phe Gln Glu Asn Asp Leu Ser Gln Tyr
305                 310                 315                 320

Phe Ile Gln Asp Gly Arg Lys Ile Glu Ile Pro Pro Thr Trp Asp
                325                 330                 335

Gly Leu Pro Lys Ser Ser His Ile Thr Pro Glu Leu Cys Ala Thr Gln
            340                 345                 350

Phe Asp Val Phe Asp Asp Arg Asn Arg Phe Glu Glu Val Gly Gly Phe
        355                 360                 365

Pro Ala Leu Asn Ala Ala Leu Arg Ile Pro Met Val Leu Val Met Ser
    370                 375                 380

Ile Trp Asp Asp His Tyr Ala Asn Met Leu Trp Leu Asp Ser Val Tyr
385                 390                 395                 400

Pro Pro Glu Lys Glu Gly Thr Pro Gly Ala Glu Arg Gly Pro Cys Pro
                405                 410                 415

Gln Thr Ser Gly Val Pro Ala Glu Val Glu Ala Gln Tyr Pro Asn Ala
            420                 425                 430

Lys Val Val Trp Ser Asn Ile Arg Phe Gly Pro Ile Gly Ser Thr Tyr
        435                 440                 445

Asn Met
    450

<210> SEQ ID NO 55
<211> LENGTH: 1599
<212> TYPE: DNA
<213> ORGANISM: Chaetomidium pingtungium
<220> FEATURE:
<221> NAME/KEY: CDS
<222> LOCATION: (1)..(1599)

<400> SEQUENCE: 55 atg ctg gcc tcc acc ttc tcc tac cgc atg tac aag acc gcg ctc atc      48
Met Leu Ala Ser Thr Phe Ser Tyr Arg Met Tyr Lys Thr Ala Leu Ile
1               5                   10                  15 ctg gcc gcc ctt ctg ggc tct ggc cag gct cag cag gtc ggt act tcc      96
Leu Ala Ala Leu Leu Gly Ser Gly Gln Ala Gln Gln Val Gly Thr Ser
            20                  25                  30 cag gcg gaa gtg cat ccg tcc atg acc tgg cag agc tgc acg gct ggc     144
Gln Ala Glu Val His Pro Ser Met Thr Trp Gln Ser Cys Thr Ala Gly
        35                  40                  45 ggc agc tgc acc acc aac aac ggc aag gtg gtc atc gac gcg aac tgg     192
Gly Ser Cys Thr Thr Asn Asn Gly Lys Val Val Ile Asp Ala Asn Trp
    50                  55                  60 cgt tgg gtg cac aaa gtc ggc gac tac acc aac tgc tac acc ggc aac     240
Arg Trp Val His Lys Val Gly Asp Tyr Thr Asn Cys Tyr Thr Gly Asn
65                  70                  75                  80
```

```
acc tgg gac acg act atc tgc cct gac gat gcg acc tgc gca tcc aac       288
Thr Trp Asp Thr Thr Ile Cys Pro Asp Asp Ala Thr Cys Ala Ser Asn
             85                  90                  95 tgc gcc ctt gag ggt gcc aac tac gaa tcc acc tat ggt gtg acc gcc       336
Cys Ala Leu Glu Gly Ala Asn Tyr Glu Ser Thr Tyr Gly Val Thr Ala
            100                 105                 110 agc ggc aat tcc ctc cgc ctc aac ttc gtc acc acc agc cag cag aag       384
Ser Gly Asn Ser Leu Arg Leu Asn Phe Val Thr Thr Ser Gln Gln Lys
        115                 120                 125 aac att ggc tcg cgt ctg tac atg atg aag gac gac tcg acc tac gag       432
Asn Ile Gly Ser Arg Leu Tyr Met Met Lys Asp Asp Ser Thr Tyr Glu
    130                 135                 140 atg ttt aag ctg ctg aac cag gag ttc acc ttc gat gtc gat gtc tcc       480
Met Phe Lys Leu Leu Asn Gln Glu Phe Thr Phe Asp Val Asp Val Ser
145                 150                 155                 160 aac ctc ccc tgc ggt ctc aac ggt gct ctg tac ttt gtc gcc atg gac       528
Asn Leu Pro Cys Gly Leu Asn Gly Ala Leu Tyr Phe Val Ala Met Asp
                165                 170                 175 gcc ggc ggt ggc atg tcc aag tac cca acc aac aag gcc ggt gcc aag       576
Ala Gly Gly Gly Met Ser Lys Tyr Pro Thr Asn Lys Ala Gly Ala Lys
            180                 185                 190 tac ggt act gga tac tgt gac tcg cag tgc cct cgc gac ctc aag ttc       624
Tyr Gly Thr Gly Tyr Cys Asp Ser Gln Cys Pro Arg Asp Leu Lys Phe
        195                 200                 205 atc aac ggt cag gcc aac gtt gaa ggg tgg cag ccc tcc tcc aac gat       672
Ile Asn Gly Gln Ala Asn Val Glu Gly Trp Gln Pro Ser Ser Asn Asp
    210                 215                 220 gcc aat gcg ggt acc ggc aac cac ggg tcc tgc tgc gcg gag atg gat       720
Ala Asn Ala Gly Thr Gly Asn His Gly Ser Cys Cys Ala Glu Met Asp
225                 230                 235                 240 atc tgg gag gcc aac agc atc tcc acg gcc ttc acc ccc cat ccg tgc       768
Ile Trp Glu Ala Asn Ser Ile Ser Thr Ala Phe Thr Pro His Pro Cys
                245                 250                 255 gac acg ccc ggc cag gtg atg tgc acc ggt gat gcc tgc ggt ggc acc       816
Asp Thr Pro Gly Gln Val Met Cys Thr Gly Asp Ala Cys Gly Gly Thr
            260                 265                 270 tac agc tcc gac cgc tac ggc ggc acc tgc gac ccc gac gga tgt gat       864
Tyr Ser Ser Asp Arg Tyr Gly Gly Thr Cys Asp Pro Asp Gly Cys Asp
        275                 280                 285 ttc aac tcc ttc cgc cag ggc aac aag acc ttc tac ggc cct ggc atg       912
Phe Asn Ser Phe Arg Gln Gly Asn Lys Thr Phe Tyr Gly Pro Gly Met
    290                 295                 300 acc gtc gac acc aag agc aag ttt acc gtc gtc acc cag ttc atc acc       960
Thr Val Asp Thr Lys Ser Lys Phe Thr Val Val Thr Gln Phe Ile Thr
305                 310                 315                 320 gac gac ggc acc tcc agc ggc acc ctc aag gag atc aag cgc ttc tac      1008
Asp Asp Gly Thr Ser Ser Gly Thr Leu Lys Glu Ile Lys Arg Phe Tyr
                325                 330                 335 gtg cag aac ggc aag gtg atc ccc aac tcg gag tcg acc tgg acc ggc      1056
Val Gln Asn Gly Lys Val Ile Pro Asn Ser Glu Ser Thr Trp Thr Gly
            340                 345                 350 gtc agc ggc aac tcc atc acc acc gag tac tgc acc gcc cag aag agc      1104
Val Ser Gly Asn Ser Ile Thr Thr Glu Tyr Cys Thr Ala Gln Lys Ser
        355                 360                 365 ctg ttc cag gac cag aac gtc ttc gaa aag cac ggc ggc ctc gag ggc      1152
Leu Phe Gln Asp Gln Asn Val Phe Glu Lys His Gly Gly Leu Glu Gly
    370                 375                 380 atg ggt gct gcc ctc gcc cag ggc atg gtt ctc gtc atg tcc ctg tgg      1200
Met Gly Ala Ala Leu Ala Gln Gly Met Val Leu Val Met Ser Leu Trp
385                 390                 395                 400
```

```
gat gat cac tcg gcc aac atg ctc tgg ctc gac agc aac tac ccg acc    1248
Asp Asp His Ser Ala Asn Met Leu Trp Leu Asp Ser Asn Tyr Pro Thr
                405                 410                 415 act gcc tct tcc acc act ccc ggc gtc gcc cgt ggt acc tgc gac atc    1296
Thr Ala Ser Ser Thr Thr Pro Gly Val Ala Arg Gly Thr Cys Asp Ile
            420                 425                 430 tcc tcc ggc gtc cct gcg gat gtc gag gcg aac cac ccc gac gcc tac    1344
Ser Ser Gly Val Pro Ala Asp Val Glu Ala Asn His Pro Asp Ala Tyr
        435                 440                 445 gtc gtc tac tcc aac atc aag gtc ggc ccc atc ggc tcg acc ttc aac    1392
Val Val Tyr Ser Asn Ile Lys Val Gly Pro Ile Gly Ser Thr Phe Asn
    450                 455                 460 agc ggt ggc tcg aac ccc ggt ggc gga acc acc acg aca act acc acc    1440
Ser Gly Gly Ser Asn Pro Gly Gly Gly Thr Thr Thr Thr Thr Thr Thr
465                 470                 475                 480 cag cct act acc acc acg acc acg gct gga aac cct ggc ggc acc gga    1488
Gln Pro Thr Thr Thr Thr Thr Thr Ala Gly Asn Pro Gly Gly Thr Gly
                485                 490                 495 gtc gca cag cac tat ggc cag tgt ggt gga atc gga tgg acc gga ccc    1536
Val Ala Gln His Tyr Gly Gln Cys Gly Gly Ile Gly Trp Thr Gly Pro
            500                 505                 510 aca acc tgt gcc agc cct tat acc tgc cag aag ctg aat gat tat tac    1584
Thr Thr Cys Ala Ser Pro Tyr Thr Cys Gln Lys Leu Asn Asp Tyr Tyr
        515                 520                 525 tct cag tgc ctg tag                                                1599
Ser Gln Cys Leu
    530

<210> SEQ ID NO 56
<211> LENGTH: 532
<212> TYPE: PRT
<213> ORGANISM: Chaetomidium pingtungium

<400> SEQUENCE: 56

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Gly Gly Gly Met Ser Lys Tyr Pro Thr Asn Lys Ala Gly Ala Lys
```

```
                180              185              190
Tyr Gly Thr Gly Tyr Cys Asp Ser Gln Cys Pro Arg Asp Leu Lys Phe
            195                  200                  205

Ile Asn Gly Gln Ala Asn Val Glu Gly Trp Gln Pro Ser Ser Asn Asp
        210                  215                  220

Ala Asn Ala Gly Thr Gly Asn His Gly Ser Cys Cys Ala Glu Met Asp
225                  230                  235                  240

Ile Trp Glu Ala Asn Ser Ile Ser Thr Ala Phe Thr Pro His Pro Cys
                245                  250                  255

Asp Thr Pro Gly Gln Val Met Cys Thr Gly Asp Ala Cys Gly Gly Thr
            260                  265                  270

Tyr Ser Ser Asp Arg Tyr Gly Gly Thr Cys Asp Pro Asp Gly Cys Asp
        275                  280                  285

Phe Asn Ser Phe Arg Gln Gly Asn Lys Thr Phe Tyr Gly Pro Gly Met
    290                  295                  300

Thr Val Asp Thr Lys Ser Lys Phe Thr Val Thr Gln Phe Ile Thr
305                  310                  315                  320

Asp Asp Gly Thr Ser Ser Gly Thr Leu Lys Glu Ile Lys Arg Phe Tyr
                325                  330                  335

Val Gln Asn Gly Lys Val Ile Pro Asn Ser Glu Ser Thr Trp Thr Gly
            340                  345                  350

Val Ser Gly Asn Ser Ile Thr Thr Glu Tyr Cys Thr Ala Gln Lys Ser
        355                  360                  365

Leu Phe Gln Asp Gln Asn Val Phe Glu Lys His Gly Gly Leu Glu Gly
    370                  375                  380

Met Gly Ala Ala Leu Ala Gln Gly Met Val Leu Val Met Ser Leu Trp
385                  390                  395                  400

Asp Asp His Ser Ala Asn Met Leu Trp Leu Asp Ser Asn Tyr Pro Thr
                405                  410                  415

Thr Ala Ser Ser Thr Thr Pro Gly Val Ala Arg Gly Thr Cys Asp Ile
            420                  425                  430

Ser Ser Gly Val Pro Ala Asp Val Glu Ala Asn His Pro Asp Ala Tyr
        435                  440                  445

Val Val Tyr Ser Asn Ile Lys Val Gly Pro Ile Gly Ser Thr Phe Asn
    450                  455                  460

Ser Gly Gly Ser Asn Pro Gly Gly Thr Thr Thr Thr Thr Thr
465                  470                  475                  480

Gln Pro Thr Thr Thr Thr Thr Ala Gly Asn Pro Gly Gly Thr Gly
                485                  490                  495

Val Ala Gln His Tyr Gly Gln Cys Gly Gly Ile Gly Trp Thr Gly Pro
            500                  505                  510

Thr Thr Cys Ala Ser Pro Tyr Thr Cys Gln Lys Leu Asn Asp Tyr Tyr
        515                  520                  525

Ser Gln Cys Leu
    530

<210> SEQ ID NO 57
<211> LENGTH: 1383
<212> TYPE: DNA
<213> ORGANISM: Sporotrichum pruinosum
<220> FEATURE:
<221> NAME/KEY: CDS
<222> LOCATION: (1)..(1383)

<400> SEQUENCE: 57
```

```
atg ttc aag aaa gtc gcc ctc acc gct ctc tgc ttc ctc gcc gtc gca    48
Met Phe Lys Lys Val Ala Leu Thr Ala Leu Cys Phe Leu Ala Val Ala
1               5                   10                  15 cag gcc caa cag gtc ggt cgc gaa gtc gct gaa aac cac ccc cgt ctc    96
Gln Ala Gln Gln Val Gly Arg Glu Val Ala Glu Asn His Pro Arg Leu
            20                  25                  30 ccg tgg cag cgt tgc act cgc aac ggc gga tgc cag act gtc tct aac   144
Pro Trp Gln Arg Cys Thr Arg Asn Gly Gly Cys Gln Thr Val Ser Asn
        35                  40                  45 ggt cag gtc gtc ctc gac gcc aac tgg cga tgg ctc cac gtc acc gat   192
Gly Gln Val Val Leu Asp Ala Asn Trp Arg Trp Leu His Val Thr Asp
    50                  55                  60 ggc tac acc aac tgc tac acc ggt aac tcc tgg aac agc acc gtc tgc   240
Gly Tyr Thr Asn Cys Tyr Thr Gly Asn Ser Trp Asn Ser Thr Val Cys
65              70                  75                  80 tcc gac ccc acc acc tgc gct cag cga tgc gct ctc gag ggt gcc aac   288
Ser Asp Pro Thr Thr Cys Ala Gln Arg Cys Ala Leu Glu Gly Ala Asn
                85                  90                  95 tac cag caa acc tac ggt atc acc acc aac gga gac gcc ctc acc atc   336
Tyr Gln Gln Thr Tyr Gly Ile Thr Thr Asn Gly Asp Ala Leu Thr Ile
            100                 105                 110 aag ttc ctc acc cga tcc caa caa acc aac gtc ggt gct cgt gtc tac   384
Lys Phe Leu Thr Arg Ser Gln Gln Thr Asn Val Gly Ala Arg Val Tyr
        115                 120                 125 ctc atg gag aac gag aac cga tac cag atg ttc aac ctc ctc aac aag   432
Leu Met Glu Asn Glu Asn Arg Tyr Gln Met Phe Asn Leu Leu Asn Lys
    130                 135                 140 gag ttc acc ttc gac gtt gac gtc tcc aag gtt cct tgc ggt atc aac   480
Glu Phe Thr Phe Asp Val Asp Val Ser Lys Val Pro Cys Gly Ile Asn
145                 150                 155                 160 ggt gcc ctc tac ttc atc cag atg gac gcc gat ggt ggt atg agc aag   528
Gly Ala Leu Tyr Phe Ile Gln Met Asp Ala Asp Gly Gly Met Ser Lys
                165                 170                 175 caa ccc aac aac agg gct ggt gct aag tac ggt acc ggc tac tgc gac   576
Gln Pro Asn Asn Arg Ala Gly Ala Lys Tyr Gly Thr Gly Tyr Cys Asp
            180                 185                 190 tct cag tgc ccc cgt gac atc aag ttc att gac ggc gtg gcc aac agc   624
Ser Gln Cys Pro Arg Asp Ile Lys Phe Ile Asp Gly Val Ala Asn Ser
        195                 200                 205 gcc gac tgg act cca tcc gag acc gat ccc aat gcc gga agg ggt cgc   672
Ala Asp Trp Thr Pro Ser Glu Thr Asp Pro Asn Ala Gly Arg Gly Arg
    210                 215                 220 tac ggc att tgc tgc gcc gag atg gat atc tgg gag gcc aac tcc atc   720
Tyr Gly Ile Cys Cys Ala Glu Met Asp Ile Trp Glu Ala Asn Ser Ile
225                 230                 235                 240 tcc aat gcc tac acc ccc cac cct tgc cga acc cag aac gat ggt ggc   768
Ser Asn Ala Tyr Thr Pro His Pro Cys Arg Thr Gln Asn Asp Gly Gly
                245                 250                 255 tac cag cgc tgc gag ggc cgc gac tgc aac cag cct cgc tat gag ggt   816
Tyr Gln Arg Cys Glu Gly Arg Asp Cys Asn Gln Pro Arg Tyr Glu Gly
            260                 265                 270 ctt tgc gat cct gat ggc tgt gac tac aac ccc ttc gcc atg ggt aac   864
Leu Cys Asp Pro Asp Gly Cys Asp Tyr Asn Pro Phe Arg Met Gly Asn
        275                 280                 285 aag gac ttc tac gga ccc gga aag acc atc gac acc aac agg aag atg   912
Lys Asp Phe Tyr Gly Pro Gly Lys Thr Ile Asp Thr Asn Arg Lys Met
    290                 295                 300 acc gtc gtc acc caa ttc atc acc cac gac aac acc gac act ggc acc   960
Thr Val Val Thr Gln Phe Ile Thr His Asp Asn Thr Asp Thr Gly Thr
305                 310                 315                 320
```

```
ctc gtt gac atc cgc cgc ctc tac gtt caa gac ggc cgt gtc att gcc      1008
Leu Val Asp Ile Arg Arg Leu Tyr Val Gln Asp Gly Arg Val Ile Ala
                325                 330                 335 aac cct ccc acc aac ttc ccc ggt ctc atg ccc gcc cac gac tcc atc      1056
Asn Pro Pro Thr Asn Phe Pro Gly Leu Met Pro Ala His Asp Ser Ile
            340                 345                 350 acc gag cag ttc tgc act gac cag aag aac ctc ttc ggc gac tac agc      1104
Thr Glu Gln Phe Cys Thr Asp Gln Lys Asn Leu Phe Gly Asp Tyr Ser
        355                 360                 365 agc ttc gct cgt gac ggt ggt ctc gct cac atg ggt cgc tcc ctc gcc      1152
Ser Phe Ala Arg Asp Gly Gly Leu Ala His Met Gly Arg Ser Leu Ala
    370                 375                 380 aag ggt cac gtc ctc gct ctc tcc atc tgg aac gac cac ggt gcc cac      1200
Lys Gly His Val Leu Ala Leu Ser Ile Trp Asn Asp His Gly Ala His
385                 390                 395                 400 atg ttg tgg ctc gac tcc aac tac ccc acc gac gct gac ccc aac aag      1248
Met Leu Trp Leu Asp Ser Asn Tyr Pro Thr Asp Ala Asp Pro Asn Lys
                405                 410                 415 ccc ggt att gct cgt ggt acc tgc ccg acc act ggt ggc acc ccc cgt      1296
Pro Gly Ile Ala Arg Gly Thr Cys Pro Thr Thr Gly Gly Thr Pro Arg
            420                 425                 430 gaa acc gaa caa aac cac cct gat gcc cag gtc atc ttc tcc aac att      1344
Glu Thr Glu Gln Asn His Pro Asp Ala Gln Val Ile Phe Ser Asn Ile
        435                 440                 445 aaa ttc ggt gac atc ggc tcg act ttc tct ggt tac taa                  1383
Lys Phe Gly Asp Ile Gly Ser Thr Phe Ser Gly Tyr
    450                 455                 460

<210> SEQ ID NO 58
<211> LENGTH: 460
<212> TYPE: PRT
<213> ORGANISM: Sporotrichum pruinosum

<400> SEQUENCE: 58

Met Phe Lys Lys Val Ala Leu Thr Ala Leu Cys Phe Leu Ala Val Ala
1               5                   10                  15

Gln Ala Gln Gln Val Gly Arg Glu Val Ala Glu Asn His Pro Arg Leu
            20                  25                  30

Pro Trp Gln Arg Cys Thr Arg Asn Gly Gly Cys Gln Thr Val Ser Asn
        35                  40                  45

Gly Gln Val Val Leu Asp Ala Asn Trp Arg Trp Leu His Val Thr Asp
    50                  55                  60

Gly Tyr Thr Asn Cys Tyr Thr Gly Asn Ser Trp Asn Ser Thr Val Cys
65                  70                  75                  80

Ser Asp Pro Thr Thr Cys Ala Gln Arg Cys Ala Leu Glu Gly Ala Asn
                85                  90                  95

Tyr Gln Gln Thr Tyr Gly Ile Thr Thr Asn Gly Asp Ala Leu Thr Ile
            100                 105                 110

Lys Phe Leu Thr Arg Ser Gln Gln Thr Asn Val Gly Ala Arg Val Tyr
        115                 120                 125

Leu Met Glu Asn Glu Asn Arg Tyr Gln Met Phe Asn Leu Leu Asn Lys
    130                 135                 140

Glu Phe Thr Phe Asp Val Asp Val Ser Lys Val Pro Cys Gly Ile Asn
145                 150                 155                 160

Gly Ala Leu Tyr Phe Ile Gln Met Asp Ala Asp Gly Gly Met Ser Lys
                165                 170                 175

Gln Pro Asn Asn Arg Ala Gly Ala Lys Tyr Gly Thr Gly Tyr Cys Asp
```

```
                180                 185                 190
Ser Gln Cys Pro Arg Asp Ile Lys Phe Ile Asp Gly Val Ala Asn Ser
            195                 200                 205

Ala Asp Trp Thr Pro Ser Glu Thr Asp Pro Asn Ala Gly Arg Gly Arg
210                 215                 220

Tyr Gly Ile Cys Cys Ala Glu Met Asp Ile Trp Glu Ala Asn Ser Ile
225                 230                 235                 240

Ser Asn Ala Tyr Thr Pro His Pro Cys Arg Thr Gln Asn Asp Gly Gly
            245                 250                 255

Tyr Gln Arg Cys Glu Gly Arg Asp Cys Asn Gln Pro Arg Tyr Glu Gly
            260                 265                 270

Leu Cys Asp Pro Asp Gly Cys Asp Tyr Asn Pro Phe Arg Met Gly Asn
            275                 280                 285

Lys Asp Phe Tyr Gly Pro Gly Lys Thr Ile Asp Thr Asn Arg Lys Met
            290                 295                 300

Thr Val Val Thr Gln Phe Ile Thr His Asp Asn Thr Asp Thr Gly Thr
305                 310                 315                 320

Leu Val Asp Ile Arg Arg Leu Tyr Val Gln Asp Gly Arg Val Ile Ala
                325                 330                 335

Asn Pro Pro Thr Asn Phe Pro Gly Leu Met Pro Ala His Asp Ser Ile
            340                 345                 350

Thr Glu Gln Phe Cys Thr Asp Gln Lys Asn Leu Phe Gly Asp Tyr Ser
            355                 360                 365

Ser Phe Ala Arg Asp Gly Gly Leu Ala His Met Gly Arg Ser Leu Ala
370                 375                 380

Lys Gly His Val Leu Ala Leu Ser Ile Trp Asn Asp His Gly Ala His
385                 390                 395                 400

Met Leu Trp Leu Asp Ser Asn Tyr Pro Thr Ala Asp Pro Asn Lys
                405                 410                 415

Pro Gly Ile Ala Arg Gly Thr Cys Pro Thr Thr Gly Gly Thr Pro Arg
            420                 425                 430

Glu Thr Glu Gln Asn His Pro Asp Ala Gln Val Ile Phe Ser Asn Ile
            435                 440                 445

Lys Phe Gly Asp Ile Gly Ser Thr Phe Ser Gly Tyr
            450                 455                 460

<210> SEQ ID NO 59
<211> LENGTH: 1578
<212> TYPE: DNA
<213> ORGANISM: Scytalidium thermophilum
<220> FEATURE:
<221> NAME/KEY: CDS
<222> LOCATION: (1)..(1578)

<400> SEQUENCE: 59 atg cgt acc gcc aag ttc gcc acc ctc gcc gcc ctt gtg gcc tcg gcc      48
Met Arg Thr Ala Lys Phe Ala Thr Leu Ala Ala Leu Val Ala Ser Ala
1               5                   10                  15 gcc gcc cag cag gcg tgc agt ctc acc acc gag agg cac cct tcc ctc      96
Ala Ala Gln Gln Ala Cys Ser Leu Thr Thr Glu Arg His Pro Ser Leu
                20                  25                  30 tct tgg aag aag tgc acc gcc ggc ggc cag tgc cag acc gtc cag gct     144
Ser Trp Lys Lys Cys Thr Ala Gly Gly Gln Cys Gln Thr Val Gln Ala
            35                  40                  45 tcc atc act ctc gac tcc aac tgg cgc tgg act cac cag gtg tct ggc     192
Ser Ile Thr Leu Asp Ser Asn Trp Arg Trp Thr His Gln Val Ser Gly
        50                  55                  60
```

```
tcc acc aac tgc tac acg ggc aac aag tgg gat act agc atc tgc act        240
Ser Thr Asn Cys Tyr Thr Gly Asn Lys Trp Asp Thr Ser Ile Cys Thr
 65              70                  75                  80 gat gcc aag tcg tgc gct cag aac tgc tgc gtc gat ggt gcc gac tac        288
Asp Ala Lys Ser Cys Ala Gln Asn Cys Cys Val Asp Gly Ala Asp Tyr
                 85                  90                  95 acc agc acc tat ggc atc acc acc aac ggt gat tcc ctg agc ctc aag        336
Thr Ser Thr Tyr Gly Ile Thr Thr Asn Gly Asp Ser Leu Ser Leu Lys
            100                 105                 110 ttc gtc acc aag ggc cag cac tcg acc aac gtc ggc tcg cgt acc tac        384
Phe Val Thr Lys Gly Gln His Ser Thr Asn Val Gly Ser Arg Thr Tyr
        115                 120                 125 ctg atg gac ggc gag gac aag tat cag acc ttc gag ctc ctc ggc aac        432
Leu Met Asp Gly Glu Asp Lys Tyr Gln Thr Phe Glu Leu Leu Gly Asn
    130                 135                 140 gag ttc acc ttc gat gtc gat gtc tcc aac atc ggc tgc ggt ctc aac        480
Glu Phe Thr Phe Asp Val Asp Val Ser Asn Ile Gly Cys Gly Leu Asn
145                 150                 155                 160 ggc gcc ctg tac ttc gtc tcc atg gac gcc gat ggt ggt ctc agc cgc        528
Gly Ala Leu Tyr Phe Val Ser Met Asp Ala Asp Gly Gly Leu Ser Arg
                165                 170                 175 tat cct ggc aac aag gct ggt gcc aag tac ggt acc ggc tac tgc gat        576
Tyr Pro Gly Asn Lys Ala Gly Ala Lys Tyr Gly Thr Gly Tyr Cys Asp
            180                 185                 190 gct cag tgc ccc cgt gac atc aag ttc atc aac ggc gag gcc aac att        624
Ala Gln Cys Pro Arg Asp Ile Lys Phe Ile Asn Gly Glu Ala Asn Ile
        195                 200                 205 gag ggc tgg acc ggc tcc acc aac gac ccc aac gcc ggc gcg ggc cgc        672
Glu Gly Trp Thr Gly Ser Thr Asn Asp Pro Asn Ala Gly Ala Gly Arg
    210                 215                 220 tat ggt acc tgc tgc tct gag atg gat atc tgg gaa gcc aac aac atg        720
Tyr Gly Thr Cys Cys Ser Glu Met Asp Ile Trp Glu Ala Asn Asn Met
225                 230                 235                 240 gct act gcc ttc act cct cac cct tgc acc atc att ggc cag agc cgc        768
Ala Thr Ala Phe Thr Pro His Pro Cys Thr Ile Ile Gly Gln Ser Arg
                245                 250                 255 tgc gag ggc gac tcg tgc ggt ggc acc tac agc aac gag cgc tac gcc        816
Cys Glu Gly Asp Ser Cys Gly Gly Thr Tyr Ser Asn Glu Arg Tyr Ala
            260                 265                 270 ggc gtc tgc gac ccc gat ggc tgc gac ttc aac tcg tac cgc cag ggc        864
Gly Val Cys Asp Pro Asp Gly Cys Asp Phe Asn Ser Tyr Arg Gln Gly
        275                 280                 285 aat aag acc ttc tac ggc aag ggc atg acc gtc gac acc acc aag aag        912
Asn Lys Thr Phe Tyr Gly Lys Gly Met Thr Val Asp Thr Thr Lys Lys
    290                 295                 300 atc act gtc gtc acc cag ttc ctc aag gat gcc aac ggc gat ctc ggc        960
Ile Thr Val Val Thr Gln Phe Leu Lys Asp Ala Asn Gly Asp Leu Gly
305                 310                 315                 320 gag gtc aag cgc ttc tac gtc cag gat ggc aag atc atc ccc aac tcc       1008
Glu Val Lys Arg Phe Tyr Val Gln Asp Gly Lys Ile Ile Pro Asn Ser
                325                 330                 335 gag tcc acc atc ccc ggc gtc gag ggc aat tcc atc acc cag gac tgg       1056
Glu Ser Thr Ile Pro Gly Val Glu Gly Asn Ser Ile Thr Gln Asp Trp
            340                 345                 350 tgc gac cgc cag aag gtt gcc ttt ggc gac att gac gac ttc aac cgc       1104
Cys Asp Arg Gln Lys Val Ala Phe Gly Asp Ile Asp Asp Phe Asn Arg
        355                 360                 365 aag ggc ggc atg aag cag atg ggc aag gcc ctc gcc ggc ccc atg gtc       1152
Lys Gly Gly Met Lys Gln Met Gly Lys Ala Leu Ala Gly Pro Met Val
```

```
                370                 375                 380
ctg gtc atg tcc atc tgg gat gac cac gcc tcc aac atg ctc tgg ctc         1200
Leu Val Met Ser Ile Trp Asp Asp His Ala Ser Asn Met Leu Trp Leu
385                 390                 395                 400 gac tcg acc ttc cct gtc gat gcc gct ggc aag ccc ggc gcc gag cgc         1248
Asp Ser Thr Phe Pro Val Asp Ala Ala Gly Lys Pro Gly Ala Glu Arg
                405                 410                 415 ggt gcc tgc ccg acc acc tcg ggt gtc cct gct gag gtt gag gcc gag         1296
Gly Ala Cys Pro Thr Thr Ser Gly Val Pro Ala Glu Val Glu Ala Glu
            420                 425                 430 gcc ccc aac agc aac gtc gtc ttc tcc aac atc cgc ttc ggc ccc atc         1344
Ala Pro Asn Ser Asn Val Val Phe Ser Asn Ile Arg Phe Gly Pro Ile
        435                 440                 445 ggc tcg acc gtt gct ggt ctc ccc ggc gcg ggc aac ggc ggc aac aac         1392
Gly Ser Thr Val Ala Gly Leu Pro Gly Ala Gly Asn Gly Gly Asn Asn
    450                 455                 460 ggc ggc aac ccc ccg ccc ccc acc acc acc tcc tcg gct ccg gcc             1440
Gly Gly Asn Pro Pro Pro Pro Thr Thr Thr Thr Ser Ser Ala Pro Ala
465                 470                 475                 480 acc acc acc acc gcc agc gct ggc ccc aag gct ggc cac tgg cag cag         1488
Thr Thr Thr Thr Ala Ser Ala Gly Pro Lys Ala Gly His Trp Gln Gln
                485                 490                 495 tgc ggc ggc atc ggc ttc act ggc ccg acc cag tgc gag gag ccc tac         1536
Cys Gly Gly Ile Gly Phe Thr Gly Pro Thr Gln Cys Glu Glu Pro Tyr
            500                 505                 510 act tgc acc aag ctc aac gac tgg tac tct cag tgc ctg taa                 1578
Thr Cys Thr Lys Leu Asn Asp Trp Tyr Ser Gln Cys Leu
        515                 520                 525

<210> SEQ ID NO 60
<211> LENGTH: 525
<212> TYPE: PRT
<213> ORGANISM: Scytalidium thermophilum

<400> SEQUENCE: 60

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Lys Lys Cys Thr Ala Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175
```

Tyr Pro Gly Asn Lys Ala Gly Ala Lys Tyr Gly Thr Gly Tyr Cys Asp
                180                 185                 190

Ala Gln Cys Pro Arg Asp Ile Lys Phe Ile Asn Gly Glu Ala Asn Ile
            195                 200                 205

Glu Gly Trp Thr Gly Ser Thr Asn Asp Pro Asn Ala Gly Ala Gly Arg
        210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
290                 295                 300

Ile Thr Val Val Thr Gln Phe Leu Lys Asp Ala Asn Gly Asp Leu Gly
305                 310                 315                 320

Glu Val Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Phe Asn Arg
        355                 360                 365

Lys Gly Gly Met Lys Gln Met Gly Lys Ala Leu Ala Gly Pro Met Val
370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
450                 455                 460

Gly Gly Asn Pro Pro Pro Thr Thr Thr Thr Ser Ser Ala Pro Ala
465                 470                 475                 480

Thr Thr Thr Thr Ala Ser Ala Gly Pro Lys Ala Gly His Trp Gln Gln
                485                 490                 495

Cys Gly Gly Ile Gly Phe Thr Gly Pro Thr Gln Cys Glu Glu Pro Tyr
            500                 505                 510

Thr Cys Thr Lys Leu Asn Asp Trp Tyr Ser Gln Cys Leu
        515                 520                 525

<210> SEQ ID NO 61
<211> LENGTH: 519
<212> TYPE: DNA
<213> ORGANISM: Aspergillus sp.
<220> FEATURE:
<221> NAME/KEY: misc_feature
<222> LOCATION: (1)..(519)
<223> OTHER INFORMATION: Partial CBH1 encoding sequence

<400> SEQUENCE: 61
gagatggaca tatgggaggc caacagcatc tccacggcct tcacgcccca cccctgcgat      60

```
gtccccggcc aggtgatgtg cgagggcgac tcctgcggtg gcacctacag cagcgaccgc    120 tatgcggca  cctgcgatcc cgatggatgt gacttcaact cctaccgcca gggcaacaag    180
tccttctacg gccccggcat gaccgtcgac accaacagca aggtcaccgt cgtgactcag    240
ttcctcaccg acgacggcac tgccaccggc accctgtcgg agatcaagcg gttctacgtg    300
cagaacggca aggtcatccc caactccgag tcgacctggc ccggcgtcgg cggcaactcc    360
atcaccaccg actactgtct ggcccagaag agcctcttcg gcgataccga cgtcttcacc    420
aagcacggcg gtatggaggg catgggcgcc ccctcgccg  agggcatggt cctcgtcctg    480
agtctctggg acgaccacca ctccaacatg ctctggctg                          519

<210> SEQ ID NO 62
<211> LENGTH: 497
<212> TYPE: DNA
<213> ORGANISM: Scopulariopsis sp.
<220> FEATURE:
<221> NAME/KEY: misc_feature
<222> LOCATION: (1)..(497)
<223> OTHER INFORMATION: Partial CBH1 encoding sequence

<400> SEQUENCE: 62
gagatcgatg tgtgggagtc gaacgcctat gccttcgttt tcacgccgca cgcgtgcacg     60
accaacgagt accacgtctg cgagaccacc aactgcggtg gcacctactc ggaggaccgc    120
ttcaccggca agtgcgacgc caacggctgc gactacaacc cctaccgcat gggcaacccc    180
gacttctacg gcaagggcaa gacgctcgac accagccgca agttcaccgt cgtctcccgc    240
ttcgaggaga acaagctctc ccagtacttc atccaggacg gccgcaagat cgagatcccg    300
ccgccgacgt gggagggcat gcccaacagc agcgagatca cccccgagct ctgctccacc    360
atgttcgatg tgctcgacga ccgcaaccgc ttgcaggagg tcggcggctt cgagcagctg    420
aacaacgccc tccgggttcc catggtcctc gtcatgtcca tctgggacga ccactacgcc    480
aacatgctct ggctcga                                                   497

<210> SEQ ID NO 63
<211> LENGTH: 498
<212> TYPE: DNA
<213> ORGANISM: Fusarium sp.
<220> FEATURE:
<221> NAME/KEY: misc_feature
<222> LOCATION: (1)..(498)
<223> OTHER INFORMATION: Partial CBH1 encoding sequence

<400> SEQUENCE: 63
gagatggata tctgggaggc caacaagatc tccactgcct acactcccca cccctgcaag     60
agcctcaccc agcagtcctg cgagggcgat gcctgcggtg gcacctactc tactacccgc    120
tatgctggaa cttgcgaccc cgatggttgc gatttcaacc cttaccgcca gggcaacaag    180
accttctacg gccccggctc cggcttcaac gttgatacca ccaagaaggt gactgtcgtg    240
acccagttca tcaagggcag cgacggcaag cttttccgaga tcaagcgtct ctatgttcag    300
aatggcaagg tcattggcaa ccccagtct  gagattgcca gcaaccctgg cagcagcgtc    360
accgacagct tctgcaaggc ccagaaggtt gccttcaacg accccgatga cttcaacaag    420
aagggtggct ggagcggaat gagcgacgcc ctcgccaagc ccatggttct cgtcatgagc    480
ttgtggcacg acgtgagt                                                  498

<210> SEQ ID NO 64
```

```
<211> LENGTH: 525
<212> TYPE: DNA
<213> ORGANISM: Verticillium sp.
<220> FEATURE:
<221> NAME/KEY: misc_feature
<222> LOCATION: (1)..(525)
<223> OTHER INFORMATION: Partial CBH1 encoding sequence

<400> SEQUENCE: 64
```

| | | |
|---|---|---|
| gagatggata tctgggaggc caacaagatc tccacggcct acactcccca tccctgcaag | 60 |
| agcctcaccc agcagtcctg tgagggcgat gcctgcggtg cacctactc ttccacccgc | 120 |
| tatgctggaa cttgcgatcc cgatggctgc gatttcaacc cttaccgcca gggcaaccac | 180 |
| accttctacg gtcccggctc cggcttcaac gtcgatacca ccaagaaggt gactgtcgtg | 240 |
| acccagttca tcaagggcag cgacggcaag cttttccgaga tcaagcgtct ctatgttcag | 300 |
| aatggcaagg tcatcggcaa ccccagtcc gagattgcaa caaccccgg cagctccgtc | 360 |
| accgacagct tctgcaaggc ccagaaggtt gccttcaacg accccgatga cttcaacaag | 420 |
| aagggtggct ggagcggcat gaacgacgcc ctcgccaagc ccatggttct cgtcatgagc | 480 |
| ctgtggcacg acgtgagtaa tctaacccct gagtctcgga caaga | 525 |

```
<210> SEQ ID NO 65
<211> LENGTH: 1371
<212> TYPE: DNA
<213> ORGANISM: Pseudoplectania nigrella
<220> FEATURE:
<221> NAME/KEY: CDS
<222> LOCATION: (1)..(1371)

<400> SEQUENCE: 65
```

| | | |
|---|---|---|
| atg cta tcc aat ctc ctt ctc tca ctc tct ttc ctt tcc cta gcc tcc<br>Met Leu Ser Asn Leu Leu Leu Ser Leu Ser Phe Leu Ser Leu Ala Ser<br>1              5                  10              15 | 48 |
| ggg caa aac atc ggt acc aac acc gcc gaa agc cac ccc caa ctt cgt<br>Gly Gln Asn Ile Gly Thr Asn Thr Ala Glu Ser His Pro Gln Leu Arg<br>               20                  25                  30 | 96 |
| tct caa acc tgc acc aaa ggc aac gga tgc agc acc caa tcc acc tcc<br>Ser Gln Thr Cys Thr Lys Gly Asn Gly Cys Ser Thr Gln Ser Thr Ser<br>        35                  40                  45 | 144 |
| gta gtc ctg gac tcc aac tgg cgc tgg ctg cac aat aat gga ggt tca<br>Val Val Leu Asp Ser Asn Trp Arg Trp Leu His Asn Asn Gly Gly Ser<br>50                  55                  60 | 192 |
| acg aac tgc tac acc ggc aat tcc tgg gac tct aca tta tgt ccc gac<br>Thr Asn Cys Tyr Thr Gly Asn Ser Trp Asp Ser Thr Leu Cys Pro Asp<br>65                  70                  75                  80 | 240 |
| cca gtt acc tgc gcc aag aac tgt gct ctc gac ggt gcc gac tat tct<br>Pro Val Thr Cys Ala Lys Asn Cys Ala Leu Asp Gly Ala Asp Tyr Ser<br>               85                  90                  95 | 288 |
| ggg aca tac gga atc acc tct acg gga gat gct ttg acg ttg aag ttt<br>Gly Thr Tyr Gly Ile Thr Ser Thr Gly Asp Ala Leu Thr Leu Lys Phe<br>             100                105             110 | 336 |
| gtt act cag ggt cct tat tcg act aat att gga tct cgg gta tac cta<br>Val Thr Gln Gly Pro Tyr Ser Thr Asn Ile Gly Ser Arg Val Tyr Leu<br>             115                120             125 | 384 |
| atg gcg agt gat act cag tat aag atg ttc cag ctc aag aac aag gag<br>Met Ala Ser Asp Thr Gln Tyr Lys Met Phe Gln Leu Lys Asn Lys Glu<br>             130                135             140 | 432 |
| ttt acg ttt gat gtt gat gtc tct aat ctt cct tgt gga tta aac gga<br>Phe Thr Phe Asp Val Asp Val Ser Asn Leu Pro Cys Gly Leu Asn Gly<br>145                  150                  155                  160 | 480 |

-continued

| | | |
|---|---|---|
| gcg ttg tat ttt gtg gag atg gat gcg gat gga gga atg tcg aaa tac<br>Ala Leu Tyr Phe Val Glu Met Asp Ala Asp Gly Gly Met Ser Lys Tyr<br>165 170 175 | | 528 |
| ccg tct aat aaa gcc ggg gca aaa tat gga acc ggg tat tgt gat gcg<br>Pro Ser Asn Lys Ala Gly Ala Lys Tyr Gly Thr Gly Tyr Cys Asp Ala<br>180 185 190 | | 576 |
| cag tgt cca cat gat atc aaa ttt atc aac ggg gag gca aat ctc cta<br>Gln Cys Pro His Asp Ile Lys Phe Ile Asn Gly Glu Ala Asn Leu Leu<br>195 200 205 | | 624 |
| gac tgg acg cct tca acc agc gac aaa aat gcc ggc tcc gga cgt tac<br>Asp Trp Thr Pro Ser Thr Ser Asp Lys Asn Ala Gly Ser Gly Arg Tyr<br>210 215 220 | | 672 |
| ggg acc tgt tgt caa gaa atg gac atc tgg gaa gcc aac agc atg gca<br>Gly Thr Cys Cys Gln Glu Met Asp Ile Trp Glu Ala Asn Ser Met Ala<br>225 230 235 240 | | 720 |
| acc gcc tat aca ccg cat ccc tgt agt gtc tca gga cct acc cga tgc<br>Thr Ala Tyr Thr Pro His Pro Cys Ser Val Ser Gly Pro Thr Arg Cys<br>245 250 255 | | 768 |
| tca gga acc caa tgt ggg gat ggt tct aac cgt cat aac gga att tgc<br>Ser Gly Thr Gln Cys Gly Asp Gly Ser Asn Arg His Asn Gly Ile Cys<br>260 265 270 | | 816 |
| gat aaa gat ggc tgc gat ttc aat tcc tac cgt atg ggc aat acg aca<br>Asp Lys Asp Gly Cys Asp Phe Asn Ser Tyr Arg Met Gly Asn Thr Thr<br>275 280 285 | | 864 |
| ttc ttc ggc aag gga gca acg gtt aac acc aac tcc aaa ttt act gtt<br>Phe Phe Gly Lys Gly Ala Thr Val Asn Thr Asn Ser Lys Phe Thr Val<br>290 295 300 | | 912 |
| gta acg caa ttc atc acc tcc gac aac acc tca act gga gcg cta aag<br>Val Thr Gln Phe Ile Thr Ser Asp Asn Thr Ser Thr Gly Ala Leu Lys<br>305 310 315 320 | | 960 |
| gag att cgt cgt ctt tat att cag aat gga aaa gtc atc cag aac tcg<br>Glu Ile Arg Arg Leu Tyr Ile Gln Asn Gly Lys Val Ile Gln Asn Ser<br>325 330 335 | | 1008 |
| aaa agt aat atc tcc ggc atg tca gct tac gac tct ata acc gag gat<br>Lys Ser Asn Ile Ser Gly Met Ser Ala Tyr Asp Ser Ile Thr Glu Asp<br>340 345 350 | | 1056 |
| ttc tgt gcc gct caa aaa acc gca ttt gga gac aca aat gac ttt aag<br>Phe Cys Ala Ala Gln Lys Thr Ala Phe Gly Asp Thr Asn Asp Phe Lys<br>355 360 365 | | 1104 |
| gca aag ggc gga ttt aca aac ctt ggg aat gcg ttg caa aag gga atg<br>Ala Lys Gly Gly Phe Thr Asn Leu Gly Asn Ala Leu Gln Lys Gly Met<br>370 375 380 | | 1152 |
| gtt ttg gcg ttg agt att tgg gat gat cat gct gcg cag atg ctt tgg<br>Val Leu Ala Leu Ser Ile Trp Asp Asp His Ala Ala Gln Met Leu Trp<br>385 390 395 400 | | 1200 |
| ttg gat agt tct tac ccg ctc gat aaa gac cct tct caa cca ggt gtt<br>Leu Asp Ser Ser Tyr Pro Leu Asp Lys Asp Pro Ser Gln Pro Gly Val<br>405 410 415 | | 1248 |
| aag agg ggc gcg tgt gct acc tct tct ggt aaa ccg tcg gat gtc gag<br>Lys Arg Gly Ala Cys Ala Thr Ser Ser Gly Lys Pro Ser Asp Val Glu<br>420 425 430 | | 1296 |
| aac cag tct ccg aat gcg tcg gtg act ttt tcg aac att aag ttt ggg<br>Asn Gln Ser Pro Asn Ala Ser Val Thr Phe Ser Asn Ile Lys Phe Gly<br>435 440 445 | | 1344 |
| gat att gga tcg act tat tcc tct tag<br>Asp Ile Gly Ser Thr Tyr Ser Ser<br>450 455 | | 1371 |

<210> SEQ ID NO 66
<211> LENGTH: 456

<212> TYPE: PRT
<213> ORGANISM: Pseudoplectania nigrella

<400> SEQUENCE: 66

```
Met Leu Ser Asn Leu Leu Ser Leu Ser Phe Leu Ser Leu Ala Ser
1               5                   10                  15

Gly Gln Asn Ile Gly Thr Asn Thr Ala Glu Ser His Pro Gln Leu Arg
                20                  25                  30

Ser Gln Thr Cys Thr Lys Gly Asn Gly Cys Ser Thr Gln Ser Thr Ser
            35                  40                  45

Val Val Leu Asp Ser Asn Trp Arg Trp Leu His Asn Asn Gly Gly Ser
        50                  55                  60

Thr Asn Cys Tyr Thr Gly Asn Ser Trp Asp Ser Thr Leu Cys Pro Asp
65                  70                  75                  80

Pro Val Thr Cys Ala Lys Asn Cys Ala Leu Asp Gly Ala Asp Tyr Ser
                85                  90                  95

Gly Thr Tyr Gly Ile Thr Ser Thr Gly Asp Ala Leu Thr Leu Lys Phe
                100                 105                 110

Val Thr Gln Gly Pro Tyr Ser Thr Asn Ile Gly Ser Arg Val Tyr Leu
            115                 120                 125

Met Ala Ser Asp Thr Gln Tyr Lys Met Phe Gln Leu Lys Asn Lys Glu
        130                 135                 140

Phe Thr Phe Asp Val Asp Val Ser Asn Leu Pro Cys Gly Leu Asn Gly
145                 150                 155                 160

Ala Leu Tyr Phe Val Glu Met Asp Ala Asp Gly Gly Met Ser Lys Tyr
                165                 170                 175

Pro Ser Asn Lys Ala Gly Ala Lys Tyr Gly Thr Gly Tyr Cys Asp Ala
                180                 185                 190

Gln Cys Pro His Asp Ile Lys Phe Ile Asn Gly Glu Ala Asn Leu Leu
            195                 200                 205

Asp Trp Thr Pro Ser Thr Ser Asp Lys Asn Ala Gly Ser Gly Arg Tyr
        210                 215                 220

Gly Thr Cys Cys Gln Glu Met Asp Ile Trp Glu Ala Asn Ser Met Ala
225                 230                 235                 240

Thr Ala Tyr Thr Pro His Pro Cys Ser Val Ser Gly Pro Thr Arg Cys
                245                 250                 255

Ser Gly Thr Gln Cys Gly Asp Gly Ser Asn Arg His Asn Gly Ile Cys
                260                 265                 270

Asp Lys Asp Gly Cys Asp Phe Asn Ser Tyr Arg Met Gly Asn Thr Thr
            275                 280                 285

Phe Phe Gly Lys Gly Ala Thr Val Asn Thr Asn Ser Lys Phe Thr Val
        290                 295                 300

Val Thr Gln Phe Ile Thr Ser Asp Asn Thr Ser Thr Gly Ala Leu Lys
305                 310                 315                 320

Glu Ile Arg Arg Leu Tyr Ile Gln Asn Gly Lys Val Ile Gln Asn Ser
                325                 330                 335

Lys Ser Asn Ile Ser Gly Met Ser Ala Tyr Asp Ser Ile Thr Glu Asp
                340                 345                 350

Phe Cys Ala Ala Gln Lys Thr Ala Phe Gly Asp Thr Asn Asp Phe Lys
            355                 360                 365

Ala Lys Gly Gly Phe Thr Asn Leu Gly Asn Ala Leu Gln Lys Gly Met
        370                 375                 380

Val Leu Ala Leu Ser Ile Trp Asp Asp His Ala Ala Gln Met Leu Trp
385                 390                 395                 400
```

```
Leu Asp Ser Ser Tyr Pro Leu Asp Lys Asp Pro Ser Gln Pro Gly Val
            405                 410                 415

Lys Arg Gly Ala Cys Ala Thr Ser Ser Gly Lys Pro Ser Asp Val Glu
        420                 425                 430

Asn Gln Ser Pro Asn Ala Ser Val Thr Phe Ser Asn Ile Lys Phe Gly
        435                 440                 445

Asp Ile Gly Ser Thr Tyr Ser Ser
    450                 455

<210> SEQ ID NO 67
<211> LENGTH: 951
<212> TYPE: DNA
<213> ORGANISM: Phytophthora infestans
<220> FEATURE:
<221> NAME/KEY: misc_feature
<222> LOCATION: (1)..(951)
<223> OTHER INFORMATION: Partial CBH1 encoding sequence

<400> SEQUENCE: 67
tgcgatgctg atggttgtga cttcaactct taccgccagg gtaacacctc tttctatggt    60
gcaggtctta ccgtgaacac caacaaagtt ttcaccgttg taacccaatt catcaccaac   120
gatggaacag cttcaggtac cttgaaagaa atccgacgat tctatgttca gaatggcgtc   180
gtgattccaa actcgcaatc cacaatcgct ggagttccag gaaattccat caccgactct   240
ttctgtgccg cacaaaagac tgcttttggt gacaccaacg aattcgctac taagggaggt   300
cttgccacaa tgagcaaagc tttggcaaag ggtatggtac ttgtcatgtc catttgggat   360
gaccataccg ccaacatgtt gtggctcgat gccccttacc cagcaaccaa atccccaagc   420
gccccaggtg tcactcgagg atcatgcagt gctacttcag gtaacccccgt tgatgttgaa   480 gccaattctc caggttcttc cgtcaccttc tcaaacatca gtggggtcc catcaactct   540 acctacactg gatctggagc cgccccaagt gttccaggca ctacaaccgt tagctcggca   600
cccgcatcga ctgcaacttc aggagctggt ggtgtcgcta agtatgccca atgtggaggt   660
actggataca gtggagctac cgcttgcgtt tcaggcagca cctgtgttgc cctcaaccct   720
tactactccc aatgccaata gattgtttcc ctcaggagca attaggtttc caacctaagg   780
ggagagatct tcacaagtct gtacataggg tcagctaaat gttgatcatt catattcttt   840
catgtattta gttgttgaca atttgaagtt gcaagtcaag acgggaaaac agaagcagga   900
aatatatggg acataacaaa gtcaatcgtt tacataagaa ccttctttaa a            951
```